(12) United States Patent
Gruen et al.

(10) Patent No.: US 9,828,639 B2
(45) Date of Patent: Nov. 28, 2017

(54) IDENTIFICATION OF GENE ASSOCIATED WITH READING DISABILITY AND USES THEREFOR

(71) Applicants: Jeffrey R. Gruen, Hamden, CT (US); Haiying Meng, Hamden, CT (US)

(72) Inventors: Jeffrey R. Gruen, Hamden, CT (US); Haiying Meng, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 13/967,291

(22) Filed: Aug. 14, 2013

(65) Prior Publication Data
US 2014/0051076 A1 Feb. 20, 2014

Related U.S. Application Data

(63) Continuation of application No. 11/662,325, filed as application No. PCT/US2005/033114 on Sep. 14, 2005, now abandoned.

(60) Provisional application No. 60/610,023, filed on Sep. 14, 2004, provisional application No. 60/685,101, filed on May 26, 2005.

(51) Int. Cl.
*C12Q 1/68* (2006.01)
(52) U.S. Cl.
CPC ..... *C12Q 1/6883* (2013.01); *C12Q 2600/156* (2013.01); *C12Q 2600/158* (2013.01); *C12Q 2600/172* (2013.01)
(58) Field of Classification Search
None
See application file for complete search history.

(56) References Cited

U.S. PATENT DOCUMENTS

| 5,525,467 A | 6/1996 | Anand |
| 6,060,240 A | 5/2000 | Kamb et al. |
| 6,323,009 B1 | 11/2001 | Lasken et al. |
| 7,355,022 B2 | 4/2008 | Kere et al. |
| 2003/0118998 A1 | 6/2003 | Dean et al. |
| 2015/0299792 A1 | 10/2015 | Gruen |

FOREIGN PATENT DOCUMENTS

WO WO 2014/074755 A1 5/2014

OTHER PUBLICATIONS

Ludwig et al. Psychiatric Genetics (2008) 18: 310-312.*
Lind et al. European Journal of Human Genetics (2010) 18: 668-673.*
Nordfors et al. Human Mutation (2002) 19: 395-401.*
Database NCBI Dec. 19, 2003 XP002393445, GenBank ID 1RY1-P.
Database NCBI Apr. 26, 2004 XP002393446, GenBank Accession No. AB175156.
Database NCBI Jul. 13, 1983 XP002393447, GenBank Accession No. V00837.
Brkanac, Z., et al., (2007). "Evaluation of candidate genes for DYX1 and DYX2 in families with dyslexia." Am J Med Genet B Neuropsychiatr Genet 144B(4): 556-60.
Cope, N., et al. (2005). "Strong evidence that KIAA0319 on chromosome 6p is a susceptibility gene for developmental dyslexia." Am J Hum Genet 76(4): 581-91.
Deffenbacher et al., "Refinement of the 6p21.3 Quantitative Trait Locus Influencing Dyslexia: Linkage and Association Analyses," *Hum Genet* 115:128-138 (2004).
Francks, et al. (2004). "A 77-kilobase region of chromosome 6p22.2 is associated with dyslexia in families from the United Kingdom and from the United States." *Am J Hum Genet* 75(6): 1046-58.
Gibson, C.J. and Gruen, JR, (2008) "The Human Lexinome: genes of language and reading". J Comm. Disorders, 41: 409-420.
Harold, D., et al., (2006). "Further evidence that the KIAA0319 gene confers susceptibility to developmental dyslexia." Mol Psychiatry 11(12): 1085-91, 1061.
Londin et al., "A Transcription Map of the 6p22.3 Reading Disability Locus Identifying Candidate Genes," *BMC Genomics* 4(25):1-8 (2003).
Ludwig, K. U., et al. (2008). "Investigation of interaction between DCDC2 and KIAA0319 in a large German dyslexia sample." J Neural Transm 115(11): 1587-9.
Meng et al., "Candidates for the 6p21.3-22 Reading Disability (DYX2) Gene," Apr. 2004, pp. 580A XP009070445.
Meng, H., et al., (2005). "DCDC2 is associated with reading disability and modulates neuronal development in the brain." *Proc Natl Acad Sci U S A* 102(47): 17053-8.
Schumacher et al., "Independent Evidence for the VMP/DCDC2/KAAG1 Gene Locus on Chromosomal Region 6P22 as Susceptibility Factor for Dyslexia," Sep. 2005 XP009070442.
Schumacher, J., et al., (2006). "Strong genetic evidence of DCDC2 as a susceptibility gene for dyslexia." Am J Hum Genet 78(1): 52-62.
Shaywitz, S.E., "Dyslexia, in Brain, Behavior, and Learning in Language and Reading Disorders." Challenges in Language and Literacy, M. Mody, E.R. Silliman, eds. Guilford Press, NY, 2008, 209-239.
Shaywitz, S.E., "Dyslexia, in Handbook of Child Language Disorders." Schwartz, R.G., ed. Psychology Press, London, 2008. pp. 115-139.
Shaywitz, S.E., et al., (2007) "Management of dyslexia, its rationale, and underlying neurobiology." Pediatric Clinics of North America. 54(3):609-23, viii.
Van Den Eynde et al., "A New Antigen Recognized by Cytolytic T Lymphocytes on a Human Kidney Tumor Results from Reverse Strand Transcription," *I Exp. Med* 190(12):1793-1799 (1999).
Wilcke, A., et al. (2009). "The role of gene DCDC2 in German dyslexics." Ann Dyslexia 59(1): 1-11.

(Continued)

*Primary Examiner* — Angela M Bertagna
(74) *Attorney, Agent, or Firm* — Wolf, Greenfield & Sacks, P.C.

(57) ABSTRACT

The present invention relates to identification of a human gene, DCDC2 (MIM: 605755), associated with susceptibility for developing reading disability (RD), which is useful in identifying or aiding in identifying individuals at risk for developing RD, as well as for diagnosing or aiding in the diagnosis of RD.

7 Claims, 13 Drawing Sheets

(56) References Cited

OTHER PUBLICATIONS

International Search Report and Written Opinion for International Application No. PCT/US2013/069015 dated Feb. 20, 2014.
International Preliminary Report on Patentability for International Application No. PCT/US2013/069015 dated May 21, 2015.
Ahern, Biochemical, reagents kits offer scientists good return on investment. The Scientist. 1995; 9(15):20-28.
Ahn et al., Peaks of linkage are localized by a BAC/PAC contig of the 6p reading disability locus. Genomics. Nov. 2001;78(1-2):19-29.
Beaver et al., Association between the A1 allele of the DRD2 gene and reduced verbal abilities in adolescence and early adulthood. J Neural Transm (Vienna). Jul. 2010;117(7):827-30. doi: 10.1007/s00702-010-0421-8. Epub Jun. 9, 2010.
Benson et al., GenBank. Nucleic Acids Res. Jan. 2009;37(Database issue):D26-31. doi: 10.1093/nar/gkn723. Epub Oct. 21, 2008.
Cardon et al., Quantitative trait locus for reading disability on chromosome 6. Science. Oct. 14, 1994;266(5183):276-9. Erratum in: Science. Jun. 16, 1995;268(5217):1553.
Cope et al., Variants in the DYX2 locus are associated with altered brain activation in reading-related brain regions in subjects with reading disability. Neuroimage. Oct. 15, 2012;63(1):148-56. doi: 10.1016/j.neuroimage.2012.06.037. Epub Jun. 27, 2012.
Couto et al., Association of reading disabilities with regions marked by acetylated H3 histones in KIAA0319. Am J Med Genet B Neuropsychiatr Genet. Mar. 5, 2010;153B(2):447-62. doi: 10.1002/ajmg.b.30999.
De Backer et al., Genomic profiling of the response of Candida albicans to itraconazole treatment using a DNA microarray. Antimicrob Agents Chemother. Jun. 2001;45(6):1660-70.
Dennis et al., A common variant associated with dyslexia reduces expression of the KIAA0319 gene. PLoS Genet. Mar. 2009;5(3):e1000436. doi: 10.1371/journal.pgen.1000436. Epub Mar. 27, 2009.
Eicher et al., Associations of prenatal nicotine exposure and the dopamine related genes ANKK1 and DRD2 to verbal language. PLoS One. May 15, 2013;8(5):e63762. doi:10.1371/journal.pone.0063762. Print 2013.
Eicher et al., Imaging-genetics in dyslexia: connecting risk genetic variants to brain neuroimaging and ultimately to reading impairments. Mol Genet Metab. Nov. 2013;110(3):201-12. doi: 10.1016/j.ymgme.2013.07.001. Epub Jul. 17, 2013. Review.
Eicher et al., Pediatric Imaging, Neurocognition, and Genetics Study. Genome-wide association study of shared components of reading disability and language impairment. Genes Brain Behav. Nov. 2013;12(8):792-801. doi: 10.1111/gbb.12085. Epub Oct. 9, 2013.
Elbert et al., Genetic variation in the KIAA0319 5' region as a possible contributor to dyslexia. Behav Genet. Jan. 2011;41(1):77-89. doi: 10.1007/s10519-010-9434-1. Epub Jan. 5, 2011.
Gayán et al., Quantitative-trait locus for specific language and reading deficits on chromosome 6p. Am J Hum Genet. Jan. 1999;64(1):157-64.
Golding et al., ALSPAC Study Team. ALSPAC—The Avon Longitudinal Study of Parents and Children. I. Study methodology. Paediatr Perinat Epidemiol. Jan. 2001;15(1):74-87.
Graham et al., Decoding the genetics of speech and language. Curr Opin Neurobiol. Feb. 2013;23(1):43-51. doi: 10.1016/j.conb.2012.11.006. Epub Dec. 7, 2012. Review.
Han et al., Efficient association study design via power-optimized tag SNP selection. Ann Hum Genet. Nov. 2008;72(Pt 6):834-47. doi: 10.1111/j.1469-1809.2008.00469.x. Epub Aug. 13, 2008.
Kaminen et al., A genome scan for developmental dyslexia confirms linkage to chromosome 2p11 and suggests a new locus on 7q32. J Med Genet. May 2003;40(5):340-5.
Kaplan et al., Evidence for linkage and association with reading disability on 6p21.3-22. Am J. Hum Genet. May 2002;70(5):1287-98. Epub Apr. 10, 2002.
Kwok, High-throughput genotyping assay approaches. Pharmacogenomics. Feb. 2000;1(1):95-100. Review.
Landi et al., The COMT VAL/MET polymorphism is associated with reading-related skills and consistent patterns of functional neural activation. Dev Sci. Jan. 2013;16(1):13-23. doi: 10.1111/j.1467-7687.2012.01180.x. Epub Oct. 3, 2012.
Lind et al., Dyslexia and DCDC2: normal variation in reading and spelling is associated with DCDC2 polymorphisms in an Australian population sample. Eur J Hum Genet. Jun. 2010;18(6):668-73. doi: 10.1038/ejhg.2009.237. Epub Jan. 13, 2010.
Livak et al., Oligonucleotides with fluorescent dyes at opposite ends provide a quenched probe system useful for detecting PCR product and nucleic acid hybridization. PCR Methods Appl. Jun. 1995;4(6):357-62.
Luciano et al., A haplotype spanning KIAA0319 and TTRAP is associated with normal variation in reading and spelling ability. Biol Psychiatry. Oct. 1, 2007;62(7):811-7. Epub Jun. 27, 2007.
Ludwig et al., Investigation of the DCDC2 intron 2 deletion/compound short tandem repeat polymorphism in a large German dyslexia sample. Psychiatr Genet. Dec. 2008;18(6):310-2. doi: 10.1097/YPG.0b013e3283063a78.
Marino et al., DCDC2 genetic variants and susceptibility to developmental dyslexia. Psychiatr Genet. Feb. 2012;22(1):25-30. doi: 10.1097/YPG.0b013e32834acdb2.
Meng et al., A dyslexia-associated variant in DCDC2 changes gene expression. Behav Genet. Jan. 2011;41(1):58-66. doi: 10.1007/s10519-010-9408-3. Epub Nov. 2, 2010.
Newbury et al., CMIP and ATP2C2 modulate phonological short-term memory in language impairment. Am J Hum Genet. Aug. 2009;85(2):264-72. doi: 10.1016/j.ajhg.2009.07.004. Epub Jul. 30, 2009.
Newbury et al., Investigation of dyslexia and SLI risk variants in reading- and language-impaired subjects. Behav Genet. Jan. 2011;41(1):90-104. doi: 10.1007/s10519-010-9424-3. Epub Dec. 17, 2010.
Nordfors et al., Large-scale genotyping of single nucleotide polymorphisms by Pyrosequencingtrade mark and validation against the 5'nuclease (Taqman((R))) assay. Hum Mutat. Apr. 2002;19(4):395-401.
Nunes et al., Learning morphological and phonological spelling rules: an intervention study. Scientific Studies of Reading. 2003;7(3):289-307. doi: 10.1207/s1532799xssr0703_6.
Paracchini et al., Association of the KIAA0319 dyslexia susceptibility gene with reading skills in the general population. Am J Psychiatry. Dec. 2008;165(12):1576-84. doi: 10.1176/appi.ajp.2008.07121872. Epub Oct. 1, 2008.
Paracchini et al., The chromosome 6p22 haplotype associated with dyslexia reduces the expression of KIAA0319, a novel gene involved in neuronal migration. Hum Mol Genet. May 15, 2006;15(10):1659-66. Epub Apr. 6, 2006.
Peter et al., Replication of CNTNAP2 association with nonword repetition and support for FOXP2 association with timed reading and motor activities in a dyslexia family sample. J Neurodev Disord. Mar. 2011;3(1):39-49. doi: 10.1007/s11689-010-9065-0. Epub Nov. 9, 2010.
Pinel et al., Genetic variants of FOXP2 and KIAA0319/TTRAP/THEM2 locus are associated with altered brain activation in distinct language-related regions. J Neurosci. Jan. 18, 2012;32(3):817-25. doi:10.1523/JNEUROSCI.5996-10.2012.
Plomin et al., A functional polymorphism in the succinate-semialdehyde dehydrogenase (aldehyde dehydrogenase 5 family, member A1) gene is associated with cognitive ability. Mol Psychiatry. Jun. 2004;9(6):582-6.
Powers et al., Alleles of a polymorphic ETV6 binding site in DCDC2 confer risk of reading and language impairment. Am J Hum Genet. Jul. 11, 2013;93(1):19-28. doi: 10.1016/j.ajhg.2013.05.008. Epub Jun. 6, 2013.
Scerri et al., DCDC2, KIAA0319 and CMIP are associated with reading-related traits. Biol Psychiatry. Aug. 1, 2011;70(3):237-45. doi: 10.1016/j.biopsych.2011.02.005. Epub Mar. 31, 2011.
Schumacher et al., Strong genetic evidence of DCDC2 as a susceptibility gene for dyslexia. Am J Hum Genet. Jan. 2006;78(1):52-62. Epub Nov. 17, 2005.

(56) References Cited

OTHER PUBLICATIONS

Takagi et al., DNA measurements by using fluorescence correlation spectroscopy and two-color fluorescence cross correlation spectroscopy. Curr Pharm Biotechnol. Apr. 2004;5(2):199-204.

Trzaskowski et al., DNA evidence for strong genome-wide pleiotropy of cognitive and learning abilities. Behav Genet. Jul. 2013;43(4):267-73. doi: 10.1007/s10519-013-9594-x. Epub Apr. 23, 2013.

Turic et al., Linkage disequilibrium mapping provides further evidence of a gene for reading disability on chromosome 6p21.3-22. Mol Psychiatry. Feb. 2003;8(2):176-85.

Wilcke et al., Imaging genetics of FOXP2 in dyslexia. Eur J Hum Genet. Feb. 2012;20(2):224-9. doi:10.1038/ejhg.2011.160. Epub Sep. 7, 2011.

Zhong et al., Meta-analysis of the association between DCDC2 polymorphisms and risk of dyslexia. Mol Neurobiol. Feb. 2013;47(1):435-42. doi: 10.1007/s12035-012-8381-7. Epub Dec. 11, 2012.

Zou et al., Genetic variant in KIAA0319, but not in DYX1C1, is associated with risk of dyslexia: an integrated meta-analysis. Am J Med Genet B Neuropsychiatr Genet. Dec. 2012;159B(8):970-6. doi: 10.1002/ajmg.b.32102. Epub Oct. 12, 2012.

\* cited by examiner

Figure 1: High density SNP QTDT analysis.

Figure 2: LD between pairs of SNPs.

Figure 3: Haplotype TDT analyses.

Figure 4: RT-PCR results for DCDC2, MRS2L, GPLD1, ALDH5A, KIAA0319, TTRAP, THEM2, and GM.

Figure 5: In utero RNAi against DCDC2

Figure 7

Supplementary Table 1: Results of QTDT analysis with 147 SNPs

| SNP ID | SNPs | Gene | Haplo type block | DISC | IQ | PTP | TWR | PWR | WR | PD | OCH | PDL | HCH | OC | PA | ENSEMBL location | Celera location | Allele freq1 | Allele freq2 |
|---|---|---|---|---|---|---|---|---|---|---|---|---|---|---|---|---|---|---|---|
| 1 | rs1925432 | Intergene | | | | | | | | | | | | | | 23401987 | 24521300 | 0.306 | |
| 2 | rs1886705 | Intergene | | | | | | | | | | 0.0354 | | | 0.0355 | 23487330 | 24606652 | 0.481 | |
| 3 | rs1001075 | Intergene | | | 0.0406 | | | | | | | | | | | 23943737 | 25063059 | 0.327 | 0.33 |
| 4 | C_2505961 | Intergene | | | | | | | | | | 0.0607 | | | | 24080100 | 25204574 | 0.282 | 0.31 |
| 5 | C_2505937 | Intergene | | | | | | | | | | | | | | 24090597 | 25215394 | 0.250 | 0.31 |
| 6 | C_2505926 | Intergene | | | | | | | | | | | | | | 24098041 | 25222834 | 0.145 | 0.18 |
| 7 | C_2505896 | Intergene | | | 0.0924 | 0.0461 | | | | | | | | | | 24108706 | 25233474 | 0.318 | 0.4 |
| 8 | C_210230 | Intergene | | | | | | | | | | | 0.069 | | | 24136382 | 25261152 | 0.295 | 0.37 |
| 9 | C_91009 | Intergene | | | | | | | | | 0.0469 | | 0.0152 | 0.0196 | | 24177669 | 25302978 | 0.319 | 0.34 |
| 10 | C_11831124 | Intergene | | | | | | | | | | 0.0854 | | | | 24189348 | 25314657 | 0.390 | 0.46 |
| 11 | C_282670 | Intergene | | | | | 0.048 | | | | | | | | | 24198476 | 25323784 | 0.419 | 0.48 |
| 12 | C_7454493 | Intergene | | | | | | | | | | | 0.0332 | 0.0674 | | 24207349 | 25332657 | 0.271 | 0.32 |
| 13 | C_266646 | Intergene | | | | | | | | | | | | | | 24216188 | 25341496 | 0.273 | 0.26 |
| 14 | C_1809129 | Intergene | | 0.0629 | | | | | | | 0.0545 | | | | | 24220516 | 25345824 | 0.446 | 0.46 |
| 15 | C_452337 | Intergene | | | 0.0958 | | | | | | | | | | | 24227520 | 25352828 | 0.281 | 0.24 |
| 16 | C_443745 | VMP Int 2 | | | | | | | | | | 0.0925 | | | | 24239314 | 25364634 | 0.482 | 0.47 |
| 17 | C_11831186 | VMP 3'UTR | | | | | | | | | 0.035 | | | 0.0228 | | 24254651 | 25379971 | 0.217 | 0.24 |
| 18 | C_9373644 | Intergene | | | | | | | | | | | | | | 24259500 | 25384816 | 0.490 | 0.44 |
| 19 | C_3804320 | DCDC2 Int 9 | | | | | | | | | | | | | | 24285932 | 25411254 | 0.109 | |
| 20 | C_7454570 | DCDC2 Int 9 | A | | | 0.0458 | | | | | | 0.0759 | | | 0.0268 | 24286285 | 25411606 | 0.165 | 0.17 |
| 21 | rs2791971 | DCDC2 Int 8 | A | | | | | | | | | | | | | 24292952 | 25418359 | 0.248 | |
| 22 | rs2791972 | DCDC2 Int 8 | A | | | | | | | | | 0.0707 | | | | 24293222 | 25418551 | 0.208 | |
| 23 | C_113214 | DCDC2 Int 8 | A | | | | | 0.0924 | | | | | | | | 24295803 | 25421133 | 0.384 | 0.34 |
| 24 | rs3789221 | DCDC2 Int 8 | A | | | | | | | | | | | | | 24297512 | 25422843 | 0.091 | |
| 25 | rs20277584 | DCDC2 Int 8 | A | | | | | | | | | | | | | 24299475 | 25424806 | 0.063 | |
| 26 | C_7454462 | DCDC2 Int 7 | B | 0.0237 | 0.0011 | 0.0748 | | 0.0271 | | 0.0493 | 0.0173 | 0.0475 | | 0.0115 | 0.0503 | 24315179 | 25440508 | 0.255 | 0.27 |
| 27 | rs793842 | DCDC2 Int 7 | B | 0.0575 | | | | | | | | | | | | 24332467 | 25553130 | 0.345 | |
| 28 | rs793837 | DCDC2 Int 7 | | | | | | | | | | | | | | 24338193 | 25358872 | 0.173 | 0.39 |
| 29 | rs1087287 | DCDC2 Int 7 | | 0.0158 | | | | | | | | | | | | 24345269 | 25366035 | 0.273 | |
| 30 | rs793857 | DCDC2 Int 7 | | | | | | | | | | | | | | 24353401 | 25373988 | 0.075 | |
| 31 | C_7454731 | DCDC2 Int 7 | C | 0.0399 | | | | | | | | | | | | 24381770 | 25507166 | 0.283 | 0.26 |
| 32 | rs807700 | DCDC2 Int 7 | C | 0.0001 | | | | | | | | | | | | 24382384 | 25402536 | 0.276 | 0.25 |
| 33 | C_7454704 | DCDC2 Int 6 | C | | | | | | | | | | | | | 24386848 | 25512242 | 0.168 | 0.21 |

Figure 7 (continued)

| # | ID | Region | | Value | | | | | Pos1 | Pos2 | V1 | V2 |
|---|---|---|---|---|---|---|---|---|---|---|---|---|
| 34 | rs807722 | DCDC2 Int 6 | C | 0.0485 | | | | | 24387896 | 25513291 | 0.278 | 0.332 |
| 35 | rs2328208 | DCDC2 Int 6 | C | | | | | | 24393548 | 25414218 | 0.181 | |
| 36 | rs2296539 | DCDC2 Int 5 | C | 0.0234 | | | | | 24397408 | 25522804 | 0.287 | |
| 37 | C_9344981 | | | 0.0828 | | | | | 24399182 | 25524575 | 0.269 | 0.24 |
| 38 | rs707864 | DCDC2 Int 2 | C | | | | | | 24413829 | 25434513 | 0.083 | |
| 39 | rs3895346 | DCDC2 Int 2 | C | 0.081 | | | | | 24416015 | 25436667 | 0.343 | |
| 40 | C_7454814 | DCDC2 Int 2 | C | | | | | | 24418623 | 25544023 | 0.089 | 0.17 |
| 41 | rs4269365 | DCDC2 Int 2 | C | | 0.067 | | | | 24428411 | 25449084 | 0.160 | |
| | 449790 | DCDC2 Int 2 | C | 0.0275 | | | | | 24433606 | 25559004 | | |
| 42 | C_7454810 | DCDC2 Int 2 | D | 0.057 | | | | | 24444623 | 25570019 | 0.361 | 0.37 |
| 43 | rs1923168 | DCDC2 Int 2 | D | | | | | | 24447276 | 25467921 | 0.132 | |
| 44 | C_7454798 | DCDC2 Int 2 | D | 0.0264 | | | | | 24454035 | 25579430 | 0.398 | 0.39 |
| 45 | rs2753912 | DCDC2 Int 2 | D | 0.0229 | | | | | 24455603 | 25476253 | 0.404 | |
| 46 | rs6922023 | DCDC2 Int 2 | D | | | | | | 24456095 | 25476705 | 0.132 | |
| 47 | rs2100377 | DCDC2 Int 2 | E | | | | | | 24461259 | 25586655 | 0.308 | 0.32 |
| 48 | rs793719 | DCDC2 Int 1 | | | 0.0562 | | | | 24462866 | 25588261 | 0.433 | |
| 49 | C_7454790 | DCDC2 Int 1 | E | 0.00335 | | | | | 24463129 | 25588523 | 0.453 | 0.44 |
| 50 | C_2100395 | Intergene | E | 0.0508 | | | | | 24474494 | 25602930 | 0.340 | 0.34 |
| 51 | C_7466624 | Intergene | | | | | | | 24483529 | 25608967 | 0.302 | 0.35 |
| 52 | rs811103 | Intergene | | | | | | | 24490875 | 25611594 | 0.327 | |
| 53 | MRS1 | Intergene | | | | | | | 24511109 | 25636578 | 0.000 | |
| 54 | MRS2 | MRS2L 5'UTR | | | | | 0.0859 | | 24511186 | 25636655 | 0.126 | |
| 55 | MRS3 | MRS2L 5'UTR | | | | | | | | | | |
| 56 | MRS4 | | | | | | | | 24511230 | 25636699 | 0.000 | |
| 57 | MRS5 | MRS2L Ex 1 | | | | | | | 24511265 | 25636734 | 0.004 | |
| 58 | rs2295651 | | | | | | | | 24511279 | 25636748 | 0.009 | |
| | | | | | | | | | 24511367 | 25636836 | 0.005 | |
| 59 | MRS7 | | | | | | | | 24511391 | 25636860 | 0.022 | |
| 60 | MRS8 | | | | | | 0.0797 | | 24511445 | 25636914 | 0.131 | |
| 61 | rs2273606 | MRS2L In 1 | | | | | | | 24513336 | 25634071 | 0.144 | |

Figure 7 (continued)

| # | ID | Location | c1 | c2 | c3 | c4 | c5 | c6 | c7 | Pos1 | Pos2 | v1 | v2 |
|---|---|---|---|---|---|---|---|---|---|---|---|---|---|
| 62 | C_2100415 | MRS2L In 2 | | | | | | | | 24513747 | 25639203 | 0.386 | 0.31 |
| 63 | rs3761789 | MRS2L In 2 | | | | | | | | 24523169 | 25648624 | 0.129 | |
| 64 | rs1772253 | MRS2L In 5 | | | | | | | | 24528213 | 25653667 | 0.368 | |
| 65 | rs1056283 | MRS2L In 9 | 0.0932 | | | | | | | 24528355 | 25649064 | 0.427 | |
| 66 | rs13735 | MRS2L In 9 | 0.084 | | | | | | | 24531629 | 25657083 | 0.311 | |
| 67 | MRS9 | MRS2L In 10 | | | | | | | | 24531804 | 25657267 | 0.022 | |
| 68 | C_12090381 | MRS2L In 10 F | | | | | | | | 24533669 | 25659122 | 0.155 | 0.09 |
| 69 | C_9359851 | F | | | | | | 0.0246 | | 24538455 | 25663912 | 0.200 | 0.22 |
| 70 | C_9359852 | GPLD1 Int 24F | | | | | | 0.0293 | | 24538541 | 25663998 | 0.351 | 0.3 |
| 71 | C_2100442 | GPLD1 Int 24F | | | | | | 0.016 | | 24538964 | 25664417 | 0.367 | 0.3 |
| 72 | C_2100443 | GPLD1 Int 24F | | | | | | ▓ | | 24539037 | 25664490 | 0.369 | 0.3 |
| 73 | rs1042303 | | | | | | | | | 24545437 | 25670888 | 0.458 | |
| 74 | C_7454653 | GPLD1 Int 20 | | | | | | | | 24545617 | 25671067 | 0.176 | 0.17 |
| 75 | C_2100452 | GPLD1 Int 20 | | | | | | | | 24546641 | 25672091 | 0.387 | 0.44 |
| 76 | C_2100460 | GPLD1 Int 20 | | 0.025 | | 0.0731 | | | 0.0295 | 24547579 | 25673029 | 0.157 | 0.31 |
| 77 | C_2100474 | GPLD1 Int 17 | | | 0.0734 | | 0.0826 | | 0.082 | 24555828 | 25681283 | 0.301 | 0.46 |
| 78 | C_7454980 | GPLD1 Int 17 | | 0.0139 | 0.0328 | | 0.0589 | 0.0583 0.031 | 0.0103 | 24556040 | 25681495 | 0.176 | 0.18 |
| 79 | C_2100479 | GPLD1 Int 15 | | 0.0456 | 0.0932 | | 0.092 | | | 24557618 | 25683073 | 0.143 | 0.3 |
| 80 | C_2100480 | GPLD1 Int 14 | | | | | | | 0.0382 | 24558383 | 25683838 | 0.208 | 0.33 |
| 81 | C_9373740 | GPLD1 Int 13 | | | | | | | | 24564285 | 25689739 | 0.330 | 0.26 |
| 82 | C_7466744 | GPLD1 Int 10 | | | | | | | | 24574700 | 25700152 | 0.284 | 0.39 |
| 83 | C_2479643 | GPLD1 Int 3 | | | | | | | | 24587761 | 25713202 | 0.405 | 0.24 |
| 84 | C_2479645 | GPLD1 Int 3 | | | | | | | | 24587852 | 25713293 | 0.423 | 0.49 |
| 85 | C_2479663 | GPLD1 5UTR | | | | | | | | 24597720 | 25723154 | 0.305 | 0.38 |
| 86 | C_2479666 | Intergene | | | | | | | | 24599454 | 25724888 | 0.291 | 0.47 |
| 87 | C_2479683 | ALDH5A1 Int 3 | | | | | | | | 24613009 | 25738439 | 0.434 | 0.49 |
| 88 | C_15922308 | ALDH5A1 Int 4 | | | | | | | | 24622548 | 25747973 | 0.132 | |
| 89 | C_3073694 | ALDH5A1 Int 7 | | | | | | | | 24631696 | 25757124 | 0.259 | 0.3 |
| 90 | C_3073688 | ALDH5A1 Int 8 | | | | | | | | 24639429 | 25764821 | 0.441 | |

Figure 7 (continued)

| # | ID | Region | | | | | | | | | | |
|---|---|---|---|---|---|---|---|---|---|---|---|---|
| 91 | C__7466785 | ALDH5A1 3'UTR | | | | | | | | 24642172 | 25767564 | 0.336 | 0.38 |
| 92 | C__7466794 | Intergene | | | | | 0.0938 | | 0.0958 | 24652882 | 25778280 | 0.257 | 0.29 |
| 93 | C__3073676 | Intergene | | | | | | | | 24653918 | 25779316 | 0.455 | 0.48 |
| 94 | C__7466818 | | | | | | 0.065 | 0.0456 | 0.0282 | 24659643 | 25785043 | 0.168 | 0.14 |
| 95 | C__3073667 | KIAA0319 Ex 16 | | | | | 0.023 | 0.0107 | 0.011 | 24667260 | 25792651 | 0.266 | 0.23 |
| 96 | C__3073665 | KIAA0319 Int 14 | | | | | | | | 24672108 | 25797498 | 0.126 | 0.09 |
| 97 | rs2744550 | | | | | | | | | 24672524 | 25797914 | 0.005 | |
| 98 | C__3073682 | KIAA0319 Int 12 | | | | | | | | 24676372 | 25801761 | 0.486 | 0.42 |
| 99 | C__3070501 | KIAA0319 Int 8 | | | | | | | | 24686029 | 25811418 | 0.072 | 0.13 |
| 100 | C__3073656 | KIAA0319 Int 7 | | | | | | | | 24687062 | 25812451 | 0.062 | 0.13 |
| 101 | C__3073857 | KIAA0319 Int 6 | | | | 0.0874 | | | | 24688600 | 25813989 | 0.067 | |
| 102 | C__3073656 | KIAA0319 Int 5 | | | | | | | | 24690011 | 25815400 | 0.368 | 0.43 |
| 103 | C__1691926 | KIAA0319 Int 3 | | | | | | | 0.0535 | 24692345 | 25817735 | 0.332 | 0.37 |
| 104 | rs4504469 | | | | | | | | | 24696853 | 25822263 | 0.316 | |
| 105 | rs4576240 | | | | | | | | | 24704457 | 25829857 | 0.150 | |
| 106 | C__2221340 | Intergene | | | | | | | | 24740511 | 25865889 | 0.285 | 0 |
| 107 | C__2463872 | Intergene | | | | | | | | 24753399 | 25878776 | 0.303 | 0.29 |
| 108 | C__2463870 | Intergene | | | | | | | | 24753589 | 25878966 | 0.278 | 0.29 |
| 109 | C__333352 | Intergene | | | 0.0919 | | | | | 24754800 | 25880163 | 0.485 | 0.43 |
| 110 | C__16187858 | | | | | | | | | 24761252 | 25886615 | 0.041 | 0.06 |
| 111 | C__7466919 | TTRAP Ex 6 | | | | | | | | 24761355 | 25886718 | 0.240 | 0.17 |
| 112 | C__2463856 | THEM2 Int 1 | | | | | | | | 24775778 | 25901141 | 0.216 | 0.35 |

Figure 7 (continued)

| | | | | | | | | | | |
|---|---|---|---|---|---|---|---|---|---|---|
| 113 | C_7460950 | THEM2 Int 1 | 0.0888 | | | | | | | |
| 114 | C_3248054 | THEM2 Ex 2 | | 0.0485 | 0.0345 | 0.0778 | 0.046 | | 24795744 | 24806194 | 0.237 | 0.17 |
| 115 | C_3248047 | C6orf62 3UTR + | | | | | 0.0942 | | | 0.0168 | 24813814 | 25931591 | 0.333 | 0.29 |
| 116 | C_2140734 | Intergene | | | | | | | | | 24829646 | 25955042 | 0.229 | 0.23 |
| 117 | C_11830308 | Intergene G | | | 0.0807 | | | | | 0.0345 | 24872844 | 25998238 | 0.111 | |
| 118 | C_2140695 | Intergene G | | | | | | | 0.0659 | | 24898441 | 26023832 | 0.449 | 0.44 |
| 119 | C_151407 | Intergene G | | | | | | | | | 24907257 | 26032648 | 0.438 | 0.48 |
| 120 | C_11832109 | C6orf32 Int 21 ++ | | | | | | | | | 24917860 | 26043253 | 0.163 | 0.15 |
| 121 | C_152076 | C6orf32 Int 19 ++ | | | | | | | | | 24927196 | 26046513 | 0.390 | 0.34 |
| 122 | C_484656 | C6orf32 Int 18 ++ | | | | | | | | | 24935670 | 26054987 | 0.363 | 0.36 |
| 123 | C_431320 | C6orf32 Int 14 ++ | | | 0.0501 | | | 0.0816 | 0.0517 | | 24944140 | 26063457 | 0.177 | 0.16 |
| 124 | C_11834072 | C6orf32 Int 12 ++ | | | | | | | | | 24953760 | 26073072 | 0.364 | 0.3 |
| 125 | C_371663 | C6orf32 Int 7 ++ | | | | | | 0.0923 | | | 24967500 | 26086814 | 0.199 | 0.13 |
| 126 | C_11198233 | C6orf32 Int 5 ++ | | | | | | | 0.0864 | | 24976228 | 26095543 | 0.358 | 0.34 |
| 127 | C_11198237 | Intergene | | | | | | | | | 24988793 | 26108108 | 0.330 | 0.42 |
| 128 | C_15813950 | Intergene H | | | | | | | | | 25009329 | 26128646 | 0.420 | 0.49 |
| 129 | C_9360070 | Intergene H | | | | | | | | | 25016624 | 26135941 | 0.437 | 0.48 |
| 130 | C_7460841 | Intergene H | 0.0807 | 0.055 | | | | | 0.0811 | | 25022795 | 26142106 | 0.226 | 0.21 |
| 131 | C_2329908 | Intergene | | | | | | | | | 25028725 | 26148036 | 0.114 | 0.16 |
| 132 | C_2336471 | Intergene | 0.0293 | | 0.0896 | | | | | | 25039266 | 26158577 | 0.316 | 0.34 |
| 133 | C_2711470 | Intergene | | | | | 0.0604 | | | | 25055520 | 26174826 | 0.381 | 0.37 |
| 134 | C_2711477 | Intergene | 0.0622 | | | | | | | | 25058808 | 26178112 | 0.424 | 0.41 |
| 135 | C_2711487 | Intergene | | | | | | | | | 25065110 | 26184416 | 0.332 | 0.4 |
| 136 | C_2530807 | Intergene | | | | | | | | | 25081087 | 26200404 | 0.157 | 0.17 |
| 137 | C_7461306 | Intergene | | | | | 0.0114 | | | | 25088590 | 26207908 | 0.426 | 0.37 |
| 138 | C_2738571 | Intergene | | | | | | | | | 25097132 | 26216453 | 0.279 | 0.28 |
| 139 | C_9375211 | Intergene | | | | | | | | | 25112704 | 26232025 | 0.418 | 0.45 |
| 140 | C_3256976 | Intergene | | | | | | | | | 25122023 | 26241335 | 0.443 | 0.45 |
| 141 | C_3256996 | Intergene | | | | | | | | | 25135267 | 26254574 | 0.411 | 0.44 |

Figure 7 (continued)

| | | | | | | | | | |
|---|---|---|---|---|---|---|---|---|---|
| 142 | C_3248665 | Intergene | | 0.0666 | | | 25144959 | 26264249 | 0.431 | 0.39 |
| 143 | C_3248675 | Intergene | | | 0.0715 | | 25147997 | 26267287 | 0.429 | 0.45 |
| 144 | C_3248685 | Intergene | 0.0477 | | | | 25152693 | 26271984 | 0.224 | 0.19 |
| 145 | rs304257 | Intergene | | | | 0.0817 | 25159000 | 26278314 | 0.332 | 0.0921 |
| 146 | rs215013 | Intergene | | | | | 25491223 | 26612684 | 0.102 | |
| 147 | rs220698 | Intergene | 0.0301 | | | | 45915568 | 48038192 | 0.315 | |

*: Minor allele frequencies in our RD probands.
**: Minor allele frequencies in Caucasians according to Celera.
+: C6orf62 is a predicted gene in Ensembl database (Vega).
++: C6orf62 is a predicted gene in Ensembl database (Vega), and is equivalent to KIAA0386 in NCBI and Celera.
DISC, discriminant score; PTP, phoneme transposition; TWR, timed word recognition; PWR, Peabody Individual Achievement Test word recognition; WR, word recognition composite; PD, phonological decoding; OCH, orthographic choice; PDL, phoneme deletion; HCH, homonym choice; OC, orthographic choice plus homonym choice; PA, phoneme transposition plus phoneme deletion.

SNPs that change the amino acid sequence of the corresponding protein.
Single marker TDT peaks with $P < 0.01$.
SNP within the DCDC2 deletion.
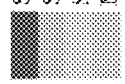 Minor allele frequency in populations other than Caucasian in the Celera database.

Figure 8

Supplementary Table 2b. Haplotype-TDT results for blocks A-H

SEQUENCE LISTING

```
<160> NUMBER OF SEQ ID NOS: 86

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
tgttgaatcc cagaccacaa                                                   20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
atcccgatga aatgaaaagg                                                   20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
agcctgccta ccacagagaa                                                   20
```

```
<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
ggaacaacct cacagaaatg g                                              21

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
tgaaaccccg tctctactga a                                              21

<210> SEQ ID NO 6
<211> LENGTH: 13
<212> TYPE: DNA
<213> ORGANISM: Homo sapiens

<400> SEQUENCE: 6
gagaggaagg aaa                                                       13

<210> SEQ ID NO 7
<211> LENGTH: 52
<212> TYPE: PRT
<213> ORGANISM: Homo sapiens

<400> SEQUENCE: 7

Met Leu Ile Phe Leu Ser Pro Arg Gly Pro His Asn Leu Leu Ile Cys
1               5                   10                  15

Cys Asn Ile Lys Thr Asp His Arg Ile Lys Met Ala Asn Val Ser Glu
                20                  25                  30

Arg Phe Tyr Leu Arg Thr Glu Glu Lys Cys Glu Glu Val Asp Ile Val
            35                  40                  45

Leu Ser His Ser
    50

<210> SEQ ID NO 8
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 8
agatcccaaa gtgtcctatt tgcat                                          25

<210> SEQ ID NO 9
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 9
gaaggaaatt tgttttaac tcagtctgga a                                    31
```

```
<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
acatttggaa atgatttt                                                       18

<210> SEQ ID NO 11
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 11
catttggaag tgatttt                                                        17

<210> SEQ ID NO 12
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 12
ttgctttcta tgggatgcaa atatacctt                                           29

<210> SEQ ID NO 13
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 13
gaaaaacaca tttagatagg tgtgtcagg                                           29

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 14
catggaggaa gtgacgtt                                                       18

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
catggaggaa atgacgtt                                                       18

<210> SEQ ID NO 16
<211> LENGTH: 24
<212> TYPE: DNA
<213> ORGANISM: Artificial sequence
<220> FEATURE:
<223> OTHER INFORMATION: Synthetic oligonucleotide
```

<400> SEQUENCE: 16
cagtagctct cagccatgta tctg                                              24

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gtgagaggct gcaggtagtg                                                   20

<210> SEQ ID NO 18
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 18
tctaaaactt gcattcttt                                                    19

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
ctaaaacttg gattcttt                                                     18

<210> SEQ ID NO 20
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 20
ccttgtgaac gcaagaagta tagtg                                             25

<210> SEQ ID NO 21
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 21
tcaaagagac caggccattt tct                                               23

<210> SEQ ID NO 22
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 22
ccctttcagt attcc                                                        15

<210> SEQ ID NO 23

```
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 23 cccttctcaat attcc                                                         15

<210> SEQ ID NO 24
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 24
cccttctctt tgagctcagc tatga                                               25

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cttggcgaca gagggaaact                                                     20

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
ccatctcaga aagttt                                                         16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
ccatctcaaa aagttt                                                         16

<210> SEQ ID NO 28
<211> LENGTH: 38
<212> TYPE: DNA
<213> ORGANISM: Artificial sequence
<220> FEATURE:
<223> OTHER INFORMATION: Synthetic oligonucleotide

<400> SEQUENCE: 28
tgtaaaacga cggccagtag cctgcctacc acagagaa                                 38

<210> SEQ ID NO 29
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 29
```

```
tcacacagga aacagctatg actgaaaccc cgtctctact gaa                43
```

<210> SEQ ID NO 30
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 30

```
tcacacagga aacagctatg acggaacaac ctcacagaaa tgg                43
```

<210> SEQ ID NO 31
<211> LENGTH: 2837
<212> TYPE: DNA
<213> ORGANISM: Homo sapiens
<220> FEATURE:
<221> NAME/KEY: misc_feature
<222> LOCATION: (379)..(379)
<223> OTHER INFORMATION: n is a, c, g, or t

<400> SEQUENCE: 31

```
agcctgccta ccacagagaa tgccttggaa tcagaggttc cctgaagaga ccctctcctc     60
ttagaataat ccaaaaccag aatctccaga gccccgtggt caaaactaaa acgttccatc    120
taggagtgag agagcacgat atctacttcc tcacacttct cctcggttct caaataaaag    180
cgctcactta catttgccat cttttattctg tgatccgttt ttatgttaca gcaaataagc    240
aaattatgag gtcctctggg cgaaaggaaa atcagcatgg aatgtaagtt attgtgccat    300
ctagagaaaa cgtgagaggc tggaagcctc matcaactgt cttccttgaa gaataaccta    360
gatcttggct cccactggnc aaagatgagt ggggggttatt gtcttctcta agaaactaaa   420
cgtccctcac atgcttgaag atgtcgcaag ggagacctga tggccccatt tctgtgaggt    480
tgttcctcaa agaagaatca agatttcag tcacattagc atcatcatgt tctcttagtc     540
cagaattttt cagcaaacat attccacaaa attttctgca agttcagggt acatatagca    600
ggtgtagtgg atttttgtta tgttttaata taacatacta gagaaaatcc agaacattct    660
tctccctctc tcttcttcat cacattcaca tctcagccta tagagcagag tttattccct    720
agtataatat caaggcctgt tttaaaaata tatatattat acatgtgaat gagaaatgag    780
tcacatttat tttaccatgt ctctggtttt taaataaaat taaaaggttg ggaaactgtt    840
tttcagtgtc acaacctctc tgttcttact accataatat ttacttgata ttatttcagt    900
tcttccttcc ccacacccat gttgaatccc agaccacaaa ctactgtaat ttttctttat    960
tattcaacat atgtaggaat gcagaattaa aattattgat caagtttcat gcaaagttcc   1020
aaaaccaaag aaagaaagaa aggaagagag gaaaaaagag agaaagacag ggagaaaaat   1080
aaaaagaagg aaagagagga aggaagaga ggaaggaaag gaaggaagga aggaaggaag    1140
gaagaaagga aggaaggaaa gaatgaagga aggaaggaag gaagggaggg aggaaatcag   1200
accttttcat ttcatcggga tacctaccac ctctctttt gactcaagct aatgttaaat    1260
gttaaaaaga gtctccattt ttagaataca ccaaccaata gaaggacccc cccatgccct    1320
agagctccct ggatagtaga aaattagtca aaaatttaaa atttactata gatgatccat   1380
aaaattaaaa atcatacaaa gcatgttaag agctgggtga catatatatt aactataaag    1440
agagcagata tagaaaggaa gccaacattt atctagcaga agaaaaaaac accatcattt   1500
gtatcaataa aaagcatgta tgatgagcgg gcatggaggc ttatgcctat aacccagcac   1560
```

| | |
|---|---:|
| tttgggaggc caaggcatgt gggtcgctta agtccaagag ttcaagacca gcctgggcaa | 1620 |
| caatggcaaa atccgtctc tactaaaagt gcaaaaaatt ggccaggtgt ggtggtacat | 1680 |
| gcctgtagtc ccagctagtc aggtggctga agcagaagga ttccctgagc ctgggagatc | 1740 |
| gaggctgaag tgagccttga tcatgctact gcactccagc ctgggtgaca gagcgagacc | 1800 |
| ctgtctcaaa aaaaaaaaa aatgcataaa aatgttcatt tacatcctca tttaacccat | 1860 |
| accatactgt attctacttg cagtatttgc taactactcc ccagatagat gggctcactt | 1920 |
| tgaggccaag gattgtgttc taccataatc tcattccttc agcacagctc agcacctggc | 1980 |
| aaattggagg caacaaatgt ctatggatcc ctctgtaacc atgaacaagt cagtcagggt | 2040 |
| acctgcactg tcaaaactta caattaactg gatagtatgt atttgatgag gggaactgaa | 2100 |
| ttacagggaa acctaggtta ggccaagtgt tgctttcgtc accaattcac agttaaggaa | 2160 |
| actgaggcca cgggccaccc agcttaggac ttttgactat aaaccctgag atctctctcc | 2220 |
| tttacataag cattttgttt tcattgctgt tgacactttg ttaatcttgc ttacttaaaa | 2280 |
| ctaatttctg ctaatagctt cagggtcttt agcaactgtc agcatgtaat gtgtctgcat | 2340 |
| ttcatatata taattagttt tcatggcaac agtccacttt tagtcaatca acattataaa | 2400 |
| gttagttatt tatttattta tttatttatt tattgactga tacggagttt tgctcttgtt | 2460 |
| gcccaggctg gagtacaagg gcccaatctt ggctcactgc aacctccgcc tcccgggttc | 2520 |
| aagcaattct cctgcctcag cctcctgagt agctgggaat tataggtgcc cgccaccaca | 2580 |
| cccggctaat ttttgtattt ttcagtagag acggggtttc accatggcag ccaggctggt | 2640 |
| ctcaaactcc tcacctcagg tgatccaact cscctcagcc tcccaaagtg ctgggattac | 2700 |
| aagtgtgagc caccgcgcct ggcaacatta taaacttata atgaatttat ggagtgttac | 2760 |
| tagtaaacaa aatgaatatt ctttaaataa aaaaatttc taaaagcctc tcaaatgtgc | 2820 |
| ttgtctttct ccttgca | 2837 |

```
<210> SEQ ID NO 32
<211> LENGTH: 2836
<212> TYPE: DNA
<213> ORGANISM: Homo sapiens

<400> SEQUENCE: 32
```

| | |
|---|---:|
| agcctgccta ccacagagaa tgccttggaa tcagaggttc cctgaagaga ccctctcctc | 60 |
| ttagaataat ccaaaaccag aatctccaga gccccgtggt caaaactaaa acgttccatc | 120 |
| taggagtgag agagcacgat atctacttcc tcacacttct cctcggttct caaataaaag | 180 |
| cgctcactta catttgccat ctttattctg tgatccgttt ttatgttaca gcaaataagc | 240 |
| aaattatgag gtcctctggg cgaaaggaaa atcagcatgg aatgtaagtt attgtgccat | 300 |
| ctagagaaaa tgtgagaggc tggaagcctc aatcaactgt cttccttgaa gaataaccta | 360 |
| gatcttggct cccactggca aagatgagtg ggggttattg tcttctctaa gaaactaaac | 420 |
| gtccctcaca tgcttgaaga tgtcgcaagg gagacctgat ggccccattt ctgtgaggtt | 480 |
| gttcctcaaa gaagaatcaa agatttcagt cacattagca tcatcatgtt ctcttagtcc | 540 |
| agaatttttc agcaaacata ttccacaaaa ttttctgcaa gttcaggggta catatagcag | 600 |
| gtgcagtgga tttttgttat gttttaatat aacatactag agaaaatcca gaacattctt | 660 |
| ctccctctct cttcttcatc acattccaat ctcagcctat agagcagagt ttattcctta | 720 |
| gtataatatc aaggcctgtt ttaaaaatat atatattata catgtgaatg agaaatgagt | 780 |
| cacatttatt ttaccatgtc tctggttttt aaataaaatt aaaaggttgg gaaactgttt | 840 |

```
ttcagtgtca caacctctct gttcttacta ccataatatt tacttgatat tatttcagtt      900
cttccttccc cacacccatg ttgaatccca gaccacaaac tactgtaatt tttctttatt      960
atcaacatat gtaggaatgc agaattaaaa ttattgatca agtttcatgc aaagttccaa     1020
aaccaaagaa agaagaaag gaagagagga aaaagagag aaagacaggg agaaaaataa       1080
aaagaaggaa agagaggaag gaagagagg aaggaaagga aggaaggaag gaaggaagga      1140
agaaaggaag gaaggaaaga atgaaggaag gaaggaagga agggagggag gaaatcagac     1200
cttttcattt catcgggata cctaccacct ctcttttga ctcaagctaa tgttaaatgt      1260
taaaaagagt ctccattttt agaatacacc aaccaataga aggaccccc catgccctag      1320 agctccctgg atagtagaaa attagtcaaa aatttaaaat ttactataga tgatccataa     1380
aattaaaaat catacaaagc atgttaagag ctgggtgaca tatatatatt aactataaag     1440
agagcagata tagaaaggaa gccaacattt atctagcaga agaaaaaaac accatcattt     1500
gtatcaataa aaagcatgta tgatgagcgg gcatggaggc ttatgcctat aacccagcac     1560
tttgggaggc cgaggcatgt gggtcgctta agtccaagag ttcaagacca gcctgggcaa     1620
caatggcaaa aatccgtctc tactaaaagt gcaaaaaatt ggccaggtgt ggtggtacat     1680
gcctgtagtc ccagctagtc aggtggctga agcagaagga ttccctgagc ctgggagatc     1740
gaggctgaag tgagccttga tcatgctact gcactccagc ctgggtgaca gagcgagacc     1800
ctgtctcaaa aaaaaaaaa aaatgcataa aaatgttcat ttacatcctc atttaaccca     1860
taccatactg tattctactt gcagtatttg ctaactactc cccagataga tgggctcact     1920
ttgaggccaa ggattgtgtt ctaccataat ctcattcctt cagcacagct cagcacctgg     1980
caaattggag gcaacaaatg tctatggatc cctctgtaac catgaacaag tcagtcaggg     2040
taactgcact gtcaaaactt acaattaact ggatagtatg tatttgatga ggggaactga     2100
attacaggga aacctaggtt aggccaagtg ttgctttcgt caccaattca cagttaagga     2160
aactgaggcc acgggccacc cagcttagga cttttgacta taaaccctga gatctctctc     2220
ccttacataa gcattttgtt ttcattgctg ttgacacttt gttaatcttg cttacttaaa     2280
actaatttct gctaatagct tcagggtctt tagcaactgt cagcatgtaa tgtgtctgca     2340
tttcatatat ataattagtt ttcatggcaa cagtccactt ttagtcaatc aacattataa     2400
acttatttat ttatttattt atttatttat ttattggctg atacggagtt ttgctcttgt     2460
tgcccaggct ggagtacaag ggcccaatct tggctcactg caacctccgc ctcccgggtt     2520
caagcaattc tcctgcctca gcctcctgag tagctgggat tataggtgcc cgccaccaca     2580
cccggctaat ttttgtattt tcagtagaga cggggtttca ccatggcagc caggctggtc     2640
tcaaactcct cacctcaggt gatccaactc gcctcagcct cccaaagtgc tgggattaca     2700
agtgtgagcc accgcgcctg gcaacattat aaacttataa tgaatttatg gagtgttact     2760
agtaaacaaa atgaatattc tttaaataaa aaaatttct aaaagcctct caaatgtgct     2820
tgtctttctc cttgca                                                    2836
```

<210> SEQ ID NO 33
<211> LENGTH: 200
<212> TYPE: DNA
<213> ORGANISM: Homo sapiens

<400> SEQUENCE: 33

```
caagtttcat gcaaagttcc aaaaccaaag aaagaaagaa aggaagagag gaaaaagag       60
```
agaaagacag ggagaaaaat aaaaagaagg aaagagagga aggaaagaga ggaaggaaag    120
gaaggaagga aggaaggaag gaagaaagga aggaaggaaa gaatgaagga aggaaggaag    180
gaagggaggg aggaaatcag                                                200

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
taaaaagaag gaaagagagg                                                 20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
cctctctttc cttctttta                                                  20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
gagaggaagg aaagagagga                                                 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
tcctctcttt ccttcctctc                                                 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gagaggaagg aaaggaagga                                                 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
tccttccttt ccttcctctc                                                 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
aaggaaggaa ggaaagaatg                                               20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
cattctttcc ttccttcctt                                               20

<210> SEQ ID NO 42
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 42
cccaccaagc aattccagac aattgtctgg aattgcttgg tggg                    44

<210> SEQ ID NO 43
<211> LENGTH: 46
<212> TYPE: DNA
<213> ORGANISM: Artificial sequence
<220> FEATURE:
<223> OTHER INFORMATION: Synthetic oligonucleotide

<400> SEQUENCE: 43
cccagtcaag gcattgaatt aaatttaatt caatgccttg actggg                  46

<210> SEQ ID NO 44
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 44 attaccctc actaaaggga tgtctagagg aatggattct gacc                     44

<210> SEQ ID NO 45
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 45
ttctaatacg actcactata gggagagcat tattcaaaag caagctgtgt              50

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 46
gtttgaatag gaaaggat                                                 18

<210> SEQ ID NO 47
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 47
attaaccctc actaaaggga tcaattatcc aatgggaaag ag                      42

<210> SEQ ID NO 48
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 48
ttctaatacg actcactata gggagacatc tctaacacag gcaggatg                48

<210> SEQ ID NO 49
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 49
gatgcaatca atggtaat                                                 18

<210> SEQ ID NO 50
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 50
attaaccctc actaaaggga ttgggtgctc cttaaaccat ttt                     43

<210> SEQ ID NO 51
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 51
ttctaatacg actcactata gggagatctg tcctttactc tttccctgaa              50

<210> SEQ ID NO 52
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 52
acctgtgcac agtttga                                                  17

<210> SEQ ID NO 53
<211> LENGTH: 43
```

```
<212> TYPE: DNA
<213> ORGANISM: Artificial sequence
<220> FEATURE:
<223> OTHER INFORMATION: Synthetic oligonucleotide

<400> SEQUENCE: 53
attaaccctc actaaaggga ttcaagaata ggggaaatgt tca                         43

<210> SEQ ID NO 54
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 54
ttctaatacg actcactata gggagatgct tccttaatgg ctgcttaac                   49

<210> SEQ ID NO 55
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 55
tggctgctta acaacccaat aaat                                              24

<210> SEQ ID NO 56
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 56
attaaccctc actaaaggga cattctgttc ttggatggag acc                         43

<210> SEQ ID NO 57
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 57
ttctaatacg actcactata gggagagaac ccaaacactt gaccaaaag                   49

<210> SEQ ID NO 58
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 58
ggagacctct gcagatacgt acta                                              24

<210> SEQ ID NO 59
<211> LENGTH: 43
<212> TYPE: DNA
<213> ORGANISM: Artificial sequence
<220> FEATURE:
<223> OTHER INFORMATION: Synthetic oligonucleotide

<400> SEQUENCE: 59
```
attaaccctc actaaaggga acttgccacc atcttttgtt gtt    43

<210> SEQ ID NO 60
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 60
ttctaatacg actcactata gggagacatg gatcttcagc attgtcaac    49

<210> SEQ ID NO 61
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 61
atcttcagca ttgtcaacct gacc    24

<210> SEQ ID NO 62
<211> LENGTH: 198
<212> TYPE: DNA
<213> ORGANISM: Homo sapiens

<400> SEQUENCE: 62
caagtttcat gcaaagttcc aaaccaagaa agaaagaaag gaagagagga aaaagagag    60 aaagacaggg agaaaaataa aaagaaggaa agagaggaag gaaagagagg aaggaaagga    120
aggaaggaag gaaggaagga agaaaggaag gaaggaaaga atgaaggaag gaaggaagga    180
agggagggag gaaatcag    198

<210> SEQ ID NO 63
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 63
cccaccaagc aattccagac aaacattgtc tggaattgct tggtggg    47

<210> SEQ ID NO 64
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 64
cccagtcaag gcattgaatt aaaacattta attcaatgcc ttgactggg    49

<210> SEQ ID NO 65
<211> LENGTH: 302
<212> TYPE: DNA
<213> ORGANISM: Artificial Sequence
<220> FEATURE:
<223> OTHER INFORMATION: Synthetic Oligonucleotide

<400> SEQUENCE: 65
tgttgaatcc cagaccacaa actactgtaa ttttctttta ttattcaaca tatgtaggaa    60
tgcagaatta aaattattga tcaagtttca tgcaaagttc caaaaccaaa gaagaaaga    120 aaggaagaga ggaaaaaaga gagaaagaca gggagaaaaa taaaaagaag gaaagagagg      180
aaggaaagag aggaaggaaa ggaaggaagg aaggaaggaa ggaagaaagg aaggaaggaa      240
agaatgaagg aaggaaggaa ggaagggagg gaggaaatca gaccttttca tttcatcggg      300
at                                                                    302

<210> SEQ ID NO 66
<211> LENGTH: 13
<212> TYPE: DNA
<213> ORGANISM: Homo sapiens

<400> SEQUENCE: 66
gagaggaagg aaa                                                         13

<210> SEQ ID NO 67
<211> LENGTH: 26
<212> TYPE: DNA
<213> ORGANISM: Homo sapiens

<400> SEQUENCE: 67
gagaggaagg aaagagagga aggaaa                                           26

<210> SEQ ID NO 68
<211> LENGTH: 16
<212> TYPE: DNA
<213> ORGANISM: Homo sapiens

<400> SEQUENCE: 68
ggaaggaagg aaggaa                                                      16

<210> SEQ ID NO 69
<211> LENGTH: 24
<212> TYPE: DNA
<213> ORGANISM: Homo sapiens

<400> SEQUENCE: 69
ggaaggaagg aaggaaggaa ggaa                                             24

<210> SEQ ID NO 70
<211> LENGTH: 28
<212> TYPE: DNA
<213> ORGANISM: Homo sapiens

<400> SEQUENCE: 70
ggaaggaagg aaggaaggaa ggaaggaa                                         28

<210> SEQ ID NO 71
<211> LENGTH: 32
<212> TYPE: DNA
<213> ORGANISM: Homo sapiens

<400> SEQUENCE: 71
ggaaggaagg aaggaaggaa ggaaggaagg aa                                    32

<210> SEQ ID NO 72
<211> LENGTH: 36
<212> TYPE: DNA
<213> ORGANISM: Homo sapiens

<400> SEQUENCE: 72
ggaaggaagg aaggaaggaa ggaaggaagg aaggaa                                36

<210> SEQ ID NO 73
<211> LENGTH: 12
<212> TYPE: DNA
<213> ORGANISM: Homo sapiens

<400> SEQUENCE: 73
ggaaggaagg aa                                                            12

<210> SEQ ID NO 74
<211> LENGTH: 16
<212> TYPE: DNA
<213> ORGANISM: Homo sapiens

<400> SEQUENCE: 74
ggaaggaagg aaggaa                                                        16

<210> SEQ ID NO 75
<211> LENGTH: 2445
<212> TYPE: DNA
<213> ORGANISM: Homo sapiens
<220> FEATURE:
<221> NAME/KEY: misc_feature
<222> LOCATION: (292)..(292)
<223> OTHER INFORMATION: n is a, c, g, or t

<400> SEQUENCE: 75
agagccccgt ggtcaaaact aaaacgttcc atctaggagt gagagagcac gatatctact         60
tcctcacact tctcctcggt tctcaaataa aagcgctcac ttacatttgc catctttatt        120
ctgtgatccg tttttatgtt acagcaaata agcaaattat gaggtcctct gggcgaaagg        180
aaaatcagca tggaatgtaa gttattgtgc catctagaga aaacgtgaga ggctggaagc        240
ctcmatcaac tgtcttcctt gaagaataac ctagatcttg gctcccactg gncaaagatg        300 agtggggtt attgtcttct ctaagaaact aaacgtccct cacatgcttg aagatgtcgc         360
aagggagacc tgatggcccc atttctgtga ggttgttcct caagaagaa tcaaagattt         420 cagtcacatt agcatcatca tgttctctta gtccagaatt tttcagcaaa catattccac        480
aaaattttct gcaagttcag ggtacatata gcaggtgtag tggattttg ttatgtttta         540 atataacata ctagagaaaa tccagaacat tcttctccct ctctcttctt catcacattc        600
acatctcagc ctatagagca gagtttattc cctagtataa atcaaggcc tgttttaaaa         660 atatatatat tatacatgtg aatgagaaat gagtcacatt tattttacca tgtctctggt        720
ttttaaataa aattaaaagg ttgggaaact gttttcagt gtcacaacct ctctgttctt         780
actaccataa tatttacttg atattattc agttcttcct tccccacacc catgttgaat         840
cccagaccac aaactactgt aattttctt tattattcaa catatgtagg aatgcagaat         900
taaaattatt gatcaagttt catgcaaagt tccaaaacca agaaagaaa gaaaggaaga         960 gaggaaaaaa gagagaaaga cagggagaaa aataaaaaga aggaaagaga ggaaggaaag       1020
agaggaagga aaggaaggaa ggaaggaagg aaggaagaaa ggaaggaagg aaagaatgaa       1080
ggaaggaagg aaggaaggga gggaggaaat cagacctttt catttcatcg ggatacctac       1140
cacctctctt tttgactcaa gctaatgtta aatgttaaaa agagtctcca tttttagaat       1200
acaccaacca atagaaggac cccccatgc cctagagctc cctggatagt agaaaattag        1260
tcaaaaattt aaaatttact atagatgatc cataaaatta aaaatcatac aaagcatgtt       1320
aagagctggg tgacatatat attaactata agagagcag atatagaaag gaagccaaca        1380
tttatctagc agaagaaaaa aacaccatca tttgtatcaa taaaaagcat gtatgatgag       1440

```
cgggcatgga ggcttatgcc tataacccag cactttggga ggccaaggca tgtgggtcgc    1500
ttaagtccaa gagttcaaga ccagcctggg caacaatggc aaaaatccgt ctctactaaa    1560
agtgcaaaaa attggccagg tgtggtggta catgcctgta gtcccagcta gtcaggtggc    1620
tgaagcagaa ggattccctg agcctgggag atcgaggctg aagtgagcct tgatcatgct    1680
actgcactcc agcctgggtg acagagcgag accctgtctc aaaaaaaaaa aaaaatgcat    1740
aaaaatgttc atttacatcc tcatttaacc cataccatac tgtattctac ttgcagtatt    1800
tgctaactac tccccagata gatgggctca ctttgaggcc aaggattgtg ttctaccata    1860
atctcattcc ttcagcacag ctcagcacct ggcaaattgg aggcaacaaa tgtctatgga    1920
tccctctgta accatgaaca agtcagtcag ggtacctgca ctgtcaaaac ttacaattaa    1980
ctggatagta tgtatttgat gaggggaact gaattacagg gaaacctagg ttaggccaag    2040
tgttgctttc gtcaccaatt cacagttaag gaaactgagg ccacgggcca cccagcttag    2100
gacttttgac tataaaccct gagatctctc tcctttacat aagcattttg ttttcattgc    2160
tgttgacact ttgttaatct tgcttactta aaactaattt ctgctaatag cttcagggtc    2220
tttagcaact gtcagcatgt aatgtgtctg catttcatat atataattag ttttcatggc    2280
aacagtccac ttttagtcaa tcaacattat aaagttagtt atttatttat ttatttattt    2340
atttattgac tgatacggag ttttgctctt gttgcccagg ctggagtaca agggcccaat    2400
cttggctcac tgcaacctcc gcctcccggg ttcaagcaat tctcc                    2445

<210> SEQ ID NO 76
<211> LENGTH: 2446
<212> TYPE: DNA
<213> ORGANISM: Homo sapiens

<400> SEQUENCE: 76
agagccccgt ggtcaaaact aaaacgttcc atctaggagt gagagagcac gatatctact      60
tcctcacact tctcctcggt tctcaaataa aagcgctcac ttacatttgc catctttatt     120
ctgtgatccg tttttatgtt acagcaaata agcaaattat gaggtcctct gggcgaaagg     180
aaaatcagca tggaatgtaa gttattgtgc catctagaga aaatgtgaga ggctggaagc     240
ctcaatcaac tgtcttcctt gaagaataac ctagatcttg ctcccactg gcaaagatga      300 gtggggtta tgtcttctc taagaaacta aacgtccctc acatgcttga agatgtcgca      360
agggagacct gatggcccca tttctgtgag gttgttcctc aaagaagaat caaagatttc     420
agtcacatta gcatcatcat gttctcttag tccagaattt tcagcaaac atattccaca     480 aaatttctg caagttcagg gtacatatag caggtgcagt ggattttgt tatgttttaa      540 tataacatac tagagaaaat ccagaacatt cttctccctc tctcttcttc atcacattca     600
catctcagcc tatagagcag agtttattcc ttagtataat atcaaggcct gttttaaaaa     660
tatatatatt atacatgtga atgagaaatg agtcacattt attttaccat gtctctggtt     720
tttaaataaa attaaaaggt tgggaaactg ttttcagtg tcacaacctc tctgttctta     780
ctaccataat atttacttga tattatttca gttcttcctt ccccacaccc atgttgaatc     840
ccagaccaca aactactgta attttctttt attatcaaca tatgtaggaa tgcagaatta     900
aaattattga tcaagtttca tgcaaagttc caaaaccaaa gaaagaaaga aaggaagaga     960
ggaaaaaaga gagaaagaca gggagaaaaa taaaaagaag gaaagagagg aaggaagaga    1020
aggaaggaaa ggaaggaagg aaggaaggaa ggaagaaagg aaggaaggaa agaatgaagg    1080
```

```
aaggaaggaa ggaagggagg gaggaaatca gacctttcca tttcatcggg atacctacca    1140
cctctctttt tgactcaagc taatgttaaa tgttaaaaag agtctccatt tttagaatac    1200
accaaccaat agaaggaccc ccccatgccc tagagctccc tggatagtag aaaattagtc    1260
aaaaatttaa aatttactat agatgatcca taaaattaaa aatcatacaa agcatgttaa    1320
gagctgggtg acatatatat attaactata aagagagcag atatagaaag gaagccaaca    1380
tttatctagc agaagaaaaa aacaccatca tttgtatcaa taaaaagcat gtatgatgag    1440
cgggcatgga ggcttatgcc tataacccag cactttggga ggccgaggca tgtgggtcgc    1500
ttaagtccaa gagttcaaga ccagcctggg caacaatggc aaaaatccgt ctctactaaa    1560
agtgcaaaaa attggccagg tgtggtggta catgcctgta gtcccagcta gtcaggtggc    1620
tgaagcagaa ggattccctg agcctgggag atcgaggctg aagtgagcct tgatcatgct    1680
actgcactcc agcctgggtg acagagcgag accctgtctc aaaaaaaaaa aaaaaatgca    1740
taaaaatgtt catttacatc ctcatttaac ccataccata ctgtattcta cttgcagtat    1800
ttgctaacta ctccccagat agatgggctc actttgaggc caaggattgt gttctaccat    1860
aatctcattc cttcagcaca gctcagcacc tggcaaattg gaggcaacaa atgtctatgg    1920
atccctctgt aaccatgaac aagtcagtca gggtaactgc actgtcaaaa cttacaatta    1980
actggatagt atgtatttga tgaggggaac tgaattacag ggaaacctag gttaggccaa    2040
gtgttgcttt cgtcaccaat tcacagttaa ggaaactgag gccacgggcc acccagctta    2100 ggactttga ctataaaccc tgagatctct ctccccttaca taagcatttt gttttcattg     2160
ctgttgacac tttgttaatc ttgcttactt aaaactaatt tctgctaata gcttcagggt    2220
ctttagcaac tgtcagcatg taatgtgtct gcatttcata tatataatta gttttcatgg    2280
caacagtcca cttttagtca atcaacatta taaacttatt tatttattta tttatttatt    2340
tatttattgg ctgatacgga gttttgctct tgttgcccag gctggagtac aagggcccaa    2400
tcttggctca ctgcaacctc cgcctcccgg gttcaagcaa ttctcc                   2446
```

<210> SEQ ID NO 77
<211> LENGTH: 86
<212> TYPE: DNA
<213> ORGANISM: Homo sapiens

<400> SEQUENCE: 77

```
gagaggaagg aaagagagga aggaaaggaa ggaaggaagg aaggaaggaa ggaaggaagg     60
aaggaaggaa ggaaggaagg aaggaa                                         86
```

<210> SEQ ID NO 78
<211> LENGTH: 73
<212> TYPE: DNA
<213> ORGANISM: Homo sapiens

<400> SEQUENCE: 78

```
gagaggaagg aaaggaagga aggaaggaag gaaggaagga aggaaggaag gaaggaagga     60
aggaaggaag gaa                                                       73
```

<210> SEQ ID NO 79
<211> LENGTH: 69
<212> TYPE: DNA
<213> ORGANISM: Homo sapiens

```
<400> SEQUENCE: 79
gagaggaagg aaaggaagga aggaaggaag gaaggaagga aggaaggaag gaaggaagga    60
aggaaggaa                                                            69

<210> SEQ ID NO 80
<211> LENGTH: 82
<212> TYPE: DNA
<213> ORGANISM: Homo sapiens

<400> SEQUENCE: 80
gagaggaagg aaagagagga aggaaaggaa ggaaggaagg aaggaaggaa ggaaggaagg    60
aaggaaggaa ggaaggaagg aa                                             82

<210> SEQ ID NO 81
<211> LENGTH: 90
<212> TYPE: DNA
<213> ORGANISM: Homo sapiens

<400> SEQUENCE: 81
gagaggaagg aaagagagga aggaaaggaa ggaaggaagg aaggaaggaa ggaaggaagg    60
aaggaaggaa ggaaggaagg aaggaaggaa                                     90

<210> SEQ ID NO 82
<211> LENGTH: 86
<212> TYPE: DNA
<213> ORGANISM: Homo sapiens

<400> SEQUENCE: 82
gagaggaagg aaagagagga aggaaaggaa ggaaggaagg aaggaaggaa ggaaggaagg    60
aaggaaggaa ggaaggaagg aaggaa                                         86

<210> SEQ ID NO 83
<211> LENGTH: 86
<212> TYPE: DNA
<213> ORGANISM: Homo sapiens

<400> SEQUENCE: 83
gagaggaagg aaagagagga aggaaaggaa ggaaggaagg aaggaaggaa ggaaggaagg    60
aaggaaggaa ggaaggaagg aaggaa                                         86

<210> SEQ ID NO 84
<211> LENGTH: 78
<212> TYPE: DNA
<213> ORGANISM: Homo sapiens

<400> SEQUENCE: 84
gagaggaagg aaagagagga aggaaaggaa ggaaggaagg aaggaaggaa ggaaggaagg    60
aaggaaggaa ggaaggaa                                                  78

<210> SEQ ID NO 85
<211> LENGTH: 73
<212> TYPE: DNA
<213> ORGANISM: Homo sapiens

<400> SEQUENCE: 85
gagaggaagg aaaggaagga aggaaggaag gaaggaagga aggaaggaag gaaggaagga    60
aggaaggaag gaa                                                       73
```

```
<210> SEQ ID NO 86
<211> LENGTH: 74
<212> TYPE: DNA
<213> ORGANISM: Homo sapiens

<400> SEQUENCE: 86
gagaggaagg aaagagagga aggaaaggaa ggaaggaagg aaggaaggaa ggaaggaagg      60
aaggaaggaa ggaa                                                       74
```

IDENTIFICATION OF GENE ASSOCIATED WITH READING DISABILITY AND USES THEREFOR

RELATED APPLICATIONS

The present application is a continuation of U.S. application Ser. No. 11/662,325 (abandoned), which is a national phase filing under 35 U.S.C. §371 of International Application No. PCT/US05/033114, filed Sep. 14, 2005, which claims the benefit of U.S. Provisional Application No. 60/610,023, filed Sep. 14, 2004, by Jeffrey R. Gruen and Haiying Meng, entitled "DCDC2 Mutations Cause Dyslexia" and U.S. Provisional Application No. 60/685,101, filed May 26, 2005, by Jeffrey R. Gruen and Haiying Meng, entitled "DCDC2 Mutations Cause Dyslexia." The referenced applications are incorporated herein in their entirety by reference. International Application PCT/US05/033114 was published under PCT Article 21(2) in English.

FUNDING

This invention was made with United States government support under grant R01 NS43530, awarded by the National Institutes of Health. The United States government has certain rights in the invention.

BACKGROUND OF THE INVENTION

Reading disability (RD), also known as developmental dyslexia and also known as dyslexia, is one of the most common of the complex neurobehavioral disorders, with prevalence rates ranging from 5 to 17 percent (1). It is characterized by an impairment of reading ability in subjects with normal intelligence and adequate educational opportunities. A range of neuroimaging studies, including diffusion tensor and functional magnetic resonance imaging, show that dyslexics have altered brain activation patterns compared to fluent readers when challenged with reading tasks (2). Partial remediation in language processing deficits results in improved reading, ameliorates disrupted function in brain regions associated with phonologic processing, and produces additional compensatory activation in other brain areas (3). These studies also implicate specific brain locations where genes integral to reading and language are expressed, and which likely are altered in RD.

Over the past 30 years clinical studies have shown that up to 50% of children of dyslexic parents, 50% of siblings of dyslexics, and 50% of parents of dyslexic children are affected (4). Estimates of heritability range from 44 to 75% (5). The first RD susceptibility region, DYX1, was reported on chromosome 15 in 1983 (6). Subsequently, loci were described on chromosomes 1, 2p15-16, 3p13, 6p (7-21), 6q, 7q32, 11, 15q21, and 18p11.2. It is still unclear which and/or how many genes contribute to RD and additional information would be useful for developing diagnostic, preventive and therapeutic approaches to this disorder.

SUMMARY OF THE INVENTION

The present invention relates to identification of a human gene, DCDC2 (MIM: 605755), associated with susceptibility for developing reading disability (RD), which is useful in identifying or aiding in identifying individuals at risk for developing RD, as well as for diagnosing or aiding in the diagnosis of RD. Forms of the DCDC2 gene that harbor variations that are associated with susceptibility for developing RD or lead to differences in RD are referred to, interchangeably, herein as DCDC2 variants, variant DCDC2 DNA or variant DCDC2 genes. As described in detail herein, Applicants identified an intronic polymorphic deletion of DCDC2 and alleles of dbSTS ID 808238 within the region that the deletion spans that are in significant disequilibrium with multiple RD traits. DCDC2 in which there is a deletion, such as the intronic polymorphic deletion described herein, and DCDC2 alleles that are associated with RD are examples of DCDC variants. The polymorphic deletion encodes tandem repeats of putative brain-related transcription factor binding sites in intron 2 of DCDC2. RT-PCR data show that DCDC2 localizes to the region of the brain where fluent reading occurs and RNAi studies show that down regulating DCDC2 leads to alteration in neuronal migration, again within the brain regions of interest. Results demonstrate that DCDC2 is a gene correlated with RD.

In summary, Applicants saturated the region of the genome around JA04, which led to the identification of an intronic polymorphic deletion of DCDC2. Alleles of dbSTS ID 808238 within the region that the deletion spans are in significant disequilibrium with multiple RD traits. RT-PCR data suggest that DCDC2 localizes to the region of the brain where fluent reading occurs and RNAi studies show that down regulating DCDC2 leads to alteration in neuronal migration, again within the brain regions of interest. Applicants' findings support the role of DCDC2 as a gene for harboring variations that lead to differences in RD.

Thus, the present invention relates to a human gene associated with susceptibility for developing RD, which is useful in identifying or aiding in identifying individuals at risk for developing RD, as well as for diagnosing or aiding in the diagnosis of RD. It also relates to methods for identifying or aiding in identifying individuals at risk for developing RD; methods for diagnosing or aiding in the diagnosis of RD; polynucleotides (e.g., probes, primers) useful in the methods; diagnostic kits containing such probes or primers; antibodies that bind wild type DCDC2 or altered DCDC2 gene product (e.g., protein); methods of treating or aiding in treating an individual at risk for or suffering from RD and compositions, such as pharmaceutical compositions, useful for treating an individual at risk for or suffering from RD; methods for determining appropriate and, preferably, optimal treatment for individuals, including response to educational interventions, curricula, written materials, tutoring, specialized classes and pharmaceuticals related to pharmacogenetics. The methods and compositions of the present invention can be used alone or in combination with other methods and compositions used for such purposes. For example, a method of diagnosing or aiding in the diagnosis of RD of the present invention can be used in conjunction with testing and behavioral assessments presently used for determining if an individual has RD. The methods of the present invention provide DNA (genetic) diagnostic tests useful in assessing RD in individuals, as well as in populations, such as the general population.

In one embodiment, the present invention provides polynucleotides useful for detecting or aiding in detecting, in a sample, a DCDC2 variant(s). A DCDC2 variant (also referred to as variant DCDC2 DNA or a variant DCDC2 gene) comprises at least one alteration in or difference from wild type DCDC2. The alteration or difference can be any nucleotide polymorphism of a coding region, exon, exon-intron boundary, signal peptide, 5-prime untranslated region, promoter region, enhancer sequence, 3-prime untranslated region or intron that is associated with RD. These polymorphisms include, but are not limited to, changes in the amino acid sequence of the proteins encoded by the DCDC2 gene, produce alternative splice products, create truncated products, introduce a premature stop codon, introduce a cryptic exon, alter the degree or expression to a greater or lesser extent, alter tissue specificity of DCDC2 expression, introduce changes in the tertiary structure of the proteins encoded by DCDC2, introduce changes in the binding affinity or specificity of the proteins expressed by DCDC2 or alter the function of the proteins encoded by DCDC2.

In another embodiment, the present invention provides methods and compositions useful for identifying or aiding in identifying individuals at risk for developing RD. In a further embodiment, the methods and compositions of the invention may be used for the treatment of an individual who has (is suffering from) RD or is at risk for developing RD. The invention also encompasses diagnostic kits for detecting, in a sample from an individual, variant DCDC2 DNA, such as a DCDC2 allele that is correlated with RD in humans. Such kits are useful in identifying or aiding in identifying individuals at risk for developing RD, as well as for diagnosing or aiding in the diagnosis of RD in an individual.

In one embodiment, the invention provides an isolated polynucleotide for the detection of a DCDC2 allele that is correlated with RD in humans, the polynucleotide comprising a nucleic acid molecule that specifically detects variant DCDC2 DNA that is correlated with the occurrence of RD in humans. Isolated polynucleotides are useful for detecting, in a sample from an individual, DCDC2 gene variants that are correlated with RD in humans. In certain embodiments, the isolated polynucleotide is a probe that hybridizes, under highly stringent conditions, to all or a portion of a DCDC2 gene that is correlated with the occurrence of RD in humans (all or a portion of a variant DCDC2 gene). In certain embodiments, the isolated probe hybridizes, under highly stringent conditions, to all or a portion of a DCDC2 gene that is associated with susceptibility for developing RD in humans but does not hybridize to a DCDC2 gene that is not associated with susceptibility for developing RD in humans. In further embodiments, the isolated polynucleotide is a primer that hybridizes, under highly stringent conditions, adjacent, upstream, or downstream to an alteration in a DCDC2 gene that is associated with susceptibility for developing RD in humans. Alternatively, polynucleotides of the present invention can be primers or probes that are useful to identify wild type DCDC2, wild type DCDC2 gene or wild type DCDC2 DNA, as defined herein. Such polynucleotides, for example, recognize or hybridize to all or a portion of wild type DCDC2, wild type DCDC2 gene or wild type DCDC2 DNA.

The polynucleotides described herein (e.g., a polynucleotide probe or a polynucleotide primer) may be a DNA or RNA molecule. The subject polynucleotide may be single-stranded or double-stranded. Polynucleotide probes and primers of the invention may be from about 5 nucleotides to about 3000 nucleotides. In certain embodiments, the polynucleotide probes and primers of the invention are from about 8 nucleotides to about 500 nucleotides. In further embodiments, the polynucleotide probes and primers of the invention are from about 10 to about 250 nucleotides, from about 10 to about 100 nucleotides, from about 10 to about 80 nucleotides, from about 10 to about 50 nucleotides, from about 10 to about 40 nucleotides, from about 10 to about 30 nucleotides, from about 10, 11, 12, 13 or 15 nucleotides to about 20, 21, 22, 23, 24 or 25 nucleotides. The subject polynucleotides may comprise one or more non-natural or modified nucleotides. Non-natural or modified nucleotides include, without limitation, radioactively, fluorescently, or chemically labeled nucleotides, and protein nucleic acids. Included within the scope of the present invention is any polynucleotide useful to identify or detect wild type or variant DCDC2 sequences. Based on the information provided herein, one of ordinary skill in the art can design and produce polynucleotide probes and primers using methods known in the art.

In one embodiment, the polynucleotide primer of the invention hybridizes vicinal to an alteration or difference (nucleotide polymorphism) in a DCDC2 gene that is associated with susceptibility for developing RD in humans. For example, hybridization may occur in such a manner that fewer than 10 nucleotides separate the alteration and the end of the hybridized primer proximal to the alteration. In specific embodiments, hybridization occurs in such a manner that 1-3 nucleotides separate the alteration and the end of the hybridized primer proximal to the alteration. In certain embodiments, the polynucleotide primer hybridizes immediately adjacent to the alteration. In another embodiment, the polynucleotide primer of the invention hybridizes upstream or downstream from an alteration in the DCDC2 gene that is correlated with the occurrence of RD in humans. For example, hybridization may occur in such a manner that the end of the hybridized primer proximal to the alteration is 10, 25, 50, 100, 250, 1000, 5000, or up to 10,000 nucleotides upstream or downstream from an alteration in the DCDC2 gene. The invention described herein also provides a pair of polynucleotide primers that specifically detect a mutation in the DCDC2 gene that is correlated with the occurrence of RD in humans, wherein the first polynucleotide primer hybridizes to one side of an alteration (e.g., one side of the deletion described herein, such as the 5-prime side) and the second polynucleotide primer hybridizes to the other side of the alteration (e.g., the other side of the deletion described herein, such as the 3 prime side). A pair of polynucleotide primers that hybridize to a region of DNA that comprises an alteration in the DCDC2 gene that is associated with susceptibility for developing RD in humans may hybridize to the region in such a manner that the ends of the hybridized primers proximal to the alteration are from about 20 to about 10,000 nucleotides apart.

Variants of the DCDC2 gene that predispose an individual to RD may be detected by the methods and compositions described herein. In particular embodiments, variant alleles, such as those depicted in Supplementary Table 3 may be detected. As used herein, the terms "wild type DCDC2", wild type DCDC2 gene" and "wild type DCDC2 DNA" refer to DNA that is not associated with susceptibility for developing RD in humans.

In certain aspects, the invention provides a method of detecting, in a sample obtained from an individual, a DCDC2 allele that is associated with susceptibility for developing RD in humans. Such a method may comprise: (a) combining the sample with a polynucleotide probe that hybridizes, under highly stringent conditions, to a DCDC2 allele that is correlated with RD in humans, but does not hybridize to a DCDC2 gene that is not associated with susceptibility for developing RD in humans and (b) determining whether hybridization occurs. The occurrence of hybridization indicates that a DCDC2 gene that is associated with susceptibility for developing RD in humans is present in the sample. Alternatively, the method may comprise: (a) combining the sample with a polynucleotide probe that uses the polymerase chain reaction to amplify, under stringent conditions, a DCDC2 allele that is associated with susceptibility for developing RD in humans, and (b) sequencing the allele, such as by conventional fluorescent tagged dideoxy terminator sequencing, wherein if the allele comprises the sequence of variant DCDC2 DNA, a DCDC2 allele that is associated with susceptibility for developing RD in humans is present in the sample.

Samples used in the methods described herein may comprise cells from the eye, epidermis, epithelium, blood, tears, saliva, mucus, urine, stool, sperm, ova, or any other tissues or bodily fluids from which sufficient DNA or RNA can be obtained. In a specific embodiment, cells obtained from a buccal swab are used. The sample should be sufficiently processed to render DNA or RNA present available for assaying in the methods described herein. For example, samples may be processed such that DNA from the sample is available for amplification by DNA polymerases or other enzymes that increase the total DNA content or for hybridization to another polynucleotide. The processed samples may be crude lysates where available DNA or RNA is not purified from other cellular material, or may be purified to specifically isolate DNA or RNA. Samples may be processed by any means known in the art that renders DNA or RNA available for assaying in the methods described herein. Methods for processing samples may include, without limitation, mechanical, chemical, enzymatic, or molecular means of lysing and/or purifying cells and cell lysates. Processing methods may include chromatographic methods such as ion exchange (e.g., cation and anion), size exclusion, affinity, and hydrophobic interaction chromatography.

In certain other aspects, the invention provides a method of detecting, in a sample obtained from an individual, a variant DCDC2 gene that is associated with susceptibility for developing RD in humans, comprising: (a) combining the sample (referred to as a test sample) with a polynucleotide probe that hybridizes, under stringent conditions, to a DCDC2 gene that is associated with susceptibility for developing RD in humans, thereby producing a combination; (b) maintaining the combination produced in step (a) under stringent hybridization conditions; and (c) comparing hybridization that occurs in the combination with hybridization in a control. The occurrence of hybridization in the combination but not in the control indicates that a DCDC2 gene that correlates with RD is present in the sample. The control is the same as the test sample and is treated the same as the test sample, except that the polynucleotide probe is one that does not bind to a DCDC2 gene that is associated with susceptibility for developing RD in humans. In all embodiments in which a control is used, the control can be assessed prior to, simultaneous with or subsequent to assessment of the test sample. For example, the control can be a previously established reference or standard. The control is typically the same type of sample as the test sample and is treated the same as the test sample, except that it is combined with a polynucleotide that does not hybridize to a DCDC2 gene that is associated with susceptibility for developing RD in humans.

In another embodiment, the invention provides a method of detecting, in a sample obtained from an individual, a DCDC2 gene that is associated with susceptibility for developing RD in humans, comprising: (a) combining a first portion of the sample with a polynucleotide probe that hybridizes, under highly stringent conditions, to a DCDC2 gene that is correlated with RD in humans, but not to a DCDC2 gene that is not correlated with RD in humans; (b) combining a second portion of the sample with a polynucleotide probe that hybridizes, under highly stringent conditions, to a DCDC2 gene that is not correlated with RD in humans, but not to a DCDC2 gene that is correlated with RD in humans; and (c) determining whether hybridization occurs. The occurrence of hybridization in the first portion but not in the second portion indicates that a gene that is correlated with RD is present in the sample.

The present invention also relates to a method of detecting, in a sample obtained from an individual, a DCDC2 gene that is associated with susceptibility for developing RD in humans, comprising: (a) combining the sample with a pair of polynucleotide primers, wherein the first polynucleotide primer hybridizes to one side of DNA (at least one nucleotide) that is present in a DCDC2 gene associated with susceptibility for developing RD but not present in a DCDC2 gene not associated with susceptibility for developing RD and the second polynucleotide primer hybridizes to the other side of DNA (at least one nucleotide) that is present in a DCDC2 gene associated with susceptibility for developing RD, but not present in a DCDC2 gene not associated with susceptibility for developing RD; (b) amplifying DNA in the sample, thereby producing amplified DNA; (c) sequencing amplified DNA; and (d) detecting in the amplified DNA the presence of DNA that is associated with susceptibility for developing RD, whereby a DCDC2 gene that is associated with susceptibility for developing RD in humans is detected. The presence of DNA that is present in a DCDC2 gene associated with susceptibility for developing RD in humans but not present in a DCDC2 gene not associated with susceptibility for developing RD indicates that a DCDC2 gene associated with susceptibility for developing RD in humans is detected in the sample. In one embodiment, one member of the pair of polynucleotide primers hybridizes to one side of DNA and the other member of the pair hybridizes to the other side of DNA in a DCDC2 gene in which there is a deletion of 2,445 bp, as described herein. The deletion is assigned breakpoints 24,433,346 and 24,435,659 (ENSEMBL database version 33 September 2005). In one embodiment, the compound STR, dbSTS BD 808238, is genotyped by sequencing PCR products generated with forward primer (TGTTGAATCCCAGACCACAA, SEQ ID NO: 1) and reverse primer (ATCCCGATGAAATGAAAAGG, SEQ ID NO: 2). In further embodiments, the members of the primer pairs each hybridize to specific sequence length variants of Repeat Units 1 through 5 and SNP1 listed in Table 3, thereby distinguishing different DCDC2 variants. For example, a primer pair could be synthesized that specifically and only identifies the presence of allele number 1 in a DNA sample; another primer pair could specifically and only identify allele number 2, and so forth. Any method known in the art for amplifying nucleic acids may be used for the methods described herein. For example, DNA in a sample may be amplified using the polymerase chain reaction, rolling circle amplification, isothermal amplification, strand displacement amplification, multiple strand displacement amplification, multiplex ligation-dependant probe amplification, allele-specific amplification, ligase chain reaction, or by other enzymatic processes. Also, any method known in the art of resolving nucleic acids may be used for the methods described herein, including but not restricted to fluorescence tagged dideoxy sequencing, single base extension, capillary electrophoresis, SNPshot, SNPlex, Invader assay, TaqMan, light-cycle real time quantitative PCR, allele-specific hybridization, restriction fragment length polymorphism, single stranded conformational polymorphisms, denaturing gradient gel electrophoresis, denaturing high-pressure liquid chromatography, oligo-hybridization, tag-arrays, dideoxy method of Sanger sequencing, MALDI-TOF, Pyrosequencing, and reverse transcriptase mediated oligonucleotide extension.

In further embodiments of the present invention useful to detect a DCDC2 gene that is correlated with RD in humans, a set of three primers is used: one universal primer that is shared between two alleles, and two primers that are each unique for each an allele. For example, the 2,445 bp deletion was genotyped by allele-specific amplification with a combination of three primers in one reaction: a universal or shared forward primer (AGCCTGCCTACCACAGAGAA, SEQ ID NO: 3), a reverse primer for non-deleted chromosomes (GGAACAACCTCACAGAAATGG, SEQ ID NO: 4), and a reverse primer for deleted chromosomes (TGAAACCCCGTCTCTACTGAA, SEQ ID NO: 5). In this embodiment, the deletion fusion fragment is 225 bp and the non-deleted fragment is 550 bp.

In other embodiments, the invention provides methods of identifying or aiding in identifying an individual at risk for developing RD. In a specific embodiment, such a method comprises assaying a sample obtained from the individual for the presence of a DCDC2 gene that is associated with susceptibility for developing RD in humans. The presence of a DCDC2 gene associated with susceptibility for developing RD indicates that the individual is at risk for developing RD.

In another specific embodiment, a method of identifying or aiding in identifying an individual at risk for developing RD comprises: (a) combining a sample obtained from the individual with a polynucleotide probe that hybridizes, under stringent conditions such as highly stringent conditions, to a DCDC2 gene that is associated with susceptibility for developing RD in humans, but does not hybridize to a DCDC2 gene that is not associated with susceptibility for developing RD in humans; and (b) determining whether hybridization occurs. The occurrence of hybridization indicates that the individual is at risk for developing RD.

In another embodiment, a method of identifying or aiding in identifying an individual at risk for developing RD, comprises: (a) obtaining DCDC2 DNA from the individual; (b) sequencing DCDC2 DNA obtained in (a); and (c) determining whether DCDC2 DNA sequenced in (b) comprises DNA (one or more nucleotides) that is present in a DCDC2 gene that is associated with susceptibility for developing RD but is not present in a DCDC2 gene not associated with susceptibility for developing RD. The presence of DNA (one or more nucleotides) that is present in a DCDC2 gene associated with susceptibility for developing RD but is not present in a DCDC2 gene not associated with susceptibility for developing RD indicates that the individual is at risk for developing RD.

In another embodiment, the invention provides diagnostic kits useful for detecting a DCDC2 gene that is associated with susceptibility for developing RD in a sample from an individual. A diagnostic kit may comprise, for example: (a) at least one container means having disposed therein a polynucleotide probe that hybridizes, under stringent conditions such as highly stringent conditions, to a DCDC2 gene that is associated with susceptibility for developing RD in humans; and (b) a label and/or instructions for the use of the diagnostic kit in the detection of such a gene in a sample.

In another aspect, a diagnostic kit useful for detecting a DCDC2 gene associated with susceptibility for developing RD in humans in a sample from an individual may comprise, for example: (a) at least one container means having disposed therein a polynucleotide primer that hybridizes to one side of DNA (at least one nucleotide) that is present in a DCDC2 gene associated with susceptibility for developing RD but not present in a DCDC2 gene not associated with susceptibility for developing RD; and (b) a label and/or instructions for the use of the diagnostic kit in the detection of a DCDC2 gene in a sample. The diagnostic kit may additionally comprise a second polynucleotide primer that hybridizes, under highly stringent conditions, to the other side of DNA (at least one nucleotide) that is present in a DCDC2 gene associated with susceptibility for developing RD, but not present in a DCDC2 gene not associated with susceptibility for developing RD.

In certain aspects, the invention provides methods and compositions for treating an individual suffering from RD. For example, if a child is assessed, as described herein, and determined to have a variant DCDC2 gene, such as a DCDC2 gene in which there is a deletion (e.g., a 2,445 bp deletion as described herein), which is associated with susceptibility for developing RD, intervention can be more effectively designed. For example, in the case of a young child shown to have the DCDC2 gene in which the deletion described herein occurs, it might be most effective not to stress reading during the first few years of school, but, rather, emphasize other skills and maintain the self esteem of the child. Alternatively, if the child does not show the occurrence of the deletion but, instead, is determined to have, for example, an allele shown in Supplementary Table 3 (e.g., allele 5 or 6), a reading program might be a more effective approach. Another approach to be considered is that of determining whether those with certain alleles, such as those in Supplementary Table 3, respond to presently used drugs, such as phenobarbitol, anti-epileptic drugs and drugs used to treat ADHD (gabaneurgic drugs, such as Ritalin), or drugs designed specifically for the purpose.

The methods and compositions described herein for treating a subject suffering from RD may be used for the prophylactic treatment of individuals who have been diagnosed or predicted to be at risk for developing RD. In this case, the composition is administered in an amount and dose that is sufficient to delay, slow, or prevent the onset of RD. Alternatively, the methods and compositions described herein may be used for the therapeutic treatment of individuals who suffer from RD. In this case, the composition is administered in an amount and dose that is sufficient to delay or slow the progression of the condition, totally or partially, or in an amount and dose that is sufficient to reverse the condition.

Antibodies, both monoclonal and polyclonal, that bind, specifically or nonspecifically, to the product of a DCDC2 gene correlated with RD are also the subject of the present invention. These may be shown to be useful for diagnostic purposes whereby the abundance of DCDC2 protein is qualitatively and/or quantitatively assessed in tissues or fluids. Typical applications include, but are not limited to, use of anti-DCDC2 antibodies in a radio-immunoassay test, or ELISA test, or western-blot analysis, among others.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1a: Evidence for transmission disequilibrium for 147 SNPs as $-\log_{10}P$ value, and plotted against position in the Ensembl human genomic reference sequence. The locations of 18 genes encoded in this region are provided. The vertical lines on the genes are cSNPs. The location of marker JA04 is shown above the gene map. The longest distance between SNPs was 332 kb located at the centromeric end of the region. The shortest distance was 14 bp in exon 1 of MRS2L. There were 20 cSNPs within exons of nine genes, and 12 non-synonymous cSNPs in five genes (DCDC2, MRS2L, GPLD1, KIAA0319 and TTRAP). The average minor allele frequency was 0.28 in the RD probands, not including the five novel private SNPs in MRS2L. FIG. 1b: $-\log_{10}P$ value for 33 SNPs (P<0.1) located within DCDC2, MRS2L, and part of GPLD1. FIG. 1c: Further expansion of a 110 kb region within DCDC2. SNPs labeled with an asterisk (*) are associated with RD phenotypes with P<0.005. C_449792 is located within the deleted 2,445 bp in intron 2 of DCDC2 and designated by a triangle (Δ). The heavy vertical black lines represent exons in DCDC2. The hatched rectangles above exons 1 and 2, and above exons 3 through 5 highlight the coding regions for the DCX double cortin peptide domains.

FIG. 2a: LD between pairs of SNPs in the 1.5 Mb region. The location of the 147 SNPs in this region are provided in Supplementary Table 1 (FIG. 7). Gene and haplotype block depictions on the top are relative to marker number and not actual physical distances. Gene and marker locations on the left are proportional to physical distances. (FIG. 2b: Triangular excerpt from lower left corner of 2a with higher resolution of SNPs 19 through 49 covering 180 kb and haplotype blocks A through E in DCDC2. Asterisks (*) indicate SNPs with P<0.005. Block A spanned five SNPs (SNPs ID: 21, 22, 23, 24, and 25) and 6.5 kb in intron 8. Block B spanned two SNPs (SNPs ID: 26 and 27) and 23 kb in intron 7 including the single marker peak at SNP 26 with IQ. Block C spanned eight SNPs (SNPs ID: 32, 33, 34, 35, 36, 37, 38, and 39) and 34.2 kb from intron 2 to intron 7, including the highest single marker peak at SNPs 33 with DISC. Block D spanned five SNPs (SNP ID: 42, 43, 44, 45, and 46) and 11.5 kb in intron 2. Block E spanned three SNPs (SNP ID: 47, 49 and 50) and 16 kb in from intron 1 to intron 2 and the 5-prime untranslated region including the single marker peak at SNP 49 with DISC. Block F spanned five SNPs (SNP ID: 68, 69, 70, 71, 72) and 5.4 kb, from MRS2L to GPLD1, including the non-synonymous cSNP in MRS2L, SNP 69. Block G spanned three SNPs (SNP ID: 117, 118, and 119) and 34.4 kb including the single marker peak at SNP 117 with PTP. Block H spanned three SNPs (SNP ID: 128, 129, and 130) and 13.5 kb including the single marker peak at SNP 130 with DISC.

FIG. 5a: Control transfection of a neutral shRNA vector and eGFP shows normal migration after four days. Most neurons have migrated well away from the ventricular surface (Vent) towards the pial surface (Pia). FIG. 5b: Neurons transfected with an shRNA vector directed against DCDC2 migrate abnormally. FIG. 5c: Cumulative probability plot of the migration distances from the ventricular surface of all transfected eGFP+cells shown in panels a and b in the two transfection conditions. Scale bar in panels a and b is 100 μm.

FIG. 7 is a table depicting the results of the QTDT analysis of 147 SNPs (Supplementary Table 1).

FIG. 8 is a table presenting the haplotype-TDT results for blocks A-H (Supplementary Table 2b).

DETAILED DESCRIPTION OF THE INVENTION

Figure 2:
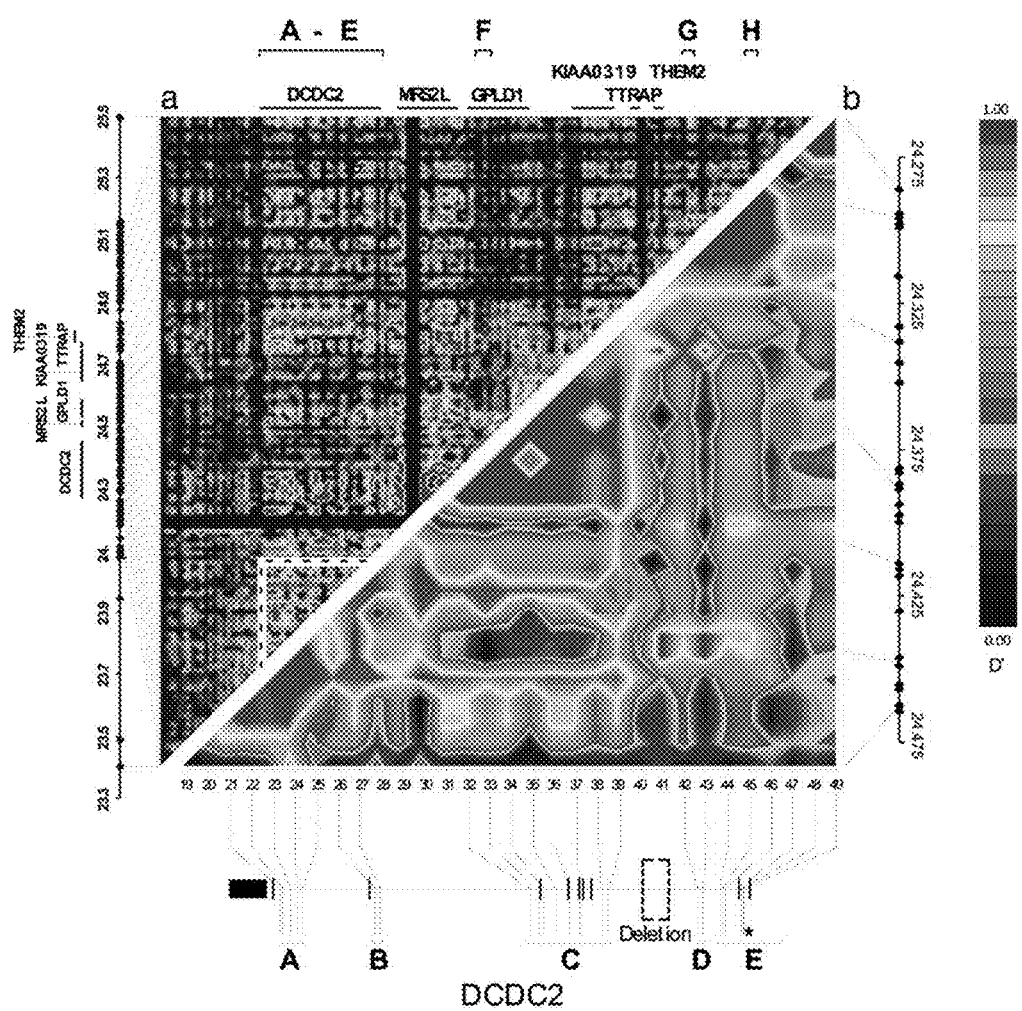
FIG. 2a-b: LD between pairs of SNPs. Color-coded D' values for pairs of SNPs are plotted with the GOLD program.

Applicants identified a novel deletion, located in intron 2 of DCDC2, which showed non-Mendelian allele transmission errors in RD families. The genotypes were confirmed by sequencing of PCR products derived from unamplified genomic DNA templates for the families. The deletion was determined to be 2,445 bp. It is, overall, 60% AT and contains a 168 bp purine-rich (98% AG) region. Within the 168 bp purine-rich region is a polymorphic compound short term repeat (STR), designated dbSTS ID 808238, which is comprised of 10 alleles that contain variable copy numbers of $(GAGAGGAAGGAAA)_n$ (SEQ ID NO: 66), $(GGAA)_n$ and $(GGGA)_n$ repeat units. Analysis identified 131 putative transcription factor binding sites distributed within the 168 bp of the purine-rich region, including four copies each of PEA3 (AGGAAA) and NF-ATp (AGGAAAG) sites in repeat unit 1 of dsSTS ID 808238. Described herein is a gene, and alleles thereof, associated with susceptibility for developing RD. Results described herein provide evidence for five linkage disequilibrium blocks (designated A to E) that span small clusters of SNPs in DCDC2 (FIG. 2b). A haplotype in each of blocks A, C, D and E (located in DCDC2) and in each of blocks F and G (located centromeric of DCDC2) was associated with compromised performance in several reading tasks in the context of preserved IQ.

Of the reported susceptibility loci, the most widely reproduced is DYX2. However, until the work described herein, only limited information was available about this gene. Reported linkage intervals range widely: 13.4 cM (16.9 Mb) spanning D6S422 (pter) through D6S291 (18), 5 cM (4.8 Mb) spanning D6S464 through D6S258 (17), and 1.8 cM (7.9 Mb) spanning D6S299 through D6S273 (16) (physical distances were previously described (14)). Applicants identified a peak of association with a short tandem repeat (STR) marker, JA04 (NCBI ID: G72384), located in the 5-prime untranslated region of KIAA0319, an uncharacterized gene that is expressed in the brain (7, 11). There are at least 19 genes and two pseudogenes encoded within 1.5 Mb of JA04; most of these are expressed in brain (22). Applicants' previous study of quantitative transmission disequilibrium test (QTDT)-association used 29 informative STR markers spanning the 10 Mb from D6S1950 through D6S478 (7, 11).

This resulted in identification of a peak of total association at JA04 (P=0.0007) with orthographic choice, which is a reading performance task that requires the rapid recognition of a target word versus a phonologically identical background foil that is not a word (i.e. rain, rane; sammon, salmon; see Olson et al, 1989 (23)).

Described herein is investigation of the DYX2 gene and corresponding alleles that create susceptibility for developing RD. To confine an association interval to the smallest possible number of candidate genes, Applicants assembled a high-density marker panel of 147 SNPs covering the 1.5 Mb surrounding JA04. This panel was used to assess single-marker and haplotype transmission disequilibrium with quantitative reading performance assessments in RD families. Quantitative expression studies of eight genes included in the panel were correlated with 18 regions of human brain corresponding to the primary functional reading centers.

As described herein, Applicants saturated the region of the genome around JA04, which led to the identification of an intronic polymorphic deletion of DCDC2. Alleles of dbSTS ID 808238 within the region that the deletion spans are in significant disequilibrium with multiple RD traits. RT-PCR data suggest that DCDC2 localizes to the region of the brain where fluent reading occurs and RNAi studies show that down regulating DCDC2 leads to alteration in neuronal migration, again within the brain regions of interest. These results show that DCDC2 is a gene harboring variation that leads to differences in RD.

Described herein is a human gene associated with susceptibility for developing RD, which is useful in identifying or aiding in identifying individuals at risk for developing RD, as well as for diagnosing or aiding in the diagnosis of RD. Also described are methods for identifying or aiding in identifying individuals at risk for developing RD; methods for diagnosing or aiding in the diagnosis of RD; polynucleotides (e.g., probes, primers) useful in the methods; diagnostic kits containing such probes or primers; antibodies that bind wild type DCDC2 or altered DCDC2 gene product (e.g., protein); methods of treating or aiding in treating an individual at risk for or suffering from RD and compositions, such as pharmaceutical compositions, useful for treating an individual at risk for or suffering from RD; methods for determining appropriate treatment for individuals, including response to educational interventions, curricula, written materials, tutoring, specialized classes and pharmaceuticals related to pharmacogenetics.

In specific embodiments, the present invention provides two DNA screening tests of the DCDC2 gene sequence that identify genetic susceptibility for developing dyslexia: a deletion assay and a DCDC2 haplotype assay spanning exons 5 through 8. These assays provide two methods of assessing the DCDC2 gene sequence to identify genetic susceptibility for developing dyslexia. Currently, there are no DNA diagnostic tests that can reliably predict susceptibility to developing reading disability, or for diagnosing reading disability, or for genetic counseling for predicting the likelihood of passing reading disability to present or future offspring. In overmore than 500 subjects and controls Applicants found the susceptibility haplotype and deletion in the same person five times, but only on the same chromosome twice. Since the two assays—deletion and haplotype—describe different mutations rarely found together, combining them will identify approximately 30% of dyslexics, as shown in Example 2 (see table entitled "Identification of dyslexics with combined deletion and (AGCTAGA) haplotype assays").

Identification of DCDC2 as DYX2 permits further interrogations of the DCDC2 gene sequence for mutations that could cause reading disability. This would involve interrogation of the coding regions of the 10 exons in the public domain (Ref Seq: NM_016356) and also putative regulatory sequences and unreported exons located within introns, the five-prime untranslated region, and the three-prime untranslated region. Both the deletion assay and haplotype assay, as described herein, can be used as a tool to screen for susceptibility to develop reading disability in the general population, as a diagnostic tool for a specific genetic subtype of reading disability, and for genetic counseling within families. These assays can also be used to test and ultimately contribute to decisions about specific forms of remediation.

Variant DCDC2 Polynucleotide Probes and Primers

In certain embodiments, the invention provides isolated and/or recombinant polynucleotides that specifically detect an alteration in a DCDC2 gene that is associated with susceptibility for developing RD (in a variant DCDC2 gene). Polynucleotide probes of the invention hybridize to the alteration of interest, and the flanking sequence, in a specific manner and thus typically have a sequence which is fully or partially complementary to the sequence of the alteration and the flanking region. A variety of alterations in a DCDC2 gene associated with susceptibility for developing RD may be detected by the polynucleotides described herein. For example, any nucleotide polymorphism of a coding region, exon, exon-intron boundary, signal peptide, 5-prime untranslated region, promoter region, enhancer sequence, 3-prime untranslated region or intron that is associated with RD can be detected. These polymorphisms include, but are not limited to, changes in the amino acid sequence of the proteins encoded by the DCDC2 gene, produce alternative splice products, create truncated products, introduce a premature stop codon, introduce a cryptic exon, alter the degree or expression to a greater or lesser extent, alter tissue specificity of DCDC2 expression, introduce changes in the tertiary structure of the proteins encoded by DCDC2, introduce changes in the binding affinity or specificity of the proteins expressed by DCDC2 or alter the function of the proteins encoded by DCDC2. In a specific embodiment, the variation in the DCDC2 gene results in a deletion of 2,445 bp, as described herein. The deletion is assigned breakpoints 24,433,346 and 24,435,659 (Ensembl). The subject polynucleotides are further understood to include polynucleotides that are variants of the polynucleotides described herein, as long as the variant polynucleotides maintain their ability to specifically detect a variation in the DCDC2 gene that is associated with susceptibility for developing RD. Variant polynucleotides may include, for example, sequences that differ by one or more nucleotide substitutions, additions or deletions.

In certain embodiments, the isolated polynucleotide is a probe that hybridizes, under stringent conditions, such as highly stringent conditions, to an alteration in the DCDC2 gene that is associated with susceptibility for developing RD. As used herein, the term "hybridization" is used in reference to the pairing of complementary nucleic acids. The term "probe" refers to a polynucleotide that is capable of hybridizing to another nucleic acid of interest. The polynucleotide may be naturally occurring, as in a purified restriction digest, or it may be produced synthetically, recombinantly or by nucleic acid amplification (e.g., PCR amplification).

It is well known in the art how to perform hybridization experiments with nucleic acid molecules. The skilled artisan is familiar with the hybridization conditions required in the present invention and understands readily that appropriate stringency conditions which promote DNA hybridization can be varied. Such hybridization conditions are referred to in standard text books such as Molecular Cloning: A Laboratory Manual, Cold Spring Harbor Laboratory (1989); and Current Protocols in Molecular Biology, eds. Ausubel et al., John Wiley & Sons: 1992. Preferred in accordance with the present invention are polynucleotides which are capable of hybridizing to a variation in the DCDC2 gene, or a region of a variant DCDC2 gene, under highly stringent conditions. By highly stringent conditions is meant that no cross-hybridization to unrelated polynucleotides occurs.

Nucleic acid hybridization is affected by such conditions as salt concentration, temperature, organic solvents, base composition, length of the complementary strands, and the number of nucleotide base mismatches between the hybridizing nucleic acids, as will readily be appreciated by those skilled in the art. Stringent temperature conditions will generally include temperatures in excess of 30° C., or may be in excess of 37° C. or 45° C. Stringent salt conditions will ordinarily be less than 1000 mM, or may be less than 500 mM or 200 mM. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6.0×SSC at room temperature followed by a wash at 2.0×SSC at room temperature. The combination of parameters, however, is much more important than the measure of any single parameter. See, e.g., Wetmur and Davidson, 1968. Probe sequences may also hybridize specifically to duplex DNA under certain conditions to form triplex or higher order DNA complexes. The preparation of such probes and suitable hybridization conditions are well known in the art. One method for obtaining DNA encoding the biosynthetic constructs disclosed herein is by assembly of synthetic oligonucleotides produced in a conventional, automated, oligonucleotide synthesizer.

A polynucleotide probe or primer used in the present invention may be labeled with any "reporter molecule," so that it is detectable in any detection system, including, but not limited to enzyme (e.g., ELISA, as well as enzyme-based histochemical assays), fluorescent, radioactive, chemical, and luminescent systems. A polynucleotide probe or primer used in the present invention may further include a quencher moiety that, when placed very close to a label (e.g., a fluorescent label), causes there to be little or no signal from the label. It is not intended that the present invention be limited to any particular detection system or label.

In another embodiment, the isolated polynucleotide of the invention is a primer that hybridizes, under highly stringent conditions, adjacent, upstream, or downstream to an alteration in DCDC2 that is associated with susceptibility for developing RD in humans. For example, a polynucleotide primer of the invention can hybridize adjacent, upstream, or downstream to an alteration in the DCDC2 gene that is associated with susceptibility for developing RD. As used herein, the term "primer" refers to a polynucleotide that is capable of acting as a point of initiation of nucleic acid synthesis when placed under conditions in which synthesis of a primer extension product that is complementary to a nucleic acid strand is induced (i.e., in the presence of nucleotides, an inducing agent such as DNA polymerase, and suitable temperature, pH, and electrolyte concentration). Alternatively, the primer may be capable of ligating to a proximal nucleic acid when placed under conditions in which ligation of two unlinked nucleic acids is induced (i.e., in the presence of a proximal nucleic acid, an inducing agent such as DNA ligase, and suitable temperature, pH, and electrolyte concentration). A polynucleotide primer of the invention may be naturally occurring, as in a purified restriction digest, or may be produced synthetically. The primer is preferably single stranded for maximum efficiency in amplification, but may alternatively be double stranded. If double stranded, the primer is first treated to separate its strands before being used. Preferably, the primer is an oligodeoxyribonucleotide. The exact lengths of the primers will depend on many factors, including temperature, source of primer and the use of the method.

In one embodiment, the invention provides a pair of primers that specifically detect an alteration in the DCDC2 gene that is associated with susceptibility for developing RD. In such a case, the first primer hybridizes upstream from the alteration and a second primer hybridizes downstream from the alteration. It is understood that one of the primers hybridizes to one strand of a region of DNA that comprises an alteration in the DCDC2 gene that is associated with susceptibility for developing RD, and the second primer hybridizes to the complementary strand of a region of DNA that comprises an alteration in the DCDC2 gene that is associated with susceptibility for developing RD. As used herein, the term "region of DNA" refers to a sub-chromosomal length of DNA. In further embodiments, the invention provides a set of three primers useful for distinguishing between two alleles of DCDC2, wherein the first allele is a non-deleted DCDC2 gene and the second allele is a deletion in the DCDC2 gene that is associated with susceptibility for RD. The first primer hybridizes to a nucleotide sequence that is common to both alleles, such as a non-allelic nucleotide sequence that is upstream or downstream of the polymorphic sequence in the DCDC2 gene. A second primer specifically hybridizes to a nucleotide sequence that is unique to a first allele (e.g., a non-deleted DCDC2 gene). A third primer specifically hybridizes to a nucleotide sequence that is unique to the second allele (e.g., a deletion in the DCDC2 gene that is associated with susceptibility for RD). The set of three primers result in the amplification of a region of DNA that is dependent on which DCDC2 allele is present in the sample. Alternatively, two primers out of the set may hybridize to a nucleotide sequence that is common to two alleles of the DCDC2 gene, such as non-allelic nucleotide sequences that are upstream and downstream of a polymorphic sequence in the DCDC2 gene, and a third primer specifically hybridizes to one of the two alleles of the DCDC2 gene.

Detection Assays

The polynucleotides of the invention may be used in any assay that permits detection of a variation in the DCDC2 gene that is associated with susceptibility for developing RD. Such methods may encompass, for example, hybridization-mediated, ligation-mediated, or primer extension-mediated methods of detection. Furthermore, any combination of these methods may be utilized in the invention.

In one embodiment, the polynucleotides of the invention detect an alteration in the DCDC2 gene that is associated with susceptibility for developing RD by amplifying a region of DNA that comprises the alteration. Any method of amplification may be used. In one specific embodiment, a region of DNA comprising the alteration is amplified by using polymerase chain reaction (PCR). PCR in particular has become a research tool of major importance with applications in cloning, analysis of genetic expression, DNA sequencing, genetic mapping, drug discovery, and the like, e.g. Arnheim et al (Ann. Rev. Biochem., 61:131-156 (1992)); Gilliland et al, Proc. Natl. Acad. Sci., 87: 2725-2729 (1990); Bevan et al, PCR Methods and Applications, 1: 222-228 (1992); Green et al, PCR Methods and Applications, 1: 77-90 (1991); Blackwell et al, Science, 250: 1104-1110 (1990). PCR refers to the method of Mullis (See e.g., U.S. Pat. Nos. 4,683,195 4,683,202, and 4,965,188, herein incorporated by reference), which describes a method for increasing the concentration of a region of DNA, in a mixture of genomic DNA, without cloning or purification. For example, the polynucleotide primers of the invention are combined with a DNA mixture (or any polynucleotide sequence that can be amplified with the polynucleotide primers of the invention), wherein the DNA comprises the DCDC2 gene. The mixture also includes the necessary amplification reagents (e.g., deoxyribonucleotide triphosphates, buffer, etc.) necessary for the thermal cycling reaction. According to standard PCR methods, the mixture undergoes a series of denaturation, primer annealing, and polymerase extension steps to amplify the region of DNA that comprises the variation in the DCDC2 gene. The length of the amplified region of DNA is determined by the relative positions of the primers with respect to each other, and therefore, this length is a controllable parameter. For example, hybridization of the primers may occur such that the ends of the primers proximal to the mutation are separated by 1 to 10,000 base pairs (e.g., 10 base pairs (bp) 50 bp, 200 bp, 500 bp, 1,000 bp, 2,500 bp, 5,000 bp, or 10,000 bp).

The invention described herein utilizes standard instrumentation for the amplification and detection of amplified DNA. For example, a wide variety of instrumentation has been developed for carrying out nucleic acid amplifications, particularly PCR, e.g. Johnson et al, U.S. Pat. No. 5,038,852 (computer-controlled thermal cycler); Wittwer et al, Nucleic Acids Research, 17: 4353-4357 (1989)(capillary tube PCR); Hallsby, U.S. Pat. No. 5,187,084 (air-based temperature control); Garner et al, Biotechniques, 14: 112-115 (1993) (high-throughput PCR in 864-well plates); Wilding et al, International application No. PCT/US93/04039 (PCR in micro-machined structures); Schnipelsky et al, European patent application No. 90301061.9 (publ. No. 0381501 A2)(disposable, single use PCR device), and the like. In certain embodiments, the invention described herein utilizes real-time PCR or other methods known in the art such as the Taqman assay.

The amplified DNA may be analyzed by several different methods. Such methods for analyzing the amplified DNA include sequencing of the DNA, determining the size of the fragment by electrophoresis or chromatography, hybridization with a labeled probe, hybridization to a DNA array or microarray, by incorporation of biotinylated primers followed by avidin-enzyme conjugate detection, or by incorporation of $^{32}$P-labeled deoxynucleotide triphosphates, such as dCTP or dATP, into the amplified segment. In one embodiment, the amplified DNA is analyzed by gel electrophoresis. Methods of gel electrophoresis are well known in the art. See for example, Current Protocols in Molecular Biology, eds. Ausubel et al., John Wiley & Sons: 1992. The amplified DNA can be visualized, for example, by fluorescent or radioactive means. The DNA may also be transferred to a solid support such as a nitrocellulose membrane and subjected to Southern Blotting following gel electrophoresis. In one aspect, the DNA is analyzed by electrophoresis and exposed to ethidium bromide and visualized under ultra-violet light.

In one aspect, the alteration in the DCDC2 gene that is associated with susceptibility for developing RD is a deletion. The deletion may be detected using any of the polynucleotide primers described herein. For example, a set of three primers may be used to distinguish between an allele of the DCDC2 gene that comprises a deletion and a wildtype DCDC2 gene. The set of three primers result in the amplification of a region of DNA that is dependent on which DCDC2 allele is present in the sample.

In another embodiment, the amplified DNA is analyzed by DNA sequencing. DNA sequence determination may be performed by standard methods such as dideoxy chain termination technology and gel-electrophoresis, or by other methods such as by pyrosequencing (Biotage AB, Uppsala, Sweden). The nucleic acid sequence of the amplified DNA can be compared to the nucleic acid sequence of wild type DNA to identify whether a variation in the DCDC2 gene that is associated with susceptibility for developing RD is present.

In another embodiment, the polynucleotides of the invention detect an alteration in the DCDC2 gene that is associated with susceptibility for developing RD by hybridization-mediated methods. In one aspect, a polynucleotide probe hybridizes to an alteration in the DCDC2 gene, and flanking nucleotides, that is associated with susceptibility for developing RD, but not to a wild type CFH gene. The polynucleotide probe may comprise nucleotides that are fluorescently, radioactively, or chemically labeled to facilitate detection of hybridization. Hybridization may be performed and detected by standard methods known in the art, such as by Northern blotting, Southern blotting, fluorescent in situ hybridization (FISH), or by hybridization to polynucleotides on a solid support (e.g., DNA arrays, microarrays, cDNA arrays, or Affymetrix chips). In one specific aspect, the polynucleotide probe is used to hybridize genomic DNA by FISH. FISH can be used, for example, in metaphase cells, to detect a deletion in genomic DNA. Genomic DNA is denatured to separate the complimentary strands within the DNA double helix structure. The polynucleotide probe of the invention is then added to the denatured genomic DNA. If an alteration in the DCDC2 gene that is associated with susceptibility for developing RD is present, the probe will hybridize to the genomic DNA. The probe signal (e.g., fluorescence) can then be detected through a fluorescent microscope for the presence of absence of signal. The absence of signal, therefore, indicates the absence of an alteration in the DCDC2 gene that is associated with susceptibility for developing RD.

Presence of signal can also be used, in another embodiment, to determine the absence of an alteration in the DCDC2 gene.

In another embodiment, the polynucleotides of the invention detect an alteration in the DCDC2 gene that is associated with susceptibility for developing RD by primer extension with DNA polymerase. In one aspect, a polynucleotide primer of the invention hybridizes immediately adjacent to the alteration. A single base sequencing reaction using labeled dideoxynucleotide terminators may be used to detect the alteration. The presence of an alteration will result in the incorporation of the labeled terminator, whereas the absence of an alteration will not result in the incorporation of the terminator. In another aspect, a polynucleotide primer of the invention hybridizes to an alteration in the DCDC2 gene that is associated with the susceptibility for developing RD. The primer, or a portion thereof, will not hybridize to a wild type DCDC2 gene. The presence of an alteration will result in primer extension, whereas the absence of an alteration will not result in primer extension. The primers and/or nucleotides may further include fluorescent, radioactive, or chemical probes. A primer labeled by primer extension may be detected by measuring the intensity of the extension product, such as by gel electrophoresis, mass spectrometry, or any other method for detecting fluorescent, radioactive, or chemical labels.

In another embodiment, the polynucleotides of the invention detect an alteration in the DCDC2 gene that is associated with susceptibility for developing RD by ligation. In one aspect, a polynucleotide primer of the invention hybridizes to a variation in the DCDC2 gene that is associated with susceptibility for developing RD. The primer, or a portion thereof will not hybridize to a wild type DCDC2 gene. A second polynucleotide that hybridizes to a region of the DCDC2 gene immediately adjacent to the first primer is also provided. One, or both, of the polynucleotide primers may be fluorescently, radioactively, or chemically labeled. Ligation of the two polynucleotide primers will occur in the presence of DNA ligase if an alteration in the DCDC2 gene that is associated with susceptibility for developing RD is present. Ligation may be detected by gel electrophoresis, mass spectrometry, or by measuring the intensity of fluorescent, radioactive, or chemical labels.

EXAMPLES

The following examples are for illustrative purposes and are not intended to be limiting in any way.

Example 1 Deletion of DCDC2 Gene Sequence

Through marker saturation studies Applicants identified a 2445 base deletion in intron 2 of DCDC2 (24,433,346 through 24,435,659 bp, in the ENSEMBL database version 33, September 2005). ORF Finder (NCBI) identifies two putative open reading frames (potential exons) within the deleted genomic sequence corresponding with 53 amino acids of putative open reading frame:

MLIFLSPRGPHNLLICCNIKTDHRIKMANVSERFYLRTEEKCEEVDI
VLSHS.

Deletions of the 2445 bases of genomic DNA from this region would also delete these amino acids. Applicants developed a PCR assay, called "DCDC2 24,433,346 through 24,435,659 Deletion Assay" (described in detail below) that specifically and unambiguously identifies persons with this deletion. In their study population of subjects recruited because they have dyslexia, this deletion is present in 17 of 108 severe dyslexics (15.7%, Table immediately below). The control population reflects the frequency of dyslexia in the general population, reportedly 5 to 15%. The deletion is present in 3 of 42 controls (7.1%). The odds of developing dyslexia in a person with this deletion are twice that of a person without the deletion.

TABLE

Allele and population frequencies of the
DCDC2 24,433,346-24,435,659 deletion

|  | Controls (1) | Dyslexia | Severe Dyslexia (2) |
|---|---|---|---|
| Allele Frequency | .036 (3/84) | .073 (28/382) | .079 (17/216) |
| Population Frequency | .071 (3/42) | .147 (28/191) | .157 (17/108) |

(1) Controls not tested and not selected for reading disability. The frequency of dyslexia in controls reflects the 5-15% frequency reported in the general population.
(2) Dyslexics that perform less than two standard deviations ($z < 2.0$) on at least one of five primary reading disability performance tests: discriminant score, phonemic awareness, phonological decoding, word recognition, or orthographic coding.

DCDC2 24,433,346 through 24,435,659 Deletion Assay

The PCR assay consists of three primers:

```
Universal Forward Primer:      AGCCTGCCTACCACAGAGAA

Deletion Reverse Primer:       TGAAACCCGTCTCTACTGAA

Non-Deletion Reverse Primer:   GGAACAACCTCACAGAAATGG
```

PCR Mixture:

| | |
|---|---|
| Shared Forward Primer | 0.3 μM |
| Deletion Reverse Primer | 0.2 μM |
| Control Reverse Primer | 0.2 μM |
| Genomic DNA Template | 5 ng |
| 10X Taq Polymerase Buffer | 1/10 volume |
| Taq Polymerase | 1 Unit |

PCR Conditions:

| | |
|---|---|
| 95° C. 15 min | Denature |
| 95° C. 30 sec | Touchdown PCR for 10 cycles |
| 65-57° C. 30 sec | drop 1° C. per cycle |
| 72° C. 60 sec | |
| 95° C. 30 sec | |
| 56° C. 30 sec | 30 cycles |
| 72° C. 60 sec | |
| 72° C. 5 min | Extension |
| 4° C. | Storage |

Gel Conditions: 1.5% agarose gel
Band Sizes:
  486 bp: no deletion
  176 bp: 2445 base deletion Example 2 A Haplotype Spanning Exons 5 Through 8 Causes Dyslexia Applicants also developed a haplotype consisting of seven markers spanning DCDC2 that is associated with dyslexia:

| DCDC2 Haplotype Assay Spanning Exons 5 Through 8 | | | | | |
|---|---|---|---|---|---|
| | Nucleotide | Origin | Location in Ensembl Database | Location in Celera Database | Location in DCDC2 |
| rs2296539 | A | NCBI | 24,397,408 | 25,522,804 | Intron 5 |
| rs2328208 | G | NCBI | 24,393,548 | 25,412,218 | Intron 5 |
| rs807722 | C | NCBI | 24,387,896 | 25,513,291 | Intron 6 |
| C_7454704_10 | T | Celera | 24,386,848 | 25,512,242 | Intron 7 |
| rs807700 | A | NCBI | 24,382,384 | 25,402,536 | Intron 7 |
| C_7454731_10 | G | Celera | 24,381,770 | 25,507,166 | Intron 7 |
| rs793857 | A | NCBI | 24,353,401 | 25,373,988 | Intron 7 |

In the study population of subjects recruited because they have dyslexia, this haplotype is present in 15 of 63 severe dyslexics (23.8%, Table immediately below). The control population reflects the frequency of dyslexia in the general population, reportedly 5 to 15%. The haplotype is present in 3 of 36 controls (8.9%). The odds of developing dyslexia in a person with this haplotype are more than twice that of a person without the haplotype.

TABLE

Haplotype and population frequencies of the DCDC2 exon 5-8 haplotype

| | Controls (1) | Dyslexia | Severe Dyslexia (2) |
|---|---|---|---|
| Haplotype Frequency | .039 (3/77) | .112 (55/491) | .118 (15/127) |
| Population Frequency | .083 (3/36) | .233 (55/236) | .238 (15/63) |

(1) Controls not tested and not selected for reading disability. The frequency of dyslexia in controls reflects the 5-15% frequency reported in the general population.
(2) Severe Dyslexics perform less than two standard deviations (z < 2.0) on at least one of five primary reading disability performance tests: discriminant score, phonemic awareness, phonological decoding, word recognition, or orthographic coding.

The haplotype assay consists of five custom markers from the NCBI dbEST database (rs2296539, rs2328208, rs807722, rs807700, rs793857) made exclusively for Applicants (Assay-by-Design®, ABI), and two proprietary markers (C_7454704_10 and C_7454731_10, Assay-on-Demand®, ABI/Celera).

Custom Markers:

```
rs2296539
rs2296539_Forward
AGATCCCAAAGTGTCCTATTTGCAT rs2296539_Reverse
GAAGGAAATTTGTTTTTAACTCAGTCTGGAA Allele specified primer 1
ACATTTGGAAATGATTTT Allele specified primer 2
CATTTGGAAGTGATTTT rs2328208
rs2328208_Forward
TTGCTTTCTATGGGATGCAAATATACCTT rs2328208_Reverse
GAAAAACACATTTAGATAGGTGTGTCAGG Allele specified primer 1
CATGGAGGAAGTGACGTT Allele specified primer 2
CATGGAGGAAATGACGTT
```

```
rs807722
rs807722_Forward
CAGTAGCTCTCAGCCATGTATCTG rs807722_Reverse
GTGAGAGGCTGCAGGTAGTG Allele specified primer 1
TCTAAAACTTGCATTCTTT Allele specified primer 2
CTAAAACTTGGATTCTTT rs807700
rs807700_Forward
CCTTGTGAACGCAAGAAGTATAGTG rs_07700_Reverse
TCAAAGAGACCAGGCCATTTTCT Allele specified primer 1
CCCTTTCAGTATTCC Allele specified primer 2
CCCTTTCAATATTCC rs793857
rs793857_Forward
CCCTTTCTTTTGAGCTCAGCTATGA rs793857_Reverse
CTTGGCGACAGAGGGAAACT Allele specified primer 1
CCATCTCAGAAAGTTT Allele specified primer 2
CCATCTCAAAAAGTTT
```

PCR Mixture:

| 40X Assay mix of primers | 0.1 μl |
|---|---|
| Genomic DNA Template | 1.6 ng |
| 2X ABI Universal PCR Mix | 1.0 μl |
| Water | 0.1 μl |

PCR Conditions:

| 95° C. 10 min | Denature |
|---|---|
| 92° C. 15 sec | |
| 60° C. 60 sec | 60 cycles |
| 4° C. | Storage |

Allele Resolution:
 ABI Prism 7900HT Sequence Detection System
 ABI Prism 7900HT standard protocol for ABI TaqMan markers

TABLE

Identification of dyslexics with combined deletion and (AGCTAGA) haplotype assays.

|  | Controls (1) | Dyslexia (2) | Severe Dyslexia (3) |
|---|---|---|---|
| Population Frequency | .119 (5/42) | .331 (78/236) | .296 (32/108) |

(1) Controls not tested and not selected for reading disability. The frequency of dyslexia in controls reflects the 5-15% frequency reported in the general population.
(2) The deletion and associated haplotype were found together in five dyslexic subjects, twice on the same chromosome.
(3) Severe Dyslexics perform less than two standard deviations ($z < 2.0$) on at least one of five primary reading disability performance tests: discriminant score, phonemic awareness, phonological decoding, word recognition, or orthographic coding.

Example 3 Single-Marker Transmission Disequilibrium

Figure 1:
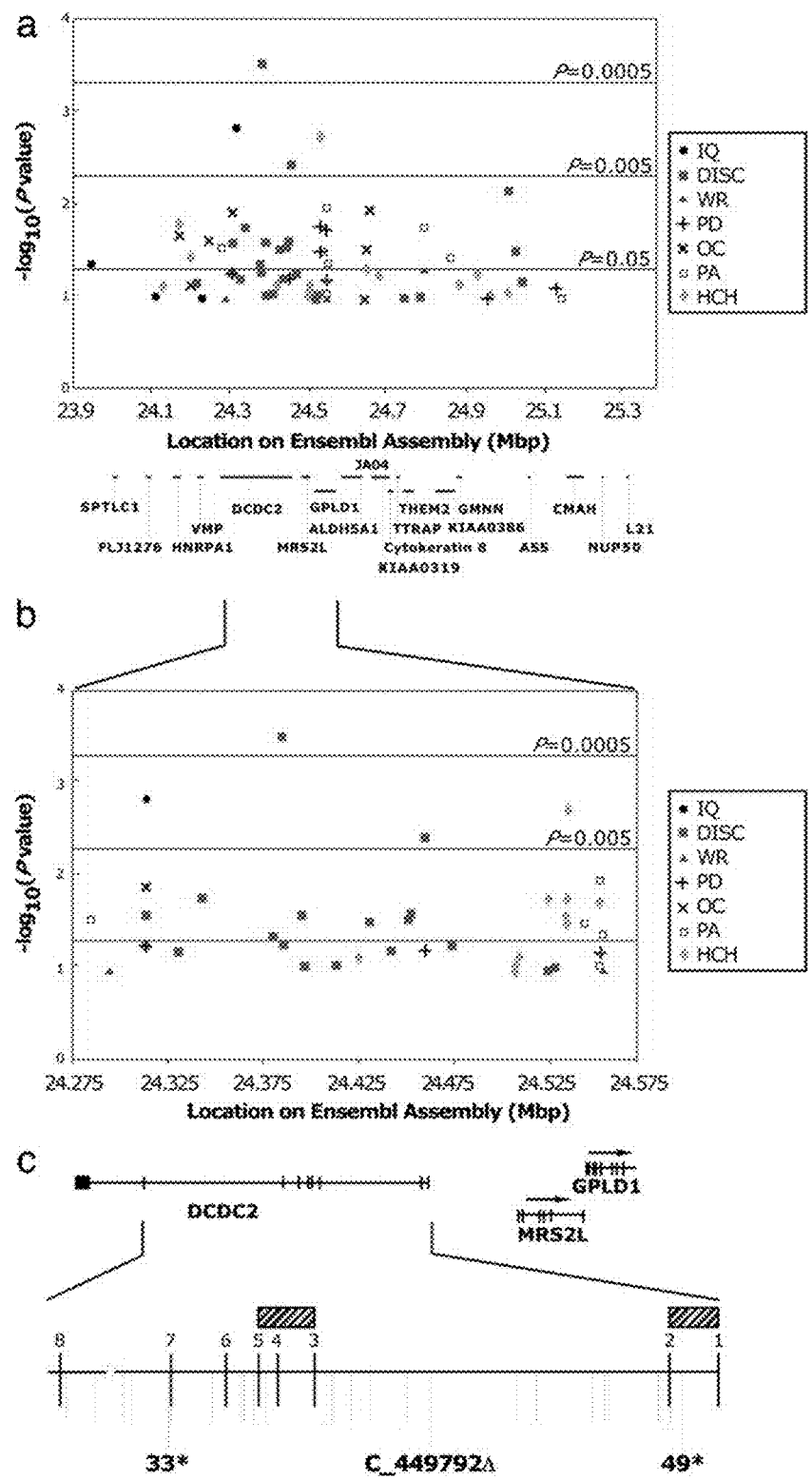
FIG. 1a-1c: High density SNP QTDT analysis.

Applicants genotyped a total of 147 SNPs distributed through the 1.5 Mb region surrounding JA04 in 153 nuclear RD families recruited by the Colorado Learning Disabilities Research Center (CLDRC). The strongest QTDT peak was with the DISC phenotype and SNP 33 located in intron 6 of DCDC2 (P=0.0003). Table 1 and FIG. 1 provide the results from a selected subset of the most significant QTDT scores. Results for the entire SNP panel can be found in Supplementary Table 1 (FIG. 7).

Five SNPs yielded a P value of ≤0.01; two of these were located in DCDC2. Thirty-seven SNPs yielded a P value of ≤0.05; eleven of these were located in DCDC2. Of the 31 SNPs distributed through DCDC2 (average minor allele frequency=0.24), ten were associated with the DISC phenotype (P≤0.05).

Example 4 Intermarker Linkage Disequilibrium

Applicants constructed an intermarker linkage disequilibrium map (FIG. 2a) spanning the 1.5 Mb with graphical overview of linkage disequilibrium (GOLD) and Haploview. There was evidence for five linkage disequilibrium blocks (A to E) spanning small clusters of SNPs in DCDC2 (FIG. 2b). There were three blocks (F to H) centromeric of DCDC2 that corresponded to single marker QTDT peaks.

Example 5 Haplotype Transmission Disequilibrium

Figure 3:
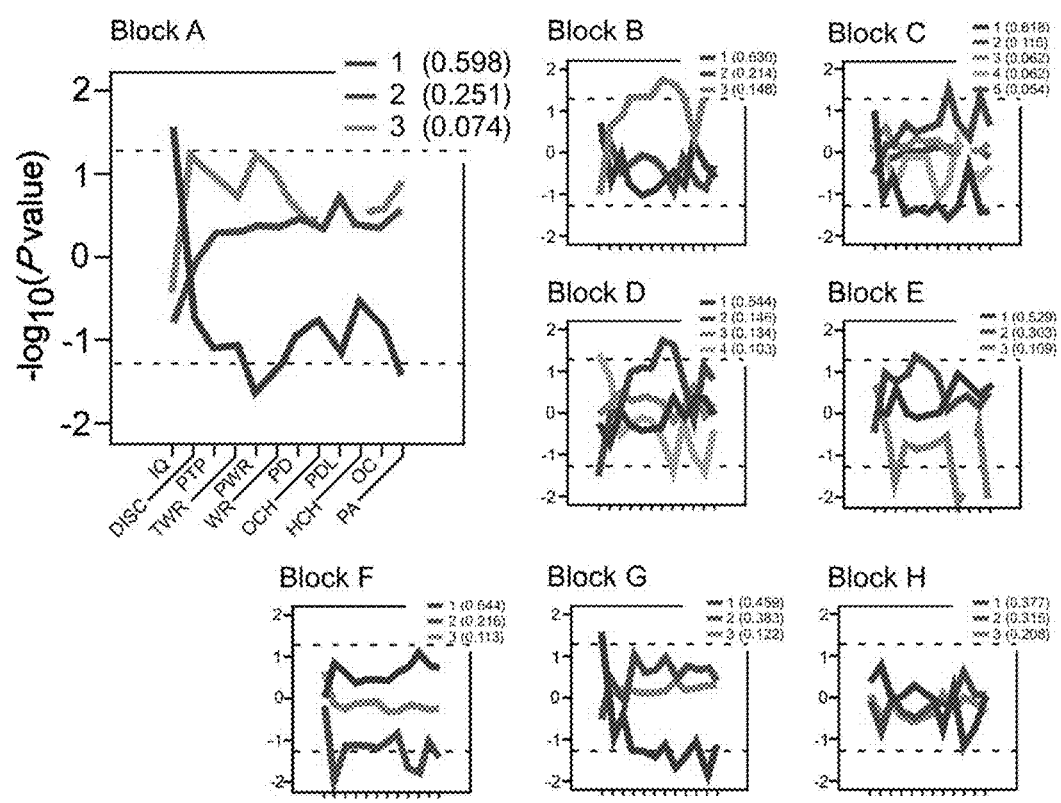
FIG. 3: Haplotype-TDT analyses. FBAT results for 12 cognitive phenotypes at haplotype blocks A through H. The locations of the haplotype blocks are presented in FIG. 2. The markers comprising each haplotype block are described in the legend for FIG. 2 and Supplementary Tables 1 and 2a. Evidence for transmission disequilibrium is plotted as $-\log_{10}P$ along the y-axis, for each phenotype represented by tick marks along the x-axis from left to right as: IQ, DISC, PTP, TWR, PWR, WR, PD, OCH, PDL, HCH, OC, and PA. Positive or negative values for $-\log_{10}P$ value reflect the direction of the z-score derived by FBAT, so that z-scores below the population mean are plotted as $-\log_{10}P$ value <0, and visa versa. Dashed lines represent P value <0.5. Haplotypes within each block are numbered 1 through 5 and are represented by different colors. The alleles that define each haplotype are presented in Supplementary Table 2a. Frequencies of each haplotype in the CLDRC cohort are presented in the legend. Blocks A through E span DCDC2.
Figure 8:
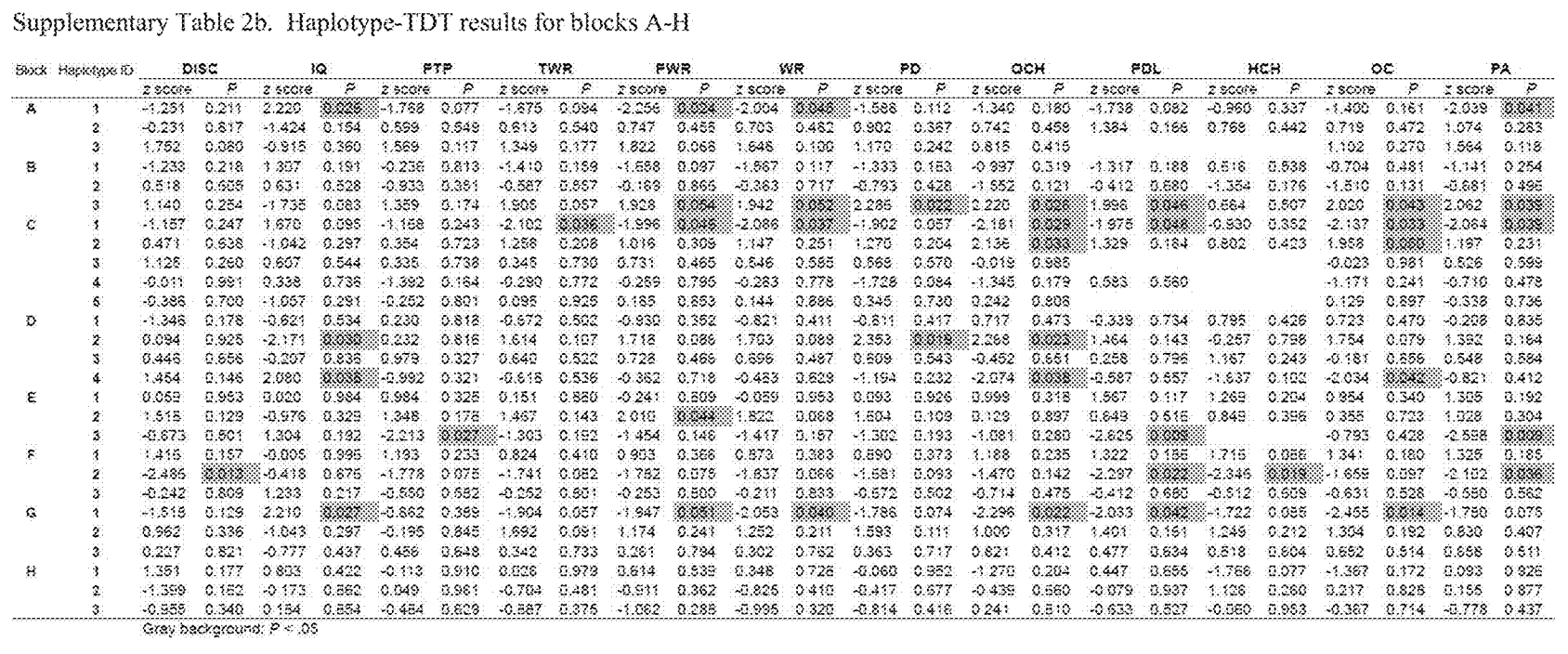

All five haplotype blocks in DCDC2 showed significant transmission disequilibrium with reading performance tasks; three of these, A, B, and D, did not contain single marker QTDT peaks. FIG. 3 is a graphic presentation of the haplotype transmission disequilibrium data, which is also provided in tabular form in Supplementary Tables 2a and 2b (FIG. 8). A haplotype in each of blocks A, C, D, E, F, and G was associated with compromised performance in several reading tasks in the context of preserved IQ. Haplotype blocks A, C, D, and E were located in DCDC2. There were no haplotypes in block H that showed significant association with any of the cognitive phenotypes.

Example 6 Identification of a Novel Deletion in DCDC2

C_449792, located in intron 2 of DCDC2 (FIG. 1), showed non-Mendelian allele transmission errors in ten RD families. To ensure that this was not an artifact of whole genome amplification, Applicants confirmed these initial genotypes by sequencing PCR products derived from unamplified genomic DNA templates for all ten families. Allele transmission from the two flanking SNPs, 41 and 42, were typically Mendelian and defined initially the outer boundaries of a 17 kb region with loss-of-heterozygosity (LOH). To identify the extent of the deletion Applicants interrogated for LOH by sequencing SNPs within the 17 kb genomic region in RD trios. Additional flanking SNPs limited the deletion to 3,848 bp. Finally Applicants amplified and sequenced a 1,200 bp fusion fragment in subjects with LOH, which assigned the breakpoints to 24,433,346 and 24,435,659 (ENSEMBL database version 33 September 2005, FIG. 2). Primer walking was used to sequence the non-deleted fragment from the same subjects with LOH. These results confined the deletion to 2,445 bp. Overall, the deletion was 60% AT, and contained a 168 bp purine-rich (98% AG) region.

Example 7 Identification of a Compound STR in the Deletion in DCDC2

Within the 168 bp purine-rich region was a polymorphic compound STR (dbSTS ID 808238) comprised of 11 alleles containing variable copy numbers of $(GAGAG-GAAGGAAA)_n$ (SEQ ID NO: 66), $(GGAA)_n$, and $(GGGA)_n$ repeat units (Supplementary Table 3). In the CLDRC cohort, some alleles were present only in the parents (five) and others—including the deletion—occurred too infrequently in probands to compute transmission disequilibrium. By combining the deletion and ten minor alleles, QTDT showed a peak of transmission disequilibrium with homonym choice (HCH; P=0.00002, Table 2). TESS (24) comparison to the TRANSFAC database identified 131 putative transcription factor binding sites distributed through the 168 bp of the purine-rich region, including four copies each of PEA3 (AGGAAA) and NF-ATp (AGGAAAG) sites in repeat unit 1 of dbSTS ID 808238. Both transcription factors are expressed in mouse brain. PEA3 is associated with sexual function and peripheral motor neuron arborization (25). NF-ATp mediates rapid embryonic axon extension necessary for forming neuronal connections (26), which would complement the putative function of the doublecortin peptide domains in DCDC2.

Figure 4:
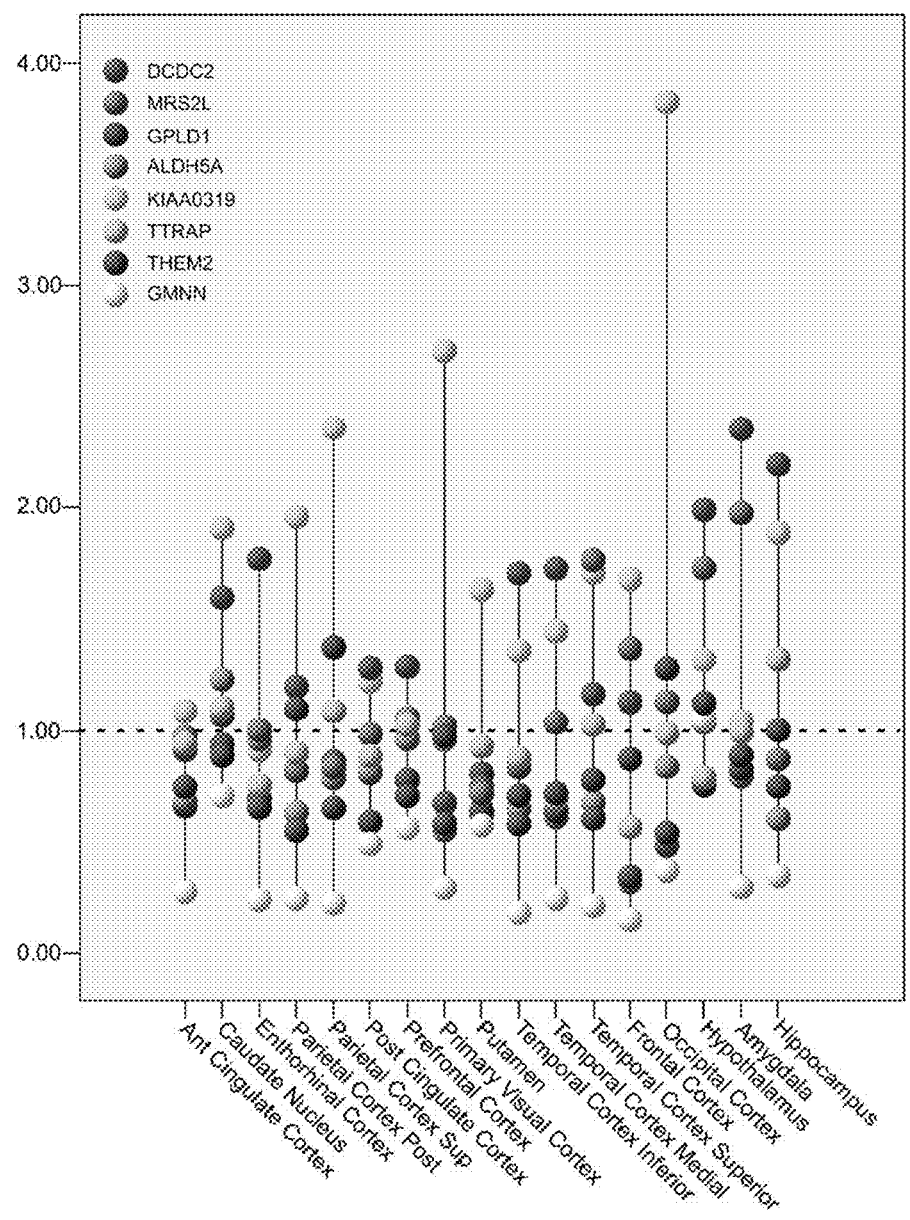
FIG. 4: RT-PCR results for DCDC2, MRS2L, GPLD1, ALDH5A, KIAA0319, TTRAP, THEM2, and GMN, in 17 areas of anonymous donor human brain regions normalized to thalamus (=1.00).

Example 8 Assessment of Expression Levels of Genes in Human Brain Using Quantitative Real Time RT-PCR FIG. 4 shows the expression levels of eight genes in 17 regions of human brain normalized to thalamus by quantitative real time RT-PCR; thalamus is a region of the brain that has not consistently been implicated in reading. The most variably expressed genes were KIAA0319, MRS2L, and DCDC2. KIAA0319 was most highly expressed in the superior parietal cortex, primary visual cortex, and occipital cortex. MRS2L was most highly expressed in the superior temporal cortex, hypothalamus, and amygdala. DCDC2 was most highly expressed in the entorhinal cortex, inferior temporal cortex, medial temporal cortex, hypothalamus, amygdala, and hippocampus. Expression of TTRAP, THEM2, Geminin, and ALDH5A in the 17 regions of the brain did not differ significantly from thalamus.

Example 9 Determination of a Role for DCDC2

Figure 5:
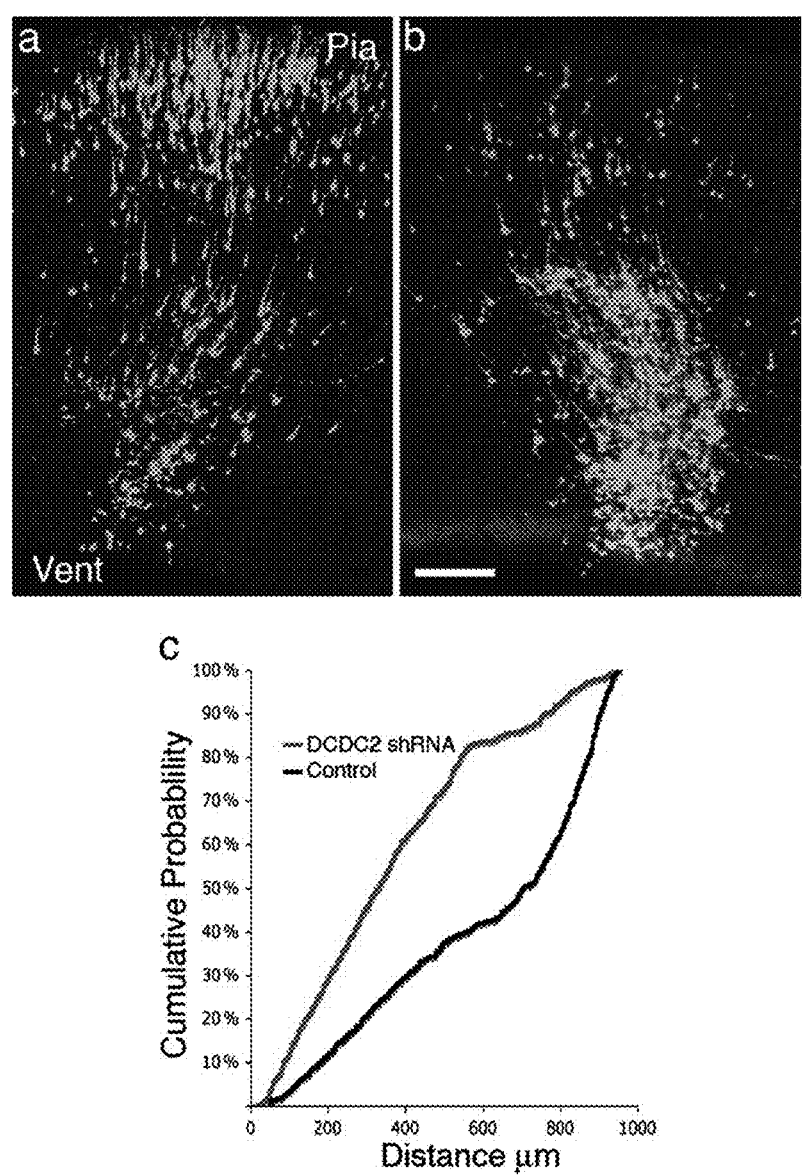
FIG. 5a-c: In utero RNAi against DCDC2.

In utero RNAi was used to test for a functional role of DCDC2 in neuronal migration. Co-transfection of plasmid vectors encoding shRNA targeted against DCDC2 sequence in developing neocortex or control scrabbled sequence along with an eGFP expression plasmid was performed at gestational day 14 in the rat. This transfection method initially labeled approximately 1% of cells at the surface of the ventricles where new neurons undergo their terminal mitoses. Cells migrate from this surface to the pial surface in four to six days. We assessed the progress in migration four days following transfection for the two conditions. As shown in FIG. 5, cells transfected with control plasmids progressed significantly further away from the ventricular surface and towards the pial surface than did cells transfected with a vector targeted against DCDC2. The mean migration distance in matched littermate controls was 606+178 μm and in the DCDC2 shRNA transfection group the mean migration distance was 367 μm+135 (n=4, p<0.01).

Example 10 Annotation of Deletion Sequence

Gruenlab Reference Sequence

SOURCE: Gruenlab reference sequence compiled from ABI files generated Jan. 10, 2005 through Jan. 21, 2005, from a single sub-clone of genomic DNA from a single subject, NA10848 (CEPH Family 1332). NA10848 DNA was purchased from the Coriel Institute (Camden, N.J.).

Annotations:

```
Location: Intron 2 of DCDC2 (MIM: 605755)

Length: 2,837 bases in length

Direction: pter to cen on 6 p

Base #1 corresponds to base number 21,571 in clone

RP11-95P3 in the NCBI database (http://www.ncbi.nlm.nih.gov/).

Base #1 corresponds to base number 24,433,259 in

ENSEMBL v33-September 2005

(http://www.ensembl.org/Multi/blastview).

Deletion breakpoints: between base #87-88 (pter)

between base #2,532-2,533

(cen)

Flanking sequence: base 1 through base 87 (pter)

base 2,533 through base 2,837

(cen)

Deletion range: 2,445 bases

Deletion primers:

Del_F primer: 5'- tgt aaa acg acg gcc agt
AGCCTGCCTACCACAGAGAA -3' base #1 - 20 (5-prime to 3-prime)

(lower case sequence is M13-Forward)

Del_R primer: 5'- tca cac agg aaa cag cta tga c
TGAAACCCCGTCTCTACTGAA -3' base #2,621-2,601 (5-prime to 3-prime)

(lower case sequence is M13-Reverse)

Del_C primer: 5'- tca cac agg aaa cag cta tga c
GGAACAACCTCACAGAAATGG -3' base #486-466 (5-prime to 3-prime)

(lower case sequence is M13-Reverse)

Deletion amplicon, Del_F through Del_R size: 216 bases (including the M13F and M13R ends)

Non-deletion amplicon, Del_F through Del_C size: 526 bases (including the M13F and M13R ends)

Purine-rich region: 170 bp (1,027 through 1,196)

Compound Short Tandem Repeat, dbSTS ID 808238

(base 1,094 through 1,191)

Repeat Unit 1: (GAGAGGAAGGAAA)n (start base 1,094)

Repeat Unit 2: (GGAA)n (start base 1,120)

SNP1: DeLGAAA (start base 1,144)

Repeat Unit 3: (GGAA)n (start base 1,148)

Repeat Unit 4: (GGAA)n (start base 1,168)

Repeat Unit 5: (GGGA)n (start base 1,184)
```

Comparison of Gruenlab Reference to NCBI Sequence:

|  | 311 | 331 | 379 | 719 | 964 | 1430 | 1572 | 1823 |
|---|---|---|---|---|---|---|---|---|
| Gruenlab | C | M | N | C | T | — | A | — |
| NCBI | T | A | — | T | — | AT | G | A |

|  | 2042 | 2221 | 2401 | 2405 | 2436 |
|---|---|---|---|---|---|
| Gruenlab | C | T | G | G | A |
| NCBI | A | C | C | T | G |

Gruenlab Reference Sequence (1-2,837) (SEQ ID NO: 31):

```
    Del_F--------------->
  1 AGCCTGCCTA CCACAGAGAA TGCCTTGGAA TCAGAGGTTC
 41 CCTGAAGAGA CCCTCTCCTC TTAGAATAAT CCAAAACCAG
 81 AATCTCCAGA GCCCCGTGGT CAAAACTAAA ACGTTCCATC
121 TAGGAGTGAG AGAGCACGAT ATCTACTTCC TCACACTTCT
161 CCTCGGTTCT CAAATAAAAG CGCTCACTTA CATTTGCCAT
201 CTTTATTCTG TGATCCGTTT TTATGTTACA GCAAATAAGC
241 AAATTATGAG GTCCTCTGGG CGAAAGGAAA ATCAGCATGG
281 AATGTAAGTT ATTGTGCCAT CTAGAGAAAA CGTGAGAGGC
321 TGGAaGCCTC MATCAACTGT CTTCCTTGAA GAATAACCTA
361 GATCTTGGCT CCCACTGGnC AAAGATGAGT GGGGGTTATT
```

```
 401 GTCTTCTCTA AGAAACTAAA cGTCCCTCAC ATGCTTGAAG
                         <---------------
 441 ATGTCGCAAG GGAGACCTGA TGGCCCCATT TCTGTGAGGT
       -Del_C
 481 TGTTCCTCAA AGAAGAATCA AAGATTTCAG TCACATTAGC
 521 ATCATCATGT TCTCTTAGTC CAGAATTTTT CAGCAAACAT
 561 ATTCCACAAA ATTTTCTGCA AGTTCAGGGT ACATATAGCA
 601 GGTGTAGTGG ATTTTTGTTA TGTTTTAATA TAACATACTA
 641 GAGAAAATCC AGAACATtCT tCTCCCTCTC TCTTCTTCAT
 681 CACATTCACA TCTCAGCCTA TAGAGCAGAG TTTATTCCCT
 721 AGTATAATAT CAAGGCCTGT TTTAAAAATA TATATATTAT
 761 ACATGTGAAT GAGAAATGAG TCACATTTAT TTTACCATGT
 801 CTCTGGTTTT TAAATAAAAT TAAAAGGTTG GGAAACTGTT
 841 TTTCAGTGTC ACAACCTCTC TGTTCTTACT ACCATAATAT
 881 TTACTTGATA TTATTTCAGT TCTTCCTTCC CCACACCCAT
 921 GTTGAATCCC AGACCACAAA CTACTGTAAT TTTTCTTTAT
 961 TATTCaACAT ATGTAGGAAT GCAGAATTAA AATTATTGAT
1001 CAAGTTTCAT GCAAAGTTCC AAAACCAAAG AAGAAAGAA
1041 AGGAAGAGAG GAAAAAAGAG AGAAAGACAG GGAGAAAAAT
                 [RepeatUnit1]
1081 AAAAGAAGG AAAGAGAGGA AGGAAAGAGA GGAAGGAAAG
       [RepeatUnit2]       [SNP1][RepeatUnit3]
1121 GAAGGAAGGA AGGAAGGAAG GAAGAAAGGA AGGAAGGAAA
       [RepeatUnit4] [RepeatUnit5]
1161 GAATGAAGGA AGGAAGGAAG GAAGGGAGGG AGGAAATCAG
1201 ACCTTTTCAT TTCATCGGGA TACCTACCAC CTCTCTTTTT
1241 GACTCAAGCT AATGTTAAAT GTTAAAAGA GTCTCCATTT
1281 TTAGAATACA CCAACCAATA GAAGGACCCC CCCATGCCCT
1321 AGAGCTCCCT GGATAGTAGA AAATTAGTCA AAATTTAAA
1361 ATTTACTATA GATGATCCAT AAAATTAAAA ATCATACAAA
1401 GCATGTTAAG AGCTGGGTGA CATATATATT AACTATAAAG
1441 AGAGCAGATA TAGAAAGGAA GCCAACATTT ATCTAGCAGA
1481 AGAAAAAAAC ACCATCATTT GTATCAATAA AAAGCATGTA
1521 TGATGAGCGG GCATGGAGGC TTATGCCTAT AACCCAGCAC
1561 TTTGGGAGGC CAAGGCATGT GGGTCGCTTA AGTCCAAGAG
1601 TTCAAGACCA GCCTGGGCAA CAATGGCAAA AATCCGTCTC
1641 TACTAAAAGT GCAAAAAATT GGCCAGGTGT GGTGGTACAT
1681 GCCTGTAGTC CCAGCTAGTC AGGTGGCTGA AGCAGAAGGA
1721 TTCCCTGAGC CTGGGAGATC GAGGCTGAAG TGAGCCTTGA
1761 TCATGCTACT GCACTCCAGC CTGGGTGACA GAGCGAGACC
1801 CTGTCTCAAA AAAAAAAAA AATGCATAAA AATGTTCATT
1841 TACATCCTCA TTTAACCCAT ACCATACTGT AtTCTACTTG
1881 CAGTATTTGC TAACTACTCC CCAGATAGAT GGGCTCACTT
1921 TGAGGCCAAG GATTGTGTTC TACCATAATC TCATTCCTTC
1961 AGCACAGCTC AGCACCTGGC AAATTGGAGG CAACAAATGT
2001 CTATGGATCC CTCTGTAACC ATGAACAAGT CAGTCAGGGT
2041 ACCTGCACTG TCAAAACTTA CAATTAACTG ATAGTATGT
2081 ATTTGATGAG GGGAACTGAA TTACAGGGAA ACCTAGGTTA
2121 GGCCAAGTGT TGCTTTCGTC ACCAATTCAC AGTTAAGGAA
2161 ACTGAGGCCA CGGGCCACCC AGCTTAGGAC TTTTGACTAT
2201 AAACCCTGAG ATCTCTCTCc TTTaCATAAG CATTTTGTTT
2241 TCATTGCTGT TGACACTTTG TTAATCTTGC TtACTtAAAA
2281 CTAaTTTCTG CTAATAGCTT CAGGGTCTTT AGCAACTGTC
2321 AGCATGTAAT GTGTCTGCAT TTCATATATA TAATTAGTTT
2361 TCATGGCAAC AGTCCACTTT TAGTCAATCA ACATTATAAA
2401 GTTAGTTATT TATTTATTTA TTTATTTATT TATTGACTGA
2441 TACGGAGTTT TGCTCTTGTT GCCCAGGCTG GAGTACAAGG
2481 GCCCAATCTT GGCTCACTGC AACCTCCGCC TCCCGGGTTC
2521 AAGCAATTCT CCTGCCTCAG CCTCCTGAGT AGCTGGGAaT
2561 TATAGGTGCC CGCCACCACA CCCGGCTAAT TTTTGTATTT
          <----------------Del_R
2601 TtCAGTAGAG ACGGGGTTTC ACCATGGCAG CCAGGCTGGT
2641 CTCAAACTCC TCACCTCAGG TGATCCAACT CSCCTCAGCC
2681 TCCCAAAGTG CTGGGATTAC AAGTGTGAGC CACCGCGCCT
2721 GGCAACATTA TAAACTTATA ATGAATTTAT GGAGTGTTAC
2761 TAGTAAACAA AATGAATATT CTTTAAATAA AAAAAATTTC
2801 TAAAAGCCTC TCAAATGTGC TTGTCTTTCT CCTTGCA
```

Green = flanking sequence
Black = deletion sequence
Red = purine-rich region

NCBI sequence: (21,571-24,406) (SEQ ID NO: 32)

```
agcctgccta ccacagagaa tgccttggaa tcagaggttc
cctgaagaga ccctctcctc ttagaataat ccaaaaccag
aatctccaga gccccgtggt caaaactaaa acgttccatc
taggagtgag agagcacgat atctacttcc tcacacttct
cctcggttct caaataaaag cgctcactta catttgccat
ctttattctg tgatccgttt ttatgttaca gcaaataagc
aaattatgag gtcctctggg cgaaaggaaa atcagcatgg
aatgtaagtt attgtgccat ctagagaaaa tgtgagaggc
tggaagcctc aatcaactgt cttccttgaa gaataaccta
gatcttggct cccactggca aagatgagtg ggggttattg
tcttctctaa gaaactaaac gtccctcaca tgcttgaaga
tgtcgcaagg gagacctgat ggccccattt ctgtgaggtt
gttcctcaaa gaagaatcaa agatttcagt cacattagca
```

-continued

```
tcatcatgtt ctcttagtcc agaattttc agcaaacata
ttccacaaaa ttttctgcaa gttcagggta catatagcag
gtgcagtgga tttttgttat gttttaatat aacatactag
agaaaatcca gaacattctt ctccctctct cttcttcatc
acattcacat ctcagcctat agagcagagt ttattcctta
gtataatatc aaggcctgtt ttaaaaatat atatattata
catgtgaatg agaaatgagt cacatttatt ttaccatgtc
tctggttttt aaataaaatt aaaaggttgg gaaactgttt
ttcagtgtca caacctctct gttcttacta ccataatatt
tacttgatat tatttcagtt cttccttccc cacacccatg
ttgaatccca gaccacaaac tactgtaatt tttctttatt
atcaacatat gtaggaatgc agaattaaaa ttattgatca
agtttcatgc aaagttccaa aaccaaagaa agaagaaag
gaagagagga aaaagagag aaagacaggg agaaaaataa
aaagaaggaa agagaggaag gaaagagagg aaggaaagga
aggaaggaag gaaggaagga agaaaggaag gaaggaaaga
atgaaggaag gaaggaagga agggagggag gaaatcagac
cttttcattt catcgggata cctaccacct ctcttttga
ctcaagctaa tgttaaatgt taaaaagagt ctccattttt
agaatacacc aaccaataga aggaccccc catgccctag
agctccctgg atagtagaaa attagtcaaa aatttaaaat
ttactataga tgatccataa aattaaaaat catacaaagc
atgttaagag ctgggtgaca tatatatt aactataaag
agagcagata tagaaaggaa gccaacattt atctagcaga
agaaaaaaac accatcattt gtatcaataa aaagcatgta
tgatgagcgg gcatggaggc ttatgcctat aacccagcac
tttgggaggc cgaggcatgt gggtcgctta agtccaagag
ttcaagacca gcctgggcaa caatggcaaa aatccgtctc
tactaaaagt gcaaaaatt ggccaggtgt ggtggtacat
gcctgtagtc ccagctagtc aggtggctga agcagaagga
ttccctgagc ctgggagatc gaggctgaag tgagccttga
tcatgctact gcactccagc ctgggtgaca gagcgagacc
ctgtctcaaa aaaaaaaaa aaatgcataa aaatgttcat
ttacatcctc atttaaccca taccatactg tattctactt
gcagtatttg ctaactactc cccagataga tgggctcact
ttgaggccaa ggattgtgtt ctaccataat ctcattcctt
cagcacagct cagcacctgg caaattggag gcaacaaatg
tctatggatc cctctgtaac catgaacaag tcagtcaggg
taactgcact gtcaaaactt acaattaact ggatagtatg
tatttgatga ggggaactga attacaggga aaacctaggtt
```

```
aggccaagtg ttgctttcgt caccaattca cagttaagga
aactgaggcc acgggccacc cagcttagga cttttgacta
taaaccctga gatctctctc ccttacataa gcattttgtt
ttcattgctg ttgacacttt gttaatcttg cttacttaaa
actaatttct gctaatagct tcagggtctt tagcaactgt
cagcatgtaa tgtgtctgca tttcatatat ataattagtt
ttcatggcaa cagtccactt ttagtcaatc aacattataa
acttatttat ttatttattt atttatttat ttattggctg
atacggagtt ttgctcttgt tgcccaggct ggagtacaag
ggcccaatct tggctcactg caacctccgc ctcccgggtt
caagcaattc tcctgcctca gcctcctgag tagctgggat
tataggtgcc cgccaccaca cccggctaat ttttgtattt
tcagtagaga cggggtttca ccatggcagc caggctggtc
tcaaactcct cacctcaggt gatccaactc gcctcagcct
cccaaagtgc tgggattaca agtgtgagcc accgcgcctg
gcaacattat aaacttataa tgaatttatg gagtgttact
agtaaacaaa atgaatattc tttaaataaa aaaatttct
aaaagcctct caaatgtgct tgtctttctc cttgca
```

Green = flanking sequence
Black = deletion sequence

Example 11 Functional Effects of the Deletion and Polymorphisms in the Purine-Rich Region of DCDC2 Intron 2

The 170basepair purine-rich region in intron 2 of DCDC2 (starting at 24,434,282, ENSEMBL database version 33 September 2005), is a very unique sequence comprised of nearly G and A bases exclusively. TESS (24) comparison to the TRANSFAC database identified 131 putative transcription factor binding sites distributed through this region, including four copies each of PEA3 (AGGAAA) and NF-ATp (AGGAAAG) sites in dbSTS ID 808238 (Table 3). Both transcription factors are expressed in mouse brain. PEA3 is associated with sexual function and peripheral motor neuron arborization (25). NF-ATp mediates rapid embryonic axon extension necessary for forming neuronal connections (26), which would complement the putative function of the doublecortin peptide domains in DCDC2. The presence of these binding sites suggests that the purine-rich region likely functions as an enhancer or regulatory region that could modify DCDC2 expression in terms of tissue or cell specificity, developmental timing, or quantity. To show that this region can actually bind transcription factor proteins, short double-stranded oligonucleotide probes, EMSA1, EMSA2, EMSA3, and EMSA4 (positions shown in figure below), were synthesized from the sequence of the purine rich region and tested for protein binding using the electrophoretic mobility shift assay:

Purine-rich region in intron 2 of DCDC2
(SEQ ID NO:33):

```
1001 CAAGTTTCAT GCAAAGTTCC AAAACCAAAG AAAGAAAGAA
                                              ↓
1041 AGGAAGAGAG GAAAAAAGAG AGAAAGACAG GGAGAAAAAT
                  ↓--------EMSA2-------↓
        -------EMSA1-------↓       ↓-------EMSA3--
1081 AAAAAGAAGG AAAGAGAGGA AGGAAAGAGA GGAAGGAAAG

-----↓                       ↓--------EMSA4--
1121 GAAGGAAGGA AGGAAGGAAG GAAGAAAGGA AGGAAGGAAA
       ----↓
1161 GAATGAAGGA AGGAAGGAAG GAAGGGAGGG AGGAAATCAG
```

(Black bases = deletion sequence)
(Red bases = purine-rich region)
(Underline = repeat units described in TABLE 3)

EMSA Sequences:

| | Primer | Complementary Primer |
|---|---|---|
| EMSA1 | TAAAAAGAAGGAAAGAGAGG | CCTCTCTTTCCTTCTTTTA |
| EMSA2 | GAGAGGAAGGAAAGAGAGGA | TCCTCTCTTTCCTTCCTCTC |
| EMSA3 | GAGAGGAAGGAAAGGAAGGA | TCCTTCCTTTCCTTCCTCTC |
| EMSA4 | AAGGAAGGAAGGAAAGAATG | CATTCTTTCCTTCCTTCCTT |

Figure 6:
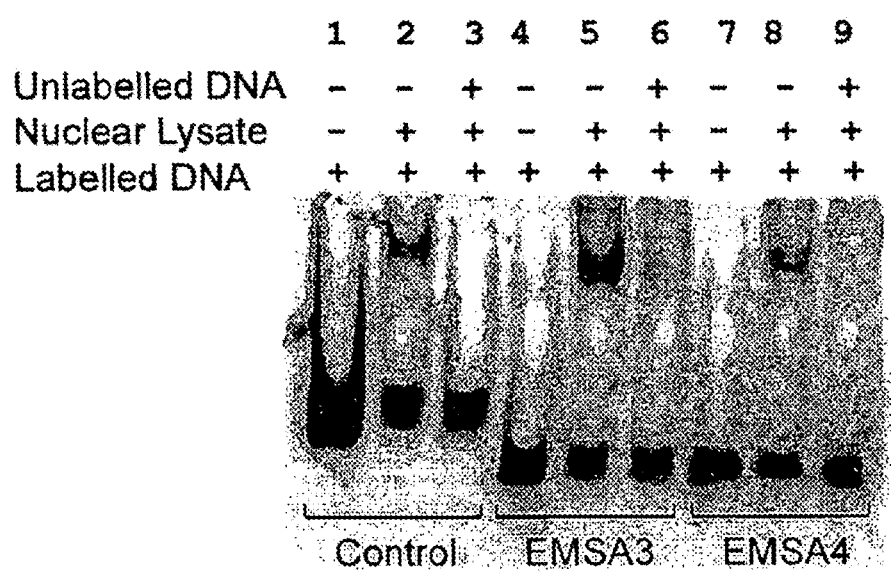
FIG. 6 shows the results of Electrophoresis Mobility Shift Assay on EMSA3 and EMSA4, which show that binding of nuclear proteins to these short doublestranded domains changes their electrophoretic mobility, indicating that it is likely that the short (20 bp) DNA domains bind transcription factors. This suggests that this region is one that can enhance gene expression/is an enhancer.

Electrophoretic Mobility Assay:

In the autoradiograph (FIG. 6), the Oct2A transcription factor recognition sequence (Control, lanes 1, 2, 3), EMSA3 (lanes 4, 5, 6) and EMSA4 (lanes 7, 8, 9) were fluorescently labeled and resolved by non-denaturing polyacrylamide gel electrophoresis. Migration was shifted when human brain nuclear cell lysate, containing transcription binding proteins, was mixed with the labeled probes (Control lane 2, EMSA3 lane5, and EMSA4 lane 8), showing that similar to Control, EMSA3 and EMSA4 bind nuclear proteins. Protein binding was then competitively and specifically inhibited by adding unlabeled ("cold") DNA (control lane3, EMSA3 lane 6, and EMSA4 lane 9).

Therefore, the polymorphisms of the purine-rich region—including the 2,445 base deletion—could act by disrupting or modifying DNA-protein interactions, and the specific DCDC2 enhancer-regulatory function encoded in this intron. The result would be a profound effect on DCDC2 expression, which, as shown by the RNAi data (Example 9), would have a significant effect on neuronal migration and ultimately reading ability.

Discussion

Applicants' previous studies showed transmission disequilibrium to JA04. They systematically interrogated the 6p22 DYX2 locus for a candidate gene that could confer susceptibility for RD. Starting with single-marker QTDT analysis they found the strongest peak and concentration of transmission disequilibrium with SNPs in DCDC2. The extent of intermarker linkage disequilibrium clustered through the 1.5 Mb of genomic sequence suggests adequate marker density in this region, and seven haplotype blocks. Blocks spanning DCDC2 also show significant transmission disequilibrium with several quantitative reading phenotypes in the context of preserved IQ, suggesting a specific effect on reading performance and not generalized or global effects on brain function. This fits the definition of the cognitive phenotype for RD and the entry criteria for subject collections; CLDRC subjects have a minimum IQ score of 80.

Reported here are the results from 147 SNP markers, but originally 152 consecutive markers were queued in the high-throughput genotyping strategy. Four markers failed PCR and were dropped from the analysis. A fifth marker, C_449792, was flagged for non-Mendelian transmission and was set aside. Only after completion of the single-marker QTDT analysis did Applicants confirm LOH with C_449792 in samples not subjected to multiple displacement amplification (MDA) and discover the 2,445 bp deletion in intron 2 of DCDC2, between the exons encoding the two doublecortin domains.

The 2,445 bp deletion, including minor alleles of dbSTS ID 808238, is in strong linkage disequilibrium with reading performance (P=0.00002, Table 2). Furthermore, dbSTS ID 808238 encodes multiple copies of PEA3 and NF-ATp sites that are active in brain. Loss of this entire regulatory region, as would happen with the common large deletion Applicants found in dyslexics, would therefore have profound effects on DCDC2 function. Polymorphisms would disrupt PEA3 and NF-ATp sites, which may explain dyslexia in subjects without the common deletion, or the variation of reading ability due to allelic heterogeneity.

DCDC2 (also called RU2 and KIAA1154, MIM: 605755) is located in the DYX2 locus 500 kb from JA04. The function is unknown but it contains two doublecortin peptide domains that were originally described in the doublecortin gene (DCX, MIM: 300121) encoded on the X chromosome. DCX encodes a cytoplasmic protein that directs neuronal migration by regulating the organization and stability of microtubules, and is mutated in human X-linked lissencephaly (27) and double cortex syndrome. Lissencephaly is a neuronal migration defect that produces profound mental retardation and seizures (28). Double cortex syndrome is caused by arrested migration halfway to the cortex producing a subcortical neuronal band heterotopia or "double cortex." For both syndromes the large majority of point mutations cluster within the conserved doublecortin peptide motifs of DCX, which are also encoded in DCDC2.

Converging imaging data implicate three important regions in the left hemisphere that are important for fluent reading: the anterior system in the inferior frontal region, the dorsal parietotemporal system involving the angular, supramarginal, and posterior portions of the superior temporal gyri, and the ventral occipitotemporal system involving portions of the middle temporal and middle occipital gyri (3, 29). Imaging studies of dyslexic adults and children show a disruption of posterior reading systems in parieto-temporal and occipito-temporal regions (30). Yet DCDC2 is highly expressed in the same regions activated by fluent and dyslexic readers, suggesting that dysregulation—attributable to polymorphisms of a regulatory region—and not complete disruption of a protein product participating in axonal guidance and growth, could explain the expression patterns.

These findings are consistent with the hypothesis that dyslexia is associated with subtle changes—like the anecdotal microscopic anomalies reported by Galaburda and colleagues (31)—in the migration of neurons in developing neocortex. Similarities in structure and cellular function between DCDC2 and DCX, a gene known to be critical to neuronal migration, further supports a hypothesis for impaired neuronal migration. Loss of function of DCX causes severe developmental disruption in neocortex, and dyslexia in contrast is not characterized by large malformations of neocortex. The DCDC2 alleles that associate with dyslexia, however, would not be expected to be nulls, and so even if DCX and DCDC2 had similarly critical roles in neuronal migration, large malformations would not be an expected phenotype for the described alleles. In addition, a comparison of the RNAi results following DCX RNAi (32) with that following DCDC2 RNAi suggest that DCX may be necessary for neuronal migration while DCDC2 may be more modulatory. Unlike the effects of DCX RNAi treatment (32), DCDC2 RNAi treatment allows cells to migrate farther, attain typical migratory bipolar morphologies, and does not induce the formation of large sub-cortical band heterotopia. While the RNAi treatment does not exclusively target neurons that populate reading centers, when considered in the context of DCDC2 expression in inferior and medial temporal cortex, it offers a plausible pathophysiologic mechanism for RD due to genetic expression heterogeneity. DCDC2 heterogeneity is also consistent with other pathophysiologic mechanisms. Imaging studies have shown a functional disruption of a more subtle nature—demonstrable only in composite maps of pooled subjects imaged at 1.5 tesla—in areas where heterotopias have not been described. Accordingly, it may be that DCDC2 heterogeneity sensitizes the dyslexic reader to disruption in the development of "a hierarchy of local combination detectors" in the occipito-temporal system, as postulated most recently by Dehaene and colleagues (33).

Previous attempts at transmission disequilibrium mapping with sparse densities of SNP markers in this region—31 SNPs over 10 Mb (34) and 57 SNPs over 5.7 Mb (35)—proved inconclusive. One of these studies, which found significant linkage disequilibrium with markers around the TTRAP gene (35), did not include markers over DCDC2. A recent study covering VMP, DCDC2, KIAA0319, TTRAP, and THEM2 identified maximum association with KIAA0319 (36). Given its specificity of expression in brain and the location of JA04 in the 5-prime untranslated region (22), KIAA0319 is a reasonable candidate, but the reported paucity of polymorphisms in disequilibrium with reading phenotypes (35)—confirmed by sequencing in the CLDRC cohort—made it less attractive. Furthermore, in Applicants' population, transmission disequilibrium was mostly from short haplotypes confined to DCDC2 (blocks A through E), with minimal support for association from single markers within MRS2L, GPLD1, KIAA0319, TTRAP, and THEM2 (Supplementary Table 1; FIG. 7). Block F, spanning GPLD1 just telomeric of DCDC2, also has one haplotype in disequilibrium. Haploview and Gold show, however, that the strongest marker in F, C_2100443, shares weak intermarker disequilibrium with SNP 33 (D'=0.41 and 0.49 respectively) located in block C, suggesting transmission disequilibrium is due to polymorphisms in DCDC2. No other haplotypes spanning GPLD1 show significant disequilibrium (data not shown). The origin of the transmission disequilibrium from block G is unknown and it spans no recognizable coding sequences. Although it is located within 118 kb of a published peak in THEM2, Applicants found no disequilibrium with any Haploview block on either side of block G or spanning THEM2 (35). Haplotypes within block H, telomeric to G and also void of recognizable coding sequences, do not show significant disequilibrium with RD phenotypes. Overall then, conservative estimates of intermarker linkage disequilibrium blocks in this region are relatively short. Therefore, it is unlikely that transmission disequilibrium from DCDC2 in the CLDRC cohort is due to risk alleles of genes located elsewhere in the DYX2 locus.

The brain is a highly intricate organ that requires a complex orchestra of changes and growth to fully develop in humans. Regardless of the pathophysiologic mechanisms, RD is a complex phenotype and several, if not many, genes are involved. Since they are often functionally grouped on chromosomes, it is possible that variations within more than one gene on 6p22 are responsible for interindividual differences in RD, which may be apparent in further studies of additional populations.

Subjects and Methods

The following subjects and methods were used in the work described herein.

CLDRC RD Family Samples

The 536 samples (parents and siblings) consisted of 153 nuclear families collected by the Colorado Learning Disabilities Research Center (CLDRC) (37). Subjects included members of MZ twin pairs (in which case, only one member of the MZ twin pair was used), DZ twin pairs, and nontwin siblings. There were 34 families with one offspring, 94 families with two offspring, 19 families with three offspring, and 6 families with four or five offspring. Predominantly white middle-class families were ascertained from school districts in the state of Colorado, where at least one sibling had a school history of reading problems. Subjects with IQ less than 80 or for whom English was a second language were not included in the initial sample. Subjects with evidence of serious neurological, emotional, or uncorrected sensory deficits were excluded from the present analyses. The average age of the 221 siblings analyzed was 11.55 years, ranging from 8.02 to 18.53 years. The CLDRC cohort was evaluated at the University of Colorado with an extensive battery of psychometric tests described previously (11), consisting of cognitive, language, and reading tasks, and included the intelligence quotient and the Peabody individual achievement test (PIAT). Quantitative-trait data were provided for the following 11 phenotypes: orthographic coding (OC), is the ability to recognize words' specific orthographic patterns and was measured here with our experimental tests for orthographic choice (OCH) and homonym choice (HCH); a composite score for both tests (i.e. OC composite) was created by averaging the z scores for both tasks. Phonological decoding (PD) is the oral reading of nonwords, which have straightforward pronunciations that are based on their spelling. Phonemic awareness (PA) is the ability to isolate and manipulate abstract subsyllabic sounds in speech; for the present analyses, it was measured with an experimental phoneme-transposition (PTP) and phoneme-deletion (PDL) tasks, as well as with a composite score for both tests. WR was measured with an experimental timed-word-recognition (TWR) task and the untimed standardized PIAT word-recognition (PWR) task, which required subjects to read words aloud; a composite score for both tests was also created. Finally, the discriminant score (DISC) for reading was a weighted composite of the reading recognition, reading comprehension, and spelling subtests of the PIAT. These psychometric tasks have been described in detail elsewhere (17, 23, 37-39). The population average was estimated from the large twin database available at the CLDRC. After age regression and standardization, the phenotypic data for each of the reading tasks formed a continuous distribution of quantitative z scores, which were used in the analyses.

RNA Samples

Total RNA samples from 18 areas of adult human brain were purchased from Ambion (see FIG. 4), and were procured from 10 white donors ranging in age from 45 to 79 years, with unknown handedness. RNA samples could not be localized to either the left or right hemispheres. Six donors were male. Seven donors died due to cardiac (e.g. congestive heart failure) or respiratory disease (e.g. respiratory failure), one had liver cancer, one had bladder cancer, and one was listed as unknown.

MDA Amplification

All genomic DNA samples were amplified by MDA (Molecular Staging, Incorporated, New Haven, Conn.) (40). The quality of amplified samples was assessed with two restriction length polymorphisms (RFLPs) by 1% agarose gel electrophoresis; 84% of amplified samples could be genotyped with both 6p22 RFLPs. Deletions identified in amplified DNA were confirmed by resequencing non-amplified samples.

Genotyping

TaqMan Assay-on-Demand® and Assay-by-Design® probes (ABI, Foster City, Calif.) were used to genotype 109 and 39 SNPs respectively. Six SNPs failed web-based primer design for TaqMan and consequently were genotyped by pyrosequencing (Biotage AB, Uppsala, Sweden). The primers for these SNPs are presented in Supplementary Table 4.

Deletion Phenotype

The common 2,445 bp deletion was genotyped by allele-specific amplification with a combination of three primers in one reaction: universal forward primer (AGCCTGCCTAC-CACAGAGAA, SEQ ID NO: 3), reverse primer for non-deleted chromosomes (GGAACAACCTCACAGAAATGG, SEQ ID NO: 4), and reverse primer for deleted chromosomes (TGAAACCCCGTCTCTACTGAA, SEQ ID NO: 5). Reaction products were resolved on 1.5% agarose gels. The deletion fusion fragment was 176 bp and the non-deleted fragment was 486 bp.

DBSTS ID 808238 GENOTYPE:

The compound STR, dbSTS ID 808238, was genotyped by sequencing PCR products generated with forward primer (TGTTGAATCCCAGACCACAA, SEQ ID NO: 1) and reverse primer (ATCCCGATGAAATGAAAAGG, SEQ ID NO: 2). The sequencing method is described below. Sequence traces results were analyzed and alleles assigned with Mutation Surveyor version 2.6 (SoftGenetics, State College), by comparing samples to reference traces after alignment.

Error Checking

DNA samples were formatted into two 384-well plates with at least one negative control (no genomic DNA) and two positive controls (CEPH NA10848 and NA10849, Coriell Institute, Camden) in each quadrant of 384-well plates. Genetic analyses were only performed on data from plates where the negative control showed negative results, and positive controls showed identical genotypes. Two STR markers from the pseudo-autosomal regions of the sex chromosomes were genotyped to check the sex ID of samples. Data were preprocessed to remove genotype combinations that resulted in Mendelian incompatibilities, low-quality DNA samples, and to detect any pedigree errors. Lastly, all markers with extreme amounts of missing data were removed, to exclude loci where genotyping might have been problematic.

DNA Sequencing

PCR was used to generate 68 amplicons from 26 RD and 6 normal genomic DNA samples from RD sample set 1 for DCDC2, MRS2L, and KIAA0319. Upon completion of thermal cycling, the PCR products were treated with ExoSAP-IT (USB, Cleveland, Ohio) to remove residual dNTPs and primers. DNA sequencing was performed in both forward and reverse directions with Big Dye (ABI) fluorescently labeled dideoxy terminator and the reaction products were resolved by capillary electrophoresis and laser detection on a 3730XL Automated DNA Sequencer (ABI). Sequence alignments and comparisons were made using Phred, Phrap, Polyphred, Consed, and Mutation Surveyor (SoftGenetics, State College, Pa.).

Quantitative Real Time RT-PCR

TaqMan gene expression kits for eight genes in the candidate region (KIAA0319, DCDC2, MRS2L, GPLD1, ALDH5A1, TTRAP, HT012, and GMNN) and six control genes (GAPDH, 18S, β actin, HPRT1, PPIA and PKG1) were purchased from ABI. In the two steps of RT-PCR, RNA samples were reverse transcribed to cDNA with the High Capacity cDNA Archive Kit (ABI). Then real time PCR was performed with the default SDS condition on the 7900HT (ABI). Each sample was tested in triplicate. To control for genomic DNA contamination all of the brain RNA templates were subjected to a sham reverse transcription step with random primers and without RT enzyme, followed by PCR with primers from three of the control genes. To identify potential internal controls, six genes, GAPDH, 18S, 13 actin, HPRT1, PPIA and PKG1, were tested for consistent expression in all 18 brain samples. To compare RT-PCR efficiencies relative standard expression curves for the eight 6p22 and six control genes were generated. It demonstrated that efficiencies of target and reference are approximately equal. The comparative $C_T$ method, which normalizes expression to an endogenous reference and a calibrator, was used for quantitative relative gene expression.

Statistical Analysis

All data were stored in Microsoft Excel files. Genetic Analysis System (GAS) was used to assess the Mendelian transmission of alleles. Identity-by-descent (IBD) probabilities were estimated with SimWalk2. Applicants used QTDT to simultaneously test for transmission disequilibrium (40) in the presence of linkage by the orthogonal model (-ao) with variance components (-wega), and permutations for exact P values (-m1000–1). Through different modeling within QTDT Applicants tested for parent of origin effects (-ot), the significance of polygenic effects (-weg), evidence for linkage without association (-vega), total association (-at), and population stratification (-ap). Haploview and Gold were used to examine the haplotype structure of the markers, to generate haplotype blocks and to assess inter-marker linkage disequilibrium (LD). Haplotype-TDT was analyzed by FBAT.

In Utero RNAi

Plasmids were directly introduced into cells at the cerebral ventricular zone of living rat embryos by in utero electroporation as previously described (32). Cells were co-transfected with pCA-eGFP and DCDC2 shRNA plasmid or control shRNA plasmid. The shRNA plasmid directed against DCDC2 contained the hairpin sequence 5' cccac-caagcaattccagacaa(aca)ttgtctggaattgcttggtggg 3' (SEQ ID NO: 42) and the control sequence was 5' cccagtcaaggcatt-gaattaaa(aca)ttttaattcaatgccttgactggg 3' (SEQ ID NO: 43). The sequence was selected by its asymmetry and for absence of any matches to rat genomic sequence in the database. Four days after transfection rat embryonic brains were fixed with 4% paraformaldehyde and sectioned with a vibratome (Leica VT1000S) at 60~80 μm. eGFP fluorescence was observed nuclei were labeled with TOP-PRO-3 (Molecular Probes). Images were acquired with a Leica TCS SP2 confocal microscope system (0.5~1.0 um optical section) and processed using Photoshop 7.0. For cumulative probability migration plots the distance of each cell (200-1400 in each analysis condition) from the VZ surface was determined 4 days after transfection. Migration distances were determined with automated particle analyses in ImageJ (Wayne Rasband, Research Services Branch, National Institute of Mental Health, Bethesda, Md., USA).

Data Deposition: The sequences reported herein have been deposited in the dbSTS database (ID 808238, SEQ ID NO: 65).

REFERENCES

1. Shaywitz, S. E. & Shaywitz, B. A. (2003) *Pediatrics in Review* 24, 147-53.
2. Shaywitz, S. E., Shaywitz, B. A., Pugh, K. R., Fulbright, R. K., Constable, R. T., Mencl, W. E., Shankweiler, D. P., Liberman, A. M., Skudlarski, P., Fletcher, J. M., Katz, L., Marchione, K. E., Lacadie, C., Gatenby, C. & Gore, J. C. (1998) *Proc Natl Acad Sci USA* 95, 2636-41.
3. Shaywitz, B. A., Shaywitz, S. E., Pugh, K. R., Mencl, W. E., Fulbright, R. K., Skudlarski, P., Constable, R. T., Marchione, K. E., Fletcher, J. M., Lyon, G. R. & Gore, J. C. (2002) *Biol Psychiatry* 52, 101-10.
4. Finucci, J. M., Guthrie, J. T., Childs, A. L., Abbey, H. & Childs, B. (1976) *Ann Hum Genet* 40, 1-23.
5. DeFries, J. C., Fulker, D. W. & LaBuda, M. C. (1987) *Nature* 329, 537-9.
6. Smith, S. D., Kimberling, W. J., Pennington, B. F. & Lubs, H. A. (1983) *Science* 219, 1345-7.
7. Turic, D., Robinson, L., Duke, M., Morris, D. W., Webb, V., Hamshere, M., Milham, C., Hopkin, E., Pound, K., Fernando, S., Grierson, A., Easton, M., Williams, N., Van Den Bree, M., Chowdhury, R., Gruen, J., Stevenson, J., Krawczak, M., Owen, M. J., O'Donovan, M. C. & Williams, J. (2003) *Molecular Psychiatry* 8, 176-85.
8. Marino, C., Giorda, R., Vanzin, L., Molteni, M., Lorusso, M. L., Nobile, M., Baschirotto, C., Alda, M. & Battaglia, M. (2003) *Eur Child Adolesc Psychiatry* 12, 198-202.
9. Grigorenko, E. L., Wood, F. B., Golovyan, L., Meyer, M., Romano, C. & Pauls, D. (2003) *American Journal of Medical Genetics* 118B, 89-98.
10. Willcutt, E. G., Pennington, B. F., Smith, S. D., Cardon, L. R., Gayan, J., Knopik, V. S., Olson, R. K. & DeFries, J. C. (2002) *Am J Med Genet* 114, 260-8.
11. Kaplan, D. E., Gayan, J., Ahn, J., Won, T. W., Pauls, D., Olson, R. K., DeFries, J. C., Wood, F., Pennington, B. F., Page, G. P., Smith, S. D. & Gruen, J. R. (2002) *Am J Hum Genet* 70, 1287-98.
12. Fisher, S. E., Francks, C., Marlow, A. J., MacPhie, I. L., Newbury, D. F., Cardon, L. R., Ishikawa-Brush, Y., Richardson, A. J., Talcott, J. B., Gayan, J., Olson, R. K., Pennington, B. F., Smith, S. D., DeFries, J. C., Stein, J. F. & Monaco, A. P. (2002) *Nat Genet* 30, 86-91.
13. Barr, C. L., Shulman, R., Wigg, K., Schachar, R., Tannock, R., Roberts, W., Malone, M. & Kennedy, J. L. (2001) *Am J Med Genet* 105, 250-4.
14. Ahn, J., Won, T. W., Zia, A., Reutter, H., Kaplan, D. E., Sparks, R. & Gruen, J. R. (2001) *Genomics* 78, 19-29.
15. Petryshen, T. L., Kaplan, B. J., Liu, M. F. & Field, L. L. (2000) *Am J Hum Genet* 66, 708-14.
16. Grigorenko, E. L., Wood, F. B., Meyer, M. S. & Pauls, D. L. (2000) *Am J Hum Genet* 66, 715-23.
17. Gayan, J., Smith, S. D., Cherny, S. S., Cardon, L. R., Fulker, D. W., Brower, A. M., Olson, R. K., Pennington, B. F. & DeFries, J. C. (1999) *Am J Hum Genet* 64, 157-64.
18. Fisher, S. E., Marlow, A. J., Lamb, J., Maestrini, E., Williams, D. F., Richardson, A. J., Weeks, D. E., Stein, J. F. & Monaco, A. P. (1999) *Am J Hum Genet* 64, 146-56.
19. Field, L. L. & Kaplan, B. J. (1998) *Am J Hum Genet* 63, 1448-56.
20. Grigorenko, E. L., Wood, F. B., Meyer, M. S., Hart, L. A., Speed, W. C., Shuster, A. & Pauls, D. L. (1997) *Am J Hum Genet* 60, 27-39.
21. Cardon, L. R., Smith, S. D., Fulker, D. W., Kimberling, W. J., Pennington, B. F. & DeFries, J. C. (1994) *Science* 266, 276-9.
22. Londin, E. R., Meng, H. & Gruen, J. R. (2003) *BMC Genomics* 4, 25.
23. Olson, R., Wise, B., Conners, F., Rack, J. & Fulker, D. (1989) *Journal of Learning Disabilities* 22, 339-348.
24. Schug, J. (2003) in *Current Protocols in Bioinformatics*, eds. Baxevanis, A., Davison, D., Page, R., Petsko, G., Stein, L. & Stormo, G. (John Wiley & Sons, Inc.
25. Laing, M. A., Coonrod, S., Hinton, B. T., Downie, J. W., Tozer, R., Rudnicki, M. A. & Hassell, J. A. (2000) *Molecular & Cellular Biology* 20, 9337-45.
26. Graef, I. A., Wang, F., Charron, F., Chen, L., Neilson, J., Tessier-Lavigne, M. & Crabtree, G. R. (2003) *Cell* 113, 657-70.
27. Dobyns, W. B., Truwit, C. L., Ross, M. E., Matsumoto, N., Pilz, D. T., Ledbetter, D. H., Gleeson, J. G., Walsh, C. A. & Barkovich, A. J. (1999) *Neurology* 53, 270-7.
28. Dobyns, W. B. & Truwit, C. L. (1995) *Neuropediatrics* 26, 132-47.
29. Horwitz, B., Rumsey, J. M. & Donohue, B. C. (1998) *Proc. Nat. Acad. Sci. USA* 95, 8939-8944.
30. Shaywitz, S. E. & Shaywitz, B. A. (2005) *Biol Psychiatry* 57, 1301-9.
31. Galaburda, A. M., Sherman, G. F., Rosen, G. D., Aboitiz, F. & Geschwind, N. (1985) *Ann Neurol* 18, 222-33.
32. Bai, J., Ramos, R. L., Ackman, J. B., Thomas, A. M., Lee, R. V. & LoTurco, J. J. (2003) *Nat Neurosci* 6, 1277-83.
33. Dehaene, S., Cohen, L., Sigman, M. & Vinckier, F. (2005) *Trends Cogn Sci* 9, 335-41.
34. Deffenbacher, K. E., Kenyon, J. B., Hoover, D. M., Olson, R. K., Pennington, B. F., DeFries, J. C. & Smith, S. D. (2004) *Hum Genet* 11, 11.
35. Francks, C., Paracchini, S., Smith, S. D., Richardson, A. J., Scerri, T. S., Cardon, L. R., Marlow, A. J., Macphie, I. L., Walter, J., Pennington, B. F., Fisher, S. E., Olson, R. K., Defies, J. C., Stein, J. F. & Monaco, A. P. (2004) *Am J Hum Genet* 75, 1046-58. Epub 2004 Oct. 22.
36. Cope, N., Harold, D., Hill, G., Moskvina, V., Stevenson, J., Holmans, P., Owen, M. J., O'Donovan M, C. & Williams, J. (2005) *Am J Hum Genet* 76, 581-91. Epub 2005 Feb. 16.
37. DeFries, J. C., Filipek, P. A., Fulker, D. W., Olson, R. K., Pennington, B. F., Smith, S. D. & Wise, B. W. (1997) *Learning Disabilities: A Multidisciplinary Journal* 8, 7-19.
38. DeFries, J. C. & Fulker, D. W. (1985) *Behav Genet* 15, 467-73.
39. Olson, R. K., Forsberg, H. & Wise, B. (1994) in *The varieties of orthographic knowledge I: Theoretical and developmental issues*, ed. Berninger, V. W. (Kluwer Academic Publishers, Dordrecht, The Netherlands), pp. 27-71.
40. Dean, F. B., Nelson, J. R., Giesler, T. L. & Lasken, R. S. (2001) *Genome Res* 11, 1095-9.
41. Abecasis, G. R., Cookson, W. O. & Cardon, L. R. (2000) *Eur J Hum Genet* 8, 545-51.

TABLE 1

Single-marker QTDT analysis for markers with P value ≤0.01

| SNP ID | Gene | DISC | IQ | PTP | HCH | Ensembl Location | Celera Location |
|---|---|---|---|---|---|---|---|
| 33 | DCDC2 Int 6 | 0.0003 | | | | 24386848 | 25512242 |
| 49 | DCDC2 Int 1 | 0.0035 | | | | 24463129 | 25588523 |
| 72 | GPLD1 Int 24 | | | | 0.0018 | 24539037 | 25664490 |
| 117 | intergene | | | 0.0077 | | 24872844 | 25998238 |
| 130 | intergene | 0.0067 | | 0.055 | 0.0811 | 25022795 | 26142106 |

TABLE 2

QTDT analysis of the compound STR, dbSTS ID 808238.

| Allele | DISC | IQ | PTP | TWR | PWR | WR | PD | OCH | PDL | HCH | OC | PA |
|---|---|---|---|---|---|---|---|---|---|---|---|---|
| 1 | | | | | | | | | | 0.0478 | | |
| 3 | | | | | | | | | | | | |
| 4 | | | | | | | | | | | | |
| 30[1] | | | | 0.0918 | 0.023 | 0.0407 | | 0.0385 | | 0.00002 | 0.0035 | 0.085 |

[1]Allele 30: combined deletion and all remaining minor alleles of dbSTS ID 808238.

Supplementary Methods and Materials

SNP Map

As in other regions of the human genome, the sequences provided by Celera, NCBI, and Ensembl databases had substantial differences. While exon sequences were identical in all three databases there was considerable variation in intron and intergenic sequences and lengths. Consequently the order of 15 SNPs, such as SNPs 27 and 31 in intron 7 of DCDC2, depended on the map source (Supplementary Table 1; FIG. 7). For haplotype and intermarker linkage disequilibrium analyses Applicants chose the locations assigned by Ensembl.

Marker Panel

Applicants tested a total of 154 SNP markers spanning 1.5 Mb from JA03 at 24,033,400 bp through D6S2296 at 25,285,800 bp (Ensembl) in the CLRDC RD families. 109 SNPs were from the Celera database (www.celera.com) and 45 SNPs from the dbSNP database (www.ncbi.nlm.nih.gov/SNP). The marker density was 8.7 kb per SNP. Minor allele frequencies were greater than 5% for cSNPs and greater than 15% of all others.

TaqMan: PCR plates in 384-well configuration were formatted with the Hydra II plus-one liquid handling system (Matrix Technologies, Hudson, N.H.). Reaction volumes were 41 with 1.6 ng of template DNA and TaqMan Universal Master Mix without uracil-DNA-glycosylase (ABI). Plates were cycled in the PE 9700 (ABI): initial denaturation step of 10 min at 95° C., followed by 40 cycles of 15 sec at 95° C. and 1 min at 60° C. Fluorescent signals were collected on the 7900HT (ABI) and converted to genotype data by the Sequence Detection System (SDS, ABI).

Pyrosequencing: Primers for pyrosequencing are listed in Supplementary Table 4. A total of 20 µl PCR reaction contained 10 ng of genomic DNA, 0.4 units Hotstart Taq polymerase (Qiagen), 4 pmoles of forward PCR primer, 0.4 pmoles of reverse PCR primer (5'-T3 tag), 3.6 pmoles of biotinylated T3 primer, 2.5 mM MgCl$_2$, and 200 µM dNTPs. Thermal cycling conditions were 15 min at 95° C., following by 45 cycles (30 sec at 95° C., 45 sec at 56° C., 60 sec at 72° C.), 5 min at 72° C., and a hold at 4° C. Upon completion of PCR, the biotinylated PCR product from the entire reaction was purified by binding to streptavidin-sepharose (Amersham) using the Filter Prep tool according to the standard protocol provided by Pyrosequencing, Inc. The Pyrosequencer software automatically scored each reaction and assigned genotypes.

Genotyping Results

Applicants genotyped a total of 147 SNPs distributed through the 1.5 Mb region surrounding JA04 in 153 nuclear RD families recruited by the Colorado Learning Disabilities Research Center (CLDRC). Origins, locations, and allele frequencies for the entire panel of 147 SNPs are presented in Supplementary Table 1 (FIG. 7). The overall success rate for genotyping was 90%. The average marker density was one SNP per 10.2 kb. The average marker density within genes was one SNP per 4.8 kb.

DNA Sequence Analysis

Applicants sequenced PCR products generated from 26 RD and six non-RD samples selected from the CLDRC RD cohort corresponding to 21 exons of KIAA0319 (12.2 kb), 10 exons of DCDC2 (6.7 kb), and 11 exons of MRS2L (1.99 kb). No novel polymorphisms were identified in the exons or reported splice sites of KIAA0319 or DCDC2. Five non-synonymous cSNPs were found in MRS2L (Supplementary Table 1; FIG. 7): MRS5, MRS6 (SNP 58), MRS7, and MRS8 were in exon 1, and MRS9 was in exon 11. Four novel cSNPs were also found in the 5-prime untranslated region (MRS1 through MRS4). MRS3 changed the start codon from ATG to ATC. The minor alleles of MRS1(A), MRS3(C), MRS4(G), MRS5(T), and MRS6(T) were transmitted only once in the RD cohort. All nine SNPs in MRS2L were genotyped in the RD families by fluorescent dideoxy sequencing or pyrosequencing.

Websites

Celera: www.celera.com
Coriell Institute: locus.umdnj.edu/dbSNP
database: www.ncbi.nlm.nih.gov/SNP
ENDCODE: genome.cse.ucsc.edu/ENCODE/FBAT: www.biostatharvard.edu/~fbat/fbat.htm
GAS (Genetic Analysis System): www.hgmp.mrc.ac.uk/Registered/Option/gas.html
GOLD: www.sph.umich.edu/csg/abecasis/GOLD/index.html
Haploview: www.broad.mit.edu/personal/jcbarret/haplo/
Mutation Surveyor: www.softgenetics.com
Phrap, Phred, Consed: www.phrap.org/PolyPhred: droog.mbt.washington.edu/PolyPhred.html
Pyrosequencing: www.pyrosequencing.com
QTDT: www.sph.umich.edu/csg/abecasis/QTDT
SimWalk2: watson.hgen.pitt.edu/docs/simwalk2
TESS: URL: www.cbil.upenn.edu/tess
TRANSMIT: www-gene.cimr.cam.ac.uk/clayton/software/SUBSTITUTE

SUPPLEMENTARY TABLE 2a

Composition of haplotype blocks.

| Haplotype Block | Haplotype ID | Haplotype | Frequency |
|---|---|---|---|
| A | | | |
| 5 markers | 1 | A A A G G | 0.60 |
| SNP ID: 21, 22, 23, 24, and 25 | 2 | G C G G G | 0.25 |
| spanning 6523 bp in Ensembl | 3 | A A G A T | 0.07 |
| B | | | |
| 2 markers | 1 | G C | 0.63 |
| SNP ID: 26 and 27 | 2 | A T | 0.21 |
| spanning 17287.5 bp in Ensembl | 3 | G T | 0.15 |
| C | | | |
| 8 markers | 1 | G T G A G A T G | 0.62 |
| SNP ID: 32, 33, 34, 35, 36, 37, 38, and 39 | 2 | A T C G A T T C | 0.12 |
| spanning 33631 bp in Ensembl | 3 | G T G A G A T C | 0.06 |
| | 4 | A C C A A T T A | 0.06 |
| | 5 | A C C G A T A A | 0.05 |
| D | | | |
| 5 markers | 1 | G G G A G | 0.54 |
| SNP ID: 42, 43, 44, 45, and 46 | 2 | C G A T A | 0.15 |
| spanning 11472 bp in Ensembl | 3 | C A A T G | 0.13 |
| | 4 | C G A T G | 0.10 |
| E | | | |
| 3 markers | 1 | A G C | 0.53 |
| SNP ID: 47, 49 and 50 | 2 | G A T | 0.30 |
| spanning 16235 bp in Ensembl | 3 | A A C | 0.11 |
| F | | | |
| 5 markers | 1 | A T A A T | 0.64 |
| SNP ID: 68, 69, 70, 71, 72 | 2 | A A G G G | 0.22 |
| spanning 5368 bp in Ensembl | 3 | G T G G G | 0.11 |
| G | | | |
| 3 markers | 1 | C A T | 0.46 |
| SNP ID: 117, 118, and 119 | 2 | C C C | 0.38 |
| spanning 34413 bp in Ensembl | 3 | A C C | 0.12 |
| H | | | |
| 3 markers | 1 | T A G | 0.38 |
| SNP ID: 128, 129, and 130 | 2 | C G G | 0.31 |
| spanning 13466 bp in Ensembl | 3 | C G A | 0.21 |

SUPPLEMENTARY TABLE 3

Alleles and frequencies of the compound STR, dbSTS ID 808238.

| Allele | Repeat Unit1 | Repeat Unit2 | SNP1 | Repeat Unit3 | Repeat Unit4 | Repeat Unit6 | Allele Freq[1] |
|---|---|---|---|---|---|---|---|
| 1 | (GAGAGGAAGGAAA)2 | (GGAA)7 | | (GGAA)2 | (GGAA)4 | (GGAA)2 | 0.624 |
| 2 | (GAGAGGAAGGAAA)1 | (GGAA)9 | DelGAAA | (GGAA)0 | (GGAA)4 | (GGAA)2 | 0.003 |
| 3 | (GAGAGGAAGGAAA)1 | (GGAA)6 | | (GGAA)2 | (GGAA)4 | (GGAA)2 | 0.060 |
| 4 | (GAGAGGAAGGAAA)2 | (GGAA)6 | | (GGAA)2 | (GGAA)4 | (GGAA)2 | 0.106 |
| 5 | (GAGAGGAAGGAAA)2 | (GGAA)8 | | (GGAA)2 | (GGAA)4 | (GGAA)2 | 0.028 |
| 6 | (GAGAGGAAGGAAA)2 | (GGAA)8 | | (GGAA)2 | (GGAA)3 | (GGAA)2 | 0.039 |
| 7 | (GAGAGGAAGGAAA)2 | (GGAA)8 | | (GGAA)1 | (GGAA)4 | (GGAA)2 | 0.003 |
| 8 | (GAGAGGAAGGAAA)2 | (GGAA)7 | DelGAAA | (GGAA)0 | (GGAA)4 | (GGAA)2 | 0.003 |
| 9 | (GAGAGGAAGGAAA)1 | (GGAA)7 | | (GGAA)2 | (GGAA)4 | (GGAA)2 | 0.005 |
| 10 | (GAGAGGAAGGAAA)2 | (GGAA)4 | | (GGAA)2 | (GGAA)4 | (GGAA)2 | 0.044 |
| 14 | x | x | x | x | x | x | 0.085 |

[1]Frequency among parents of the CLDRC families
Allele 14 is the 2,446 bp deletion

SUPPLEMENTARY TABLE 4

Pyrosequencing primers.

| Marker | PCR primer 1 | PCR primer 2 |
|---|---|---|
| rs503811 | ATTAACCCTCACTAAAGGGAtgtctagaggaatggattctgacc | TTCTAATACGACTCACTATAGGGAGAgcattattcaaaagcaagctgtgt |
| rs1925432 | ATTAACCCTCACTAAAGGGAtcaattatccaatgggaaagag | TTCTAATACGACTCACTATAGGGAGAcatctctaacacaggcaggatg |
| rs1886705 | ATTAACCCTCACTAAAGGGAttgggtgctccttaaaccatttt | TTCTAATACGACTCACTATAGGGAGAtctgtcctttactctttccctgaa |
| rs1001075 | ATTAACCCTCACTAAAGGGAttcaagaatagggaaatgttca | TTCTAATACGACTCACTATAGGGAGAtgcttccttaatggctgcttaac |
| rs1511468 | ATTAACCCTCACTAAAGGGAcattctgttcttggatggagacc | TICTAATACGACTCACTATAGGGAGAgaacccaaacacttgaccaaaag |
| rs304257 | ATTAACCCTCACTAAAGGGAacttgccaccatcttttgttgtt | TTCTAATACGACTCACTATAGGGAGAcatggatcttcaccattgtcaac |

| Marker | Extension Primer |
|---|---|
| rs503811 | GTTTGAATAGGAAAGGAT |
| rs1925432 | GATGCAATCAATGGTAAT |
| rs1886705 | ACCTGTGCACAGTTTGA |
| rs1001075 | TGGCTGCTTAACAACCCAATAAAT |
| rs1511468 | GGAGACCTCTGCAGATACGTACTA |
| rs304257 | ATCTTCAGCATTGTCAACCTGACC |

| Marker | PCR primer 1 | PCR primer 2 | Extension Primer |
|---|---|---|---|
| rs503811 | SEQ ID NO: 44 | SEQ ID NO: 45 | SEQ ID NO: 46 |
| rs1925432 | SEQ ID NO: 47 | SEQ ID NO: 48 | SEQ ID NO: 49 |
| rs1886705 | SEQ ID NO: 50 | SEQ ID NO: 51 | SEQ ID NO: 52 |
| rs1001075 | SEQ ID NO: 53 | SEQ ID NO: 54 | SEQ ID NO: 55 |
| rs1511468 | SEQ ID NO: 56 | SEQ ID NO: 57 | SEQ ID NO: 58 |
| rs304257 | SEQ ID NO: 59 | SEQ ID NO: 60 | SEQ ID NO: 61 |

We claim:

1. A method of detecting, in a sample obtained from a human, a variant doublecortin domain containing 2 (DCDC2) gene that comprises an alteration that is:
   a deletion in intron 2 comprising SEQ ID NO: 75; or
   an allele of the short tandem repeat region of intron 2 that comprises one of SEQ ID NO: 77-SEQ ID NO: 86, comprising:
   (a) combining the sample with a polynucleotide probe that hybridizes, under highly stringent conditions, to the variant DCDC2 gene, but not to a wild type DCDC2 gene, wherein the variant DCDC2 gene comprises an alteration that is:
   a deletion in intron 2 comprising SEQ ID NO: 75 or
   an allele of the short tandem repeat region of intron 2 that comprises one of SEQ ID NO: 77-SEQ ID NO: 86; and
   (b) determining whether hybridization occurs, wherein the occurrence of hybridization indicates that the variant DCDC2 gene that comprises the alteration is present in the sample.

2. The method of claim 1, wherein the deletion comprises SEQ ID NO: 75, wherein the polynucleotide probe hybridizes to intron 2 at the flanking base at the start of the deletion in intron 2 and at the flanking base at the end of the deletion in intron 2, wherein the flanking base at the start of the deletion is C and the flanking base at the end of the deletion is T.

3. The method of claim 1, wherein the deletion is genotyped by allele-specific amplification with a combination of three primers: a universal or shared forward primer; a reverse primer for non-deleted chromosomes and a reverse primer for deleted chromosomes.

4. The method of claim 3, wherein in (a), the sample is combined with a universal or shared forward primer of sequence:

AGCCTGCCTACCACAGAGAA;    (SEQ ID NO: 3)

a deletion reverse primer of sequence:

TGAAACCCCGTCTCTACTGAA;    (SEQ ID NO: 4)

and
   a non-deletion reverse primer of sequence:

GGAACAACCTCACAGAAATGG.    (SEQ ID NO: 5)

5. A method of detecting, in a sample obtained from a human, a variant doublecortin domain containing 2 (DCDC2) gene that comprises an alteration that is:
   a deletion in intron 2 comprising SEQ ID NO: 75; or
   an allele of the short tandem repeat region of intron 2 that comprises one of SEQ ID NO: 77-SEQ ID NO: 86, comprising:
   (a) combining the sample with a polynucleotide probe that hybridizes, under highly stringent conditions, to the variant DCDC2 gene that comprises:
   a deletion in intron 2 comprising SEQ ID NO: 75; or
   an allele of the short tandem repeat region of intron 2 that comprises one of SEQ ID NO: 77-SEQ ID NO: 86, thereby producing a combination;
   (b) maintaining the combination produced in step (a) under highly stringent hybridization conditions; and
   (c) comparing hybridization that occurs in the combination with hybridization in a control sample, wherein the control sample includes a polynucleotide probe that does not bind to the variant DCDC2 gene or binds only to a wild type DCDC2 gene, and the control sample is the same type of sample as in (a) and is treated the same as the sample in (a), and
   wherein the occurrence of hybridization in the combination but not in the control sample indicates that the variant DCDC2 gene is present in the sample.

6. The method of claim 5, wherein the extent of hybridization is determined in step (c).

7. A method of detecting, in a sample obtained from a human, a variant DCDC2 gene that comprises an alteration that is:
   a deletion in intron 2 comprising SEQ ID NO: 75; or
   an allele of the short tandem repeat region of intron 2 of DCDC2 that comprises one of SEQ ID NO: 77-SEQ ID NO: 86,
   comprising:
   (a) combining the sample with a pair of polynucleotide primers, wherein the first polynucleotide primer hybridizes to one side of DNA that is present in the variant DCDC2 gene but not present in a wildtype DCDC2 gene and the second polynucleotide primer hybridizes to the other side of DNA that is present in the variant DCDC2 gene but not present in a wildtype DCDC2 gene;
   (b) amplifying DNA in the sample, thereby producing amplified DNA;
   (c) sequencing the amplified DNA; and
   (d) detecting in the amplified DNA the presence of variant DCDC2 DNA,
   whereby the variant DCDC2 gene is detected.

* * * * *

UNITED STATES PATENT AND TRADEMARK OFFICE
CERTIFICATE OF CORRECTION

PATENT NO. : 9,828,639 B2  
APPLICATION NO. : 13/967291  
DATED : November 28, 2017  
INVENTOR(S) : Jeffrey R. Gruen et al.

Page 1 of 1

It is certified that error appears in the above-identified patent and that said Letters Patent is hereby corrected as shown below:

At Column 1, please replace paragraph beginning on Line 23, with the following amended paragraph:

This invention was made with government support under R01 NS43530 awarded by National Institutes of Health. The government has certain rights in the invention.

Signed and Sealed this  
Twelfth Day of June, 2018

Andrei Iancu  
*Director of the United States Patent and Trademark Office*